US012653804B2

(12) United States Patent
Edelson

(10) Patent No.: US 12,653,804 B2
(45) Date of Patent: Jun. 16, 2026

(54) USES OF PLASMINOGEN ACTIVATOR INHIBITOR 1 (PAI-1) INHIBITORS

(71) Applicant: Eirion Therapeutics, Inc., Woburn, MA (US)

(72) Inventor: Jonathan Edelson, Nashua, NH (US)

(73) Assignee: Eirion Therapeutics, Inc., Woburn, MA (US)

( * ) Notice: Subject to any disclaimer, the term of this patent is extended or adjusted under 35 U.S.C. 154(b) by 1240 days.

(21) Appl. No.: 17/274,937

(22) PCT Filed: Sep. 12, 2019

(86) PCT No.: PCT/US2019/050890
§ 371 (c)(1),
(2) Date: Mar. 10, 2021

(87) PCT Pub. No.: WO2020/056191
PCT Pub. Date: Mar. 19, 2020

(65) Prior Publication Data
US 2022/0079911 A1 Mar. 17, 2022

Related U.S. Application Data

(60) Provisional application No. 62/731,076, filed on Sep. 13, 2018.

(51) Int. Cl.
| | |
|---|---|
| *A61K 31/341* | (2006.01) |
| *A61K 31/713* | (2006.01) |
| *A61K 45/06* | (2006.01) |
| *A61M 37/00* | (2006.01) |
| *A61N 2/00* | (2006.01) |
| *A61N 5/067* | (2006.01) |
| *A61P 17/14* | (2006.01) |

(52) U.S. Cl.
CPC .......... *A61K 31/341* (2013.01); *A61K 31/713* (2013.01); *A61K 45/06* (2013.01); *A61M 37/0015* (2013.01); *A61N 2/002* (2013.01); *A61N 5/067* (2021.08); *A61P 17/14* (2018.01); *A61M 2037/0023* (2013.01)

(58) Field of Classification Search
CPC .................................................. A61K 31/341
See application file for complete search history.

(56) References Cited

U.S. PATENT DOCUMENTS

| | | | |
|---|---|---|---|
| 3,725,540 | A | 4/1973 | Wahl |
| 3,964,482 | A | 6/1976 | Gerstel et al. |
| 4,075,096 | A | 2/1978 | Kawakami et al. |
| 4,075,196 | A | 2/1978 | Badertscher et al. |
| 4,152,170 | A | 5/1979 | Nagase et al. |
| 4,172,149 | A | 10/1979 | Pinto et al. |
| 4,373,526 | A | 2/1983 | Kling |
| 4,526,938 | A | 7/1985 | Churchill et al. |
| 4,533,254 | A | 8/1985 | Cook et al. |
| 4,618,664 | A | 10/1986 | Ohnishi |
| 4,908,154 | A | 3/1990 | Cook et al. |
| 5,008,110 | A | 4/1991 | Benecke et al. |
| 5,152,923 | A | 10/1992 | Weder et al. |
| 5,302,401 | A | 4/1994 | Liversidge et al. |
| 5,374,614 | A | 12/1994 | Behan et al. |
| 5,401,243 | A | 3/1995 | Borodic |
| 5,470,577 | A | 11/1995 | Gilchrest et al. |
| 5,502,045 | A | 3/1996 | Miettinen et al. |
| 5,510,118 | A | 4/1996 | Bosch et al. |
| 5,512,547 | A | 4/1996 | Johnson et al. |
| 5,554,372 | A | 9/1996 | Hunter |
| 5,576,016 | A | 11/1996 | Amselem et al. |
| 5,591,767 | A | 1/1997 | Mohr et al. |
| 5,613,952 | A | 3/1997 | Pressly, Sr. et al. |
| 5,629,021 | A | 5/1997 | Wright |
| 5,651,991 | A | 7/1997 | Sugiyama et al. |
| 5,652,274 | A | 7/1997 | Martin |

(Continued)

FOREIGN PATENT DOCUMENTS

| | | |
|---|---|---|
| AU | 2019/201316 A1 | 3/2019 |
| CA | 02067754 A1 | 2/1992 |

(Continued)

OTHER PUBLICATIONS

Vaughan et al. Arteriosclerosis, Thrombosis, and Vascular Biology, vol. 37, Issue 8, Aug. 2017; pp. 1446-1452.*
Alves, P.M. et al., Semisolid topical formulations containing nimesulide-loaded nanocapsules, nanospheres or nanoemulsion: development and rheological characterization, Pharmazie, 60:900-904 (2005).
Aoki K.R., Botulinum neurotoxin serotype A and B preparations have different safety margins in preclinical models of muscle weakening efficacy and systemic safety, Toxicon 40:923-928 (2002).
Badea, I. et al., In vivo cutaneous interferon-γ gene delivery using novel dicationic (gemini) surfactant-plasmid complexes, The Journal of Gene Medicine, 7:1200-1214 (2005).
Bansal, C. et al., Novel cutaneous uses for botulinum toxin type A, Journal of Cosmetic Dermatology, 5:268-272 (2006).

(Continued)

*Primary Examiner* — Brian E McDowell
(74) *Attorney, Agent, or Firm* — Choate, Hall & Stewart LLP; Brenda Herschbach Jarrell; Jade E. Varineau

(57) ABSTRACT

The present disclosures provides surprising insight into new technologies for treatment and/or prevention of certain types of hair loss (also known as alopecia), including androgenetic alopecia, alopecia areata, frontal fibrosing alopecia, and senescent alopecia. Among other things, the present disclosure provides surprising insight that plasminogen activator inhibitor-1 (PAI-1) inhibitors may be surprisingly effective and/or useful in the treatment and/or prevention of certain types of hair loss, including androgenetic alopecia, alopecia areata, frontal fibrosing alopecia, and senescent alopecia. Furthermore, the present disclosure provides insight that provided new technologies may not be particularly effective and/or useful in the treatment and/or prevention of other types of alopecia such as radiation-induced alopecia, chemotherapy-induced alopecia, and alopecia due to chronic discoid lupus erythematosus.

24 Claims, No Drawings

(56)                References Cited

U.S. PATENT DOCUMENTS

| | | | |
|---|---|---|---|
| 5,660,858 | A | 8/1997 | Parikh et al. |
| 5,670,484 | A | 9/1997 | Binder |
| 5,672,358 | A | 9/1997 | Tabibi et al. |
| 5,683,712 | A | 11/1997 | Cavazza |
| 5,753,241 | A | 5/1998 | Ribier et al. |
| 5,766,605 | A | 6/1998 | Sanders et al. |
| 5,851,452 | A | 12/1998 | Vallet Mas et al. |
| 5,858,410 | A | 1/1999 | Muller et al. |
| 5,925,341 | A | 7/1999 | Cervantes et al. |
| 5,932,562 | A | 8/1999 | Ostlund, Jr. |
| 5,948,433 | A | 9/1999 | Burton et al. |
| 5,965,154 | A | 10/1999 | Haralambopoulos |
| 5,993,852 | A | 11/1999 | Foldvari et al. |
| 5,994,414 | A | 11/1999 | Franco et al. |
| 6,007,803 | A | 12/1999 | Mandeville, III et al. |
| 6,007,856 | A | 12/1999 | Cox et al. |
| 6,010,715 | A | 1/2000 | Wick et al. |
| 6,039,936 | A | 3/2000 | Restle et al. |
| 6,087,327 | A | 7/2000 | Pearce et al. |
| 6,117,454 | A | 9/2000 | Kreuter et al. |
| 6,165,500 | A | 12/2000 | Cevc |
| 6,203,802 | B1 | 3/2001 | Handjani et al. |
| 6,224,853 | B1 | 5/2001 | Steel et al. |
| 6,265,180 | B1 | 7/2001 | Zuelli et al. |
| 6,274,150 | B1 | 8/2001 | Simonnet et al. |
| 6,312,708 | B1 | 11/2001 | Donovan |
| 6,334,856 | B1 | 1/2002 | Allen et al. |
| 6,358,917 | B1 | 3/2002 | Carruthers et al. |
| 6,387,411 | B2 | 5/2002 | Bruce et al. |
| 6,395,029 | B1 | 5/2002 | Levy |
| 6,429,189 | B1 | 8/2002 | Borodic |
| 6,455,058 | B1 | 9/2002 | Sun et al. |
| 6,458,373 | B1 | 10/2002 | Lambert et al. |
| 6,461,596 | B1 | 10/2002 | Taylor |
| 6,503,231 | B1 | 1/2003 | Prausnitz et al. |
| 6,558,941 | B2 | 5/2003 | Zuelli et al. |
| 6,573,241 | B1 | 6/2003 | Bigalke et al. |
| 6,589,588 | B1 | 7/2003 | Wester et al. |
| 6,611,707 | B1 | 8/2003 | Prausnitz et al. |
| 6,620,419 | B1 | 9/2003 | Lintner |
| 6,623,780 | B1 | 9/2003 | Stevens et al. |
| 6,632,440 | B1 | 10/2003 | Quinn et al. |
| 6,670,322 | B2 | 12/2003 | Goodnough et al. |
| 6,688,311 | B2 | 2/2004 | Hanin |
| 6,720,001 | B2 | 4/2004 | Chen et al. |
| 6,745,211 | B2 | 6/2004 | Kabasakalian et al. |
| 6,765,001 | B2 | 7/2004 | Gans et al. |
| 6,835,395 | B1 | 12/2004 | Semple et al. |
| 6,835,895 | B1 | 12/2004 | Asai et al. |
| 6,861,066 | B2 | 3/2005 | Van de Casteele |
| 6,869,610 | B2 | 3/2005 | Aoki et al. |
| 6,875,438 | B2 | 4/2005 | Kraemer et al. |
| 6,890,560 | B2 | 5/2005 | Seo et al. |
| 6,902,737 | B2 | 6/2005 | Quemin |
| 6,939,852 | B2 | 9/2005 | Graham |
| 6,974,578 | B1 | 12/2005 | Aoki et al. |
| 6,974,579 | B2 | 12/2005 | Brin et al. |
| 7,001,602 | B2 | 2/2006 | Schmidt |
| RE39,086 | E | 5/2006 | Carruthers et al. |
| 7,063,860 | B2 | 6/2006 | Chancellor et al. |
| 7,125,858 | B2 | 10/2006 | Filion |
| 7,226,605 | B2 | 6/2007 | Suskind et al. |
| 7,228,259 | B2 | 6/2007 | Freund |
| 7,255,865 | B2 | 8/2007 | Walker |
| 7,384,918 | B2 | 6/2008 | Graham |
| 7,419,996 | B2 | 9/2008 | Chow et al. |
| 7,507,419 | B2 | 3/2009 | Coleman, III |
| 7,531,193 | B2 | 5/2009 | Demarne et al. |
| 7,727,537 | B2 | 6/2010 | Modi |
| 7,758,871 | B2 | 7/2010 | Donovan |
| 7,763,663 | B2 | 7/2010 | McCarthy et al. |
| 7,838,011 | B2 | 11/2010 | Modi |
| 8,318,181 | B2 | 11/2012 | Edelson et al. |
| 8,623,811 | B2 | 1/2014 | Stone et al. |
| 8,658,391 | B2 | 2/2014 | Edelson |
| 8,710,010 | B2 | 4/2014 | Van Den Nest et al. |
| 8,710,011 | B2 | 4/2014 | Garcia Sanz et al. |
| 9,314,431 | B2 | 4/2016 | Modi |
| 9,340,587 | B2 | 5/2016 | Thompson et al. |
| 9,458,194 | B2 | 10/2016 | Ferrer Montiel et al. |
| 9,486,408 | B2 | 11/2016 | Edelson et al. |
| 9,486,409 | B2 | 11/2016 | Edelson et al. |
| 9,649,266 | B2 | 5/2017 | Edelson |
| 9,724,299 | B2 | 8/2017 | Kotyla |
| 9,725,483 | B2 | 8/2017 | Anton et al. |
| 9,770,400 | B2 | 9/2017 | Courtois et al. |
| 9,771,392 | B2 | 9/2017 | Ferrer Montiel et al. |
| 9,956,435 | B2 | 5/2018 | Ruegg et al. |
| 10,016,364 | B2 | 7/2018 | Nicolosi et al. |
| 10,016,451 | B2 | 7/2018 | Edelson et al. |
| 10,111,939 | B2 | 10/2018 | Thompson et al. |
| 10,201,594 | B2 | 2/2019 | Ruegg et al. |
| 10,285,941 | B2 | 5/2019 | Kotyla |
| 10,485,855 | B2 | 11/2019 | Edelson |
| 10,532,019 | B2 | 1/2020 | Edelson et al. |
| 10,576,034 | B2 | 3/2020 | Edelson et al. |
| 10,758,485 | B2 | 9/2020 | Kotyla |
| 10,905,637 | B2 | 2/2021 | Edelson et al. |
| 11,311,496 | B2 | 4/2022 | Edelson |
| 2002/0015721 | A1 | 2/2002 | Simonnet et al. |
| 2002/0034474 | A1 | 3/2002 | Sabel et al. |
| 2002/0048596 | A1 | 4/2002 | Cevc |
| 2002/0086036 | A1 | 7/2002 | Walker |
| 2002/0086838 | A1 | 7/2002 | Oh et al. |
| 2002/0098215 | A1 | 7/2002 | Douin et al. |
| 2002/0107199 | A1 | 8/2002 | Walker |
| 2002/0155084 | A1 | 10/2002 | Roessler et al. |
| 2002/0165179 | A1 | 11/2002 | Baker |
| 2002/0187164 | A1 | 12/2002 | Borodic |
| 2002/0193754 | A1 | 12/2002 | Cho |
| 2003/0072801 | A1 | 4/2003 | Curatolo et al. |
| 2003/0072841 | A1 | 4/2003 | Rajaiah et al. |
| 2003/0077240 | A1 | 4/2003 | LeGrow et al. |
| 2003/0077283 | A1 | 4/2003 | Ye |
| 2003/0086888 | A1 | 5/2003 | LeGrow et al. |
| 2003/0105000 | A1 | 6/2003 | Pero et al. |
| 2003/0108597 | A1 | 6/2003 | Chancellor et al. |
| 2003/0113349 | A1 | 6/2003 | Coleman |
| 2003/0138465 | A9 | 7/2003 | Douin et al. |
| 2003/0157138 | A1 | 8/2003 | Eini et al. |
| 2003/0194412 | A1 | 10/2003 | Baker et al. |
| 2003/0206955 | A1 | 11/2003 | Sonneville-Aubrun et al. |
| 2003/0211140 | A1 | 11/2003 | Mantripragada et al. |
| 2003/0217371 | A1 | 11/2003 | Vaughan et al. |
| 2003/0224020 | A1 | 12/2003 | Zabudkin et al. |
| 2003/0229141 | A1 | 12/2003 | Yu et al. |
| 2004/0003324 | A1 | 1/2004 | Uhlig et al. |
| 2004/0005370 | A1 | 1/2004 | Breton |
| 2004/0009180 | A1 | 1/2004 | Donovan |
| 2004/0009936 | A1 | 1/2004 | Tang et al. |
| 2004/0028635 | A1 | 2/2004 | Chauvierre et al. |
| 2004/0033202 | A1 | 2/2004 | Cooper et al. |
| 2004/0033241 | A1 | 2/2004 | Donovan |
| 2004/0037853 | A1 | 2/2004 | Borodic |
| 2004/0043026 | A1 | 3/2004 | Tuan et al. |
| 2004/0048836 | A1 | 3/2004 | Wilmott |
| 2004/0081688 | A1 | 4/2004 | Del Curto et al. |
| 2004/0106904 | A1 | 6/2004 | Gonnelli et al. |
| 2004/0115159 | A1 | 6/2004 | Tadlock et al. |
| 2004/0115727 | A1 | 6/2004 | Steward et al. |
| 2004/0116512 | A1 | 6/2004 | Naguib et al. |
| 2004/0126397 | A1 | 7/2004 | Aoki et al. |
| 2004/0127661 | A1 | 7/2004 | Kaspar et al. |
| 2004/0132667 | A1 | 7/2004 | Lintner |
| 2004/0151741 | A1 | 8/2004 | Borodic |
| 2004/0186419 | A1 | 9/2004 | Cho |
| 2004/0191330 | A1 | 9/2004 | Keefe et al. |
| 2004/0229038 | A1 | 11/2004 | Cooper et al. |
| 2004/0235770 | A1 | 11/2004 | Davis et al. |
| 2004/0258701 | A1 | 12/2004 | Dominowski et al. |
| 2004/0258747 | A1 | 12/2004 | Ponzoni et al. |
| 2004/0258758 | A1 | 12/2004 | Gustow et al. |
| 2005/0036966 | A1 | 2/2005 | Heckmann |
| 2005/0038096 | A1 | 2/2005 | Chow et al. |

(56) References Cited

U.S. PATENT DOCUMENTS

| | | |
|---|---|---|
| 2005/0048088 A1 | 3/2005 | Zulli et al. |
| 2005/0065090 A1 | 3/2005 | Ludin et al. |
| 2005/0074461 A1 | 4/2005 | Donovan |
| 2005/0074466 A1 | 4/2005 | Suskind et al. |
| 2005/0079131 A1 | 4/2005 | Lanza et al. |
| 2005/0079228 A1 | 4/2005 | Jaiswal et al. |
| 2005/0096340 A1 | 5/2005 | Zhang et al. |
| 2005/0118254 A1 | 6/2005 | Choi et al. |
| 2005/0123897 A1 | 6/2005 | Cevc et al. |
| 2005/0124378 A1 | 6/2005 | Griffith et al. |
| 2005/0136024 A1 | 6/2005 | Stockel |
| 2005/0142150 A1 | 6/2005 | Graham |
| 2005/0147626 A1 | 7/2005 | Blumenfeld |
| 2005/0147688 A1 | 7/2005 | Russell |
| 2005/0152923 A1 | 7/2005 | Brin et al. |
| 2005/0175636 A1 | 8/2005 | Donovan |
| 2005/0184275 A1 | 8/2005 | Mora-Gutierrez et al. |
| 2005/0196414 A1 | 9/2005 | Dake et al. |
| 2005/0196416 A1 | 9/2005 | Kipp et al. |
| 2005/0208083 A1 | 9/2005 | Annis |
| 2005/0209565 A1 | 9/2005 | Yuzhakov et al. |
| 2005/0214325 A1 | 9/2005 | David |
| 2005/0214378 A1 | 9/2005 | Hoarau et al. |
| 2005/0226842 A1 | 10/2005 | Douin et al. |
| 2005/0238668 A1 | 10/2005 | Wang et al. |
| 2005/0249686 A1 | 11/2005 | Pataut et al. |
| 2005/0261632 A1 | 11/2005 | Xu |
| 2006/0018931 A1 | 1/2006 | Taylor |
| 2006/0057165 A1 | 3/2006 | Dimitrakoudis et al. |
| 2006/0058369 A1 | 3/2006 | Vaughan et al. |
| 2006/0069055 A1 | 3/2006 | Dajee et al. |
| 2006/0069069 A1 | 3/2006 | Kajander et al. |
| 2006/0073208 A1 | 4/2006 | First |
| 2006/0084353 A1 | 4/2006 | Wong et al. |
| 2006/0093624 A1 | 5/2006 | Graham |
| 2006/0099227 A1 | 5/2006 | Hunt |
| 2006/0153876 A1 | 7/2006 | Sanders |
| 2006/0153877 A1 | 7/2006 | Kozaki et al. |
| 2006/0165657 A1 | 7/2006 | Bernasconi et al. |
| 2006/0182767 A1 | 8/2006 | Borodic |
| 2006/0182794 A1 | 8/2006 | Modi |
| 2006/0188525 A1 | 8/2006 | Donovan |
| 2007/0009555 A1 | 1/2007 | Borodic |
| 2007/0026019 A1 | 2/2007 | Hunt |
| 2007/0036831 A1 | 2/2007 | Baker |
| 2007/0104743 A1 | 5/2007 | Lehtola et al. |
| 2007/0116723 A1 | 5/2007 | Coleman |
| 2007/0148194 A1 | 6/2007 | Amiji et al. |
| 2007/0178121 A1 | 8/2007 | First et al. |
| 2007/0203164 A1 | 8/2007 | Chiang et al. |
| 2007/0253911 A1 | 11/2007 | Tamarkin et al. |
| 2007/0259391 A1 | 11/2007 | Edelson |
| 2007/0270732 A1 | 11/2007 | Levin |
| 2007/0287733 A1 | 12/2007 | Snorrason |
| 2007/0292359 A1 | 12/2007 | Friedman et al. |
| 2008/0050352 A1 | 2/2008 | Webb et al. |
| 2008/0081049 A1 | 4/2008 | Sanders |
| 2008/0102089 A1 | 5/2008 | Cappello |
| 2008/0108570 A1 | 5/2008 | Hunt |
| 2008/0138336 A1 | 6/2008 | Damschroder et al. |
| 2008/0206155 A1 | 8/2008 | Tamarkin et al. |
| 2008/0207737 A1 | 8/2008 | Zinger |
| 2008/0220021 A1 | 9/2008 | Modi |
| 2008/0274195 A1 | 11/2008 | Nicolosi et al. |
| 2009/0010884 A1 | 1/2009 | Chang et al. |
| 2009/0041680 A1 | 2/2009 | Tamarkin et al. |
| 2009/0238865 A1 | 9/2009 | Heurtault et al. |
| 2009/0291095 A1 | 11/2009 | Baker, Jr. et al. |
| 2009/0306198 A1 | 12/2009 | Nicolosi et al. |
| 2010/0040883 A1 | 2/2010 | McCarthy et al. |
| 2010/0049672 A1 | 2/2010 | Straube et al. |
| 2010/0062415 A1 | 3/2010 | Schwoebel et al. |
| 2010/0137357 A1 | 6/2010 | Koleng et al. |
| 2010/0150994 A1 | 6/2010 | Kotyla |
| 2010/0168023 A1 | 7/2010 | Ruegg et al. |
| 2010/0172943 A1 | 7/2010 | Edelson et al. |
| 2010/0183726 A1 | 7/2010 | Nicolosi et al. |
| 2010/0196445 A1 | 8/2010 | David et al. |
| 2010/0233251 A1 | 9/2010 | Von Andrian et al. |
| 2010/0280975 A1 | 11/2010 | Wischik et al. |
| 2011/0020227 A1 | 1/2011 | McCarthy et al. |
| 2011/0206736 A1 | 8/2011 | Waldman et al. |
| 2011/0206739 A1 | 8/2011 | Nicolosi et al. |
| 2011/0212157 A1 | 9/2011 | Edelson et al. |
| 2011/0213219 A1 | 9/2011 | Bilello et al. |
| 2011/0213335 A1 | 9/2011 | Burton et al. |
| 2011/0305734 A1 | 12/2011 | Edelson et al. |
| 2011/0305735 A1 | 12/2011 | Cebrian Puche et al. |
| 2012/0064136 A1 | 3/2012 | Baker, Jr. et al. |
| 2012/0107349 A1 | 5/2012 | Baker, Jr. et al. |
| 2012/0156258 A1 | 6/2012 | Tokumoto et al. |
| 2012/0164182 A1 | 6/2012 | Edelson et al. |
| 2012/0208858 A1 | 8/2012 | Shanler et al. |
| 2012/0231034 A1 | 9/2012 | Shaari |
| 2012/0321571 A1 | 12/2012 | Edelson et al. |
| 2012/0321579 A1 | 12/2012 | Edelson et al. |
| 2012/0328525 A1 | 12/2012 | Edelson et al. |
| 2012/0328549 A1 | 12/2012 | Edelson et al. |
| 2012/0328701 A1 | 12/2012 | Edelson et al. |
| 2012/0328702 A1 | 12/2012 | Edelson et al. |
| 2013/0045238 A1 | 2/2013 | Chow et al. |
| 2013/0078295 A1 | 3/2013 | Cebrian Puche et al. |
| 2013/0224245 A1 | 8/2013 | Kommareddy et al. |
| 2013/0251770 A1 | 9/2013 | Waugh et al. |
| 2014/0017331 A1 | 1/2014 | McCarthy et al. |
| 2014/0099342 A1 | 4/2014 | Edelson et al. |
| 2014/0199300 A1 | 7/2014 | Besret et al. |
| 2014/0234382 A1 | 8/2014 | Edelson et al. |
| 2014/0294964 A1 | 10/2014 | Nicolosi et al. |
| 2014/0378384 A1 | 12/2014 | Xu et al. |
| 2015/0037402 A1 | 2/2015 | Chancellor et al. |
| 2015/0132282 A1 | 5/2015 | Finzi et al. |
| 2015/0196490 A1 | 7/2015 | Edelson et al. |
| 2015/0313536 A1 | 11/2015 | Edelson |
| 2015/0313819 A1 | 11/2015 | Edelson |
| 2015/0335574 A1 | 11/2015 | Nicolosi et al. |
| 2016/0081901 A1 | 3/2016 | Yang et al. |
| 2016/0144001 A1 | 5/2016 | Vaughan et al. |
| 2016/0213757 A1 | 7/2016 | Edelson et al. |
| 2017/0079895 A1 | 3/2017 | Edelson et al. |
| 2017/0087088 A1 | 3/2017 | Edelson et al. |
| 2017/0157020 A1 | 6/2017 | Waugh et al. |
| 2017/0181952 A1 | 6/2017 | Edelson et al. |
| 2017/0209553 A1 | 7/2017 | Kaspar et al. |
| 2017/0290773 A1 | 10/2017 | Chancellor et al. |
| 2017/0312210 A1 | 11/2017 | Edelson et al. |
| 2017/0333432 A1 | 11/2017 | Sinclair |
| 2017/0361130 A9 | 12/2017 | Modi |
| 2019/0183785 A1 | 6/2019 | Edelson et al. |
| 2019/0298654 A1 | 10/2019 | Kotyla |
| 2019/0343773 A1 | 11/2019 | Edelson |
| 2020/0054722 A1 | 2/2020 | Edelson |
| 2020/0214961 A1 | 7/2020 | Edelson et al. |
| 2021/0220271 A1 | 7/2021 | Kotyla |
| 2021/0301289 A1 | 9/2021 | Kaspar et al. |
| 2021/0308021 A1 | 10/2021 | Edelson et al. |
| 2022/0031595 A1 | 2/2022 | Edelson |
| 2022/0054389 A1 | 2/2022 | Edelson et al. |
| 2022/0105068 A1 | 4/2022 | Edelson |
| 2022/0218623 A1 | 7/2022 | Edelson |
| 2022/0296503 A1 | 9/2022 | Edelson |
| 2022/0387299 A1 | 12/2022 | Edelson et al. |

FOREIGN PATENT DOCUMENTS

| | | |
|---|---|---|
| CA | 2442660 A1 | 10/2002 |
| CA | 2465123 A1 | 5/2003 |
| CA | 2543722 A1 | 5/2005 |
| CA | 2554052 A1 | 8/2005 |
| CA | 2585259 A1 | 5/2006 |
| CA | 2494473 C | 6/2007 |
| CA | 2631927 A1 | 4/2008 |
| CA | 2688415 A1 | 12/2008 |
| CN | 1130868 A | 9/1996 |

(56) References Cited

FOREIGN PATENT DOCUMENTS

| | | | |
|---------|--------|---|------|
| CN | 1237151 | A | 12/1999 |
| CN | 1316906 | A | 10/2001 |
| CN | 1946431 | A | 4/2007 |
| CN | 101374498 | A | 2/2009 |
| CN | 101588792 | A | 11/2009 |
| CN | 101765423 | A | 6/2010 |
| CN | 101848702 | A | 9/2010 |
| CN | 101917959 | A | 12/2010 |
| CN | 102076333 | A | 5/2011 |
| CN | 102458473 | A | 5/2012 |
| CN | 103096921 | A | 5/2013 |
| CN | 104147591 | A | 11/2014 |
| CN | 105147608 | A | 12/2015 |
| CN | 107320841 | A | 11/2017 |
| CN | 109069608 | A | 12/2018 |
| CN | 109414575 | A | 3/2019 |
| DE | 102004016710 | A1 | 10/2005 |
| DE | 102006046076 | A1 | 4/2007 |
| EP | 0315079 | A1 | 5/1989 |
| EP | 0406162 | A2 | 1/1991 |
| EP | 0572080 | B1 | 11/1995 |
| EP | 0696452 | A1 | 2/1996 |
| EP | 1080720 | A1 | 3/2001 |
| EP | 0770422 | B1 | 9/2002 |
| EP | 1334729 | A1 | 8/2003 |
| EP | 1430906 | A2 | 6/2004 |
| EP | 1502601 | A1 | 2/2005 |
| EP | 1586336 | A1 | 10/2005 |
| EP | 1652515 | A1 | 5/2006 |
| EP | 1249232 | B1 | 10/2006 |
| EP | 1784163 | A1 | 5/2007 |
| EP | 1345597 | B1 | 10/2007 |
| EP | 1917976 | A1 | 5/2008 |
| EP | 2272822 | A1 | 1/2011 |
| EP | 1651162 | B1 | 10/2015 |
| EP | 2 990 057 | A1 | 3/2016 |
| EP | 3689331 | A1 | 8/2020 |
| FR | 2849375 | A1 | 7/2004 |
| JP | 1990000203 | | 1/1990 |
| JP | H02-203 | A | 1/1990 |
| JP | H04-198122 | A | 7/1992 |
| JP | H04-198123 | A | 7/1992 |
| JP | H04-202122 | A | 7/1992 |
| JP | H04351623 | A | 12/1992 |
| JP | H07-285863 | A | 10/1995 |
| JP | H08-507515 | A | 8/1996 |
| JP | H10-114648 | A | 5/1998 |
| JP | 2001513331 | A | 9/2001 |
| JP | 2002-534448 | A | 10/2002 |
| JP | 2002308728 | A | 10/2002 |
| JP | 2003-525257 | A | 8/2003 |
| JP | 2003527411 | A | 9/2003 |
| JP | 2004519447 | A | 7/2004 |
| JP | 2004532214 | A | 10/2004 |
| JP | 2004/538310 | A | 12/2004 |
| JP | 2005-507888 | A | 3/2005 |
| JP | 2005-538082 | A | 12/2005 |
| JP | 2006273821 | A | 10/2006 |
| JP | 2007-169301 | A | 7/2007 |
| JP | 2007-517890 | A | 7/2007 |
| JP | 2007-519745 | A | 7/2007 |
| JP | 2007-523689 | A | 8/2007 |
| JP | 2007/530544 | A | 11/2007 |
| JP | 2008/511627 | A | 4/2008 |
| JP | 2008/514353 | A | 5/2008 |
| JP | 2008-517890 | A | 5/2008 |
| JP | 2008-531732 | A | 8/2008 |
| JP | 2008-543833 | A | 12/2008 |
| JP | 2009-518307 | A | 5/2009 |
| JP | 2010-502268 | A | 1/2010 |
| JP | 2010-513363 | A | 4/2010 |
| JP | 2010-528981 | A | 8/2010 |
| JP | 2010-531298 | A | 9/2010 |
| JP | 2012-514003 | A | 6/2012 |
| JP | 2020-002136 | A | 1/2020 |
| KR | 2002-0079150 | A | 10/2002 |
| KR | 10-2004-0062602 | A | 7/2004 |
| KR | 2009-0106493 | A | 10/2009 |
| KR | 10-2012-0102569 | A | 9/2012 |
| TW | 2008/14998 | A | 4/2008 |
| TW | 2011/17810 | A | 6/2011 |
| WO | WO-90/11364 | A1 | 10/1990 |
| WO | WO-93/18752 | A1 | 9/1993 |
| WO | WO-1994/00481 | A1 | 1/1994 |
| WO | WO-94/20072 | A1 | 9/1994 |
| WO | WO-95/22973 | A1 | 8/1995 |
| WO | WO-95/35157 | A1 | 12/1995 |
| WO | WO-96/23409 | A1 | 8/1996 |
| WO | WO-96/39167 | A1 | 12/1996 |
| WO | WO-98/20834 | A2 | 5/1998 |
| WO | WO-98/51278 | A2 | 11/1998 |
| WO | WO-99/07238 | A2 | 2/1999 |
| WO | WO-99/27918 | A1 | 6/1999 |
| WO | WO-99/44594 | A1 | 9/1999 |
| WO | WO-00/07621 | A2 | 2/2000 |
| WO | WO-00/15245 | A2 | 3/2000 |
| WO | WO-00/38653 | A1 | 7/2000 |
| WO | WO-00/41528 | A2 | 7/2000 |
| WO | WO-00/74658 | A1 | 12/2000 |
| WO | WO-01/10413 | A1 | 2/2001 |
| WO | WO-01/064328 | A1 | 9/2001 |
| WO | WO-01/70197 | A2 | 9/2001 |
| WO | WO-01/88019 | A1 | 11/2001 |
| WO | WO-02/39979 | A1 | 5/2002 |
| WO | WO-02/051390 | A2 | 7/2002 |
| WO | WO-02/056866 | A1 | 7/2002 |
| WO | WO-02/064112 | A2 | 8/2002 |
| WO | WO-02/076441 | A1 | 10/2002 |
| WO | WO-02/080864 | A1 | 10/2002 |
| WO | WO-2003/000243 | A1 | 1/2003 |
| WO | WO-03/011333 | A1 | 2/2003 |
| WO | WO-03/037933 | A2 | 5/2003 |
| WO | WO-2003/071267 | A1 | 8/2003 |
| WO | WO-03/092585 | A2 | 11/2003 |
| WO | WO-03/101483 | A1 | 12/2003 |
| WO | WO-2004/006954 | A2 | 1/2004 |
| WO | WO-2004/041155 | A2 | 5/2004 |
| WO | WO-2004/076634 | A2 | 9/2004 |
| WO | WO-2004/084839 | A2 | 10/2004 |
| WO | WO-2004/103272 | A2 | 12/2004 |
| WO | WO-2005/007225 | A1 | 1/2005 |
| WO | WO-2005/013938 | A1 | 2/2005 |
| WO | WO-2005/020962 | A1 | 3/2005 |
| WO | WO-2005/023282 | A1 | 3/2005 |
| WO | WO-2005/027872 | A2 | 3/2005 |
| WO | WO-2005/042539 | A1 | 5/2005 |
| WO | WO-2005/058370 | A1 | 6/2005 |
| WO | WO-2005/063377 | A1 | 7/2005 |
| WO | WO-2005/070394 | A2 | 8/2005 |
| WO | WO-2005/074894 | A1 | 8/2005 |
| WO | WO-2005/082514 | A2 | 9/2005 |
| WO | WO-2005/084361 | A2 | 9/2005 |
| WO | WO-2005/084410 | A2 | 9/2005 |
| WO | WO-2005/091991 | A2 | 10/2005 |
| WO | WO-2005/102285 | A1 | 11/2005 |
| WO | WO-2006/005910 | A2 | 1/2006 |
| WO | WO-2006/018024 | A2 | 2/2006 |
| WO | WO-2006/025976 | A1 | 3/2006 |
| WO | WO-2006/028339 | A1 | 3/2006 |
| WO | WO-2006/039014 | A1 | 4/2006 |
| WO | WO-2006/045170 | A2 | 5/2006 |
| WO | WO-2006/050926 | A2 | 5/2006 |
| WO | WO-2006/084353 | A1 | 8/2006 |
| WO | WO-2006/094263 | A2 | 9/2006 |
| WO | WO-2006/123354 | A2 | 11/2006 |
| WO | WO-2006/138059 | A2 | 12/2006 |
| WO | WO-2006/138127 | A2 | 12/2006 |
| WO | WO-2007/046102 | A2 | 4/2007 |
| WO | WO-2007041664 | A1 | 4/2007 |
| WO | WO-2007/089454 | A2 | 8/2007 |
| WO | WO-2007/098057 | A2 | 8/2007 |
| WO | WO-2007/103555 | A2 | 9/2007 |
| WO | WO-2007/146712 | A2 | 12/2007 |
| WO | WO-2007/149868 | A2 | 12/2007 |

(56)            References Cited

FOREIGN PATENT DOCUMENTS

| WO | WO-2008/010788 A2 | 1/2008 |
|----|-------------------|--------|
| WO | WO-2008/038147 A2 | 4/2008 |
| WO | WO-2008/045107 A2 | 4/2008 |
| WO | WO-2008/054362 A2 | 5/2008 |
| WO | WO-2008/070538 A2 | 6/2008 |
| WO | WO-2008/074885 A2 | 6/2008 |
| WO | WO-2008/077641 A1 | 7/2008 |
| WO | WO-2008/140594 A2 | 11/2008 |
| WO | WO-2008/151022 A2 | 12/2008 |
| WO | WO-2008/156446 A1 | 12/2008 |
| WO | WO-2008/156646 A1 | 12/2008 |
| WO | WO-2009/073569 A2 | 6/2009 |
| WO | WO-2009/123241 A1 | 10/2009 |
| WO | WO-2009/144037 A1 | 12/2009 |
| WO | WO-2009/158687 A1 | 12/2009 |
| WO | WO-2010/040271 A1 | 4/2010 |
| WO | WO-2010/056922 A2 | 5/2010 |
| WO | WO-2010/078242 A1 | 7/2010 |
| WO | WO-2010/087964 A2 | 8/2010 |
| WO | WO-2010/128087 A2 | 11/2010 |
| WO | WO-2010/148572 A1 | 12/2010 |
| WO | WO-2010/151840 A2 | 12/2010 |
| WO | WO-2011/041483 A2 | 4/2011 |
| WO | WO-2011/041718 A2 | 4/2011 |
| WO | WO-2011/050180 A1 | 4/2011 |
| WO | WO-2012/103035 A1 | 8/2012 |
| WO | WO-2012/103039 A1 | 8/2012 |
| WO | WO-2012103038 A2 | 8/2012 |
| WO | WO-2013/013042 A1 | 1/2013 |
| WO | WO-2013/097704 A1 | 7/2013 |
| WO | WO-2014/186134 A1 | 11/2014 |
| WO | WO-2015/020982 A2 | 2/2015 |
| WO | WO-2016/065426 A1 | 5/2016 |
| WO | WO-2017/075468 A1 | 5/2017 |
| WO | WO-2018/093465 A1 | 5/2018 |
| WO | WO-2020/056160 A1 | 3/2020 |
| WO | WO-2020/056191 A1 | 3/2020 |
| WO | WO-2020/117564 A1 | 6/2020 |
| WO | WO-2020/231983 A1 | 11/2020 |

OTHER PUBLICATIONS

Bauerova et al., Chemical enhancers for transdermal drug transport, European J Drug Metabolism and Pharmacokinetics 26(1/2):85-94 (2001).

Bhartiya et al., Enhanced Wound Healing in Animal Models by Interferon and an Interferon Inducer, J Cell Physiol 150:312-319 (1992).

Bos and Meinardi, The 500 Dalton rule for the skin penetration of chemical compounds and drugs, Exp Dermatol 9:165-169 (2000).

Brewster, Delivering Anti-aging Actives, Cosmetics and Toiletries, 120(6):30, 32-34 (2005).

Cappel et al., Effect of Nanoparticles on Transdermal Drug Delivery, J. Microencapsulation, (3):369-374, 1991.

Carruthers et al., Botulinum A exotoxin use in clinical dermatology, J. Am. Acad. Dermatol. 34(5):788 (1996).

CAS Registry No. 144-68-3, Zeaxanthin, 5 pages (Nov. 16, 1984).

Chajchir, I. et al., Novel topical BoNTA (CosmeTox, Toxin Type A) cream used to treat hyperfunctional wrinkles of the face, mouth, and neck, Aesthetic Plastic Surgery, 32:715-722 (2008).

Chen et al., Transdermal protein delivery by a coadministered peptide identified via phage display, Nature Biotechnology 24(4):455-459 (2006).

Chien, Y.W., Novel drug delivery systems, Second Edition, Marcel Dekker, Inc., New York, Chapter 7, pp. 301-380 (1992).

Choi et al., Percutaneous Absorption, Fourth Edition Bronaugh and Maibach ed., Taylor and Francis, Boca Ratonm Florida, Index and Table of contents only 155:33 (2005).

Cocconi et al., Treatment of Metastatic Malignant Melanoma with Dacarbazine Plux Tamoxifen, New England J Medicine 327(8):516-23 (1992).

Collins, A. and Nasir, A., Topical Botulinum Toxin, Journal of Clinical Aesthetic Dermatology, 3(3):35-39 (2010).

Croda Inc., Pharmaceutical Technology, 3 pages (2005), Retrieved online: http://www.pharmtech.com/pharmtech/Corporate=Capabilities/Croda-Inc/ArticleStandard/Article/detail/399061.

Dalgleish et al., The characterization of small emulsion droplets made from milk proteins and triglyceride oil, Colloids and Surfaces, 123-124:145-153 (May 15, 1997).

Davis, S. P. et al., Insertion of microneedles into skin: measurement and prediction of insertion force and needle fracture force, Jrnl. Biomech., 37:1155-1163 (2004).

De Campo et al., Five-component food-grade microemulsions: Structural characterization by SANS, J Colloid and Interface Science, 274:251-267 (2004).

De Paiva and Dolly, Light chain of botulinum nerotoxin is active in mammalian motor nerve terminals when delivered via liposomes, FEBS 277(1,2):171-174 (1990).

Delgado-Charro et al., Delivery of a hydrophilic solute through the skin from novel microemulsion systems, Eur J Pharmaceutics and Biopharmaceutics 43[1]:37-42 (1997).

Devani, M. et al., The development and characterization of triglyceride-based 'spontaneous' multiple emulsions, International Journal of Pharmaceutics, 300:76-88 (2005).

Devani, M. et al., The emulsification and solubilisation properties of polyglycolysed oils in self-emulsifying formulations, Journal of Pharmacy and Pharmacology, 56(3):307-316 (2004).

Dittgen et al., Acrylic Polymers, A Review of Pharmaceutical Applications, S. T.P. Pharma Sciences, 7(6):403-437 (1997).

Forster et al., Micellization of Strongly Segregated Block Copolymers, J. Chem. Physics, 104(24):9956-9970, 1996.

Freitas, C. and Muller, R. H., Spray-drying of solid lipid nanoparticles (SLN TM), Eur. J. Pharm. Biopharm., 46(2):145-151 (1998).

Fujinaga, Interaction of Botulinum Toxin With the Epitheliol Barrier, J. Biomedicine and Biotechnology, 2010: Article 974943 (2010).

Galioglu et al., Block/graft copolymer synthesis via eerie salt, Die Angewandte makromolekulare chemie, 19-28 (1994).

Garcion et al., A new generation of anticancer, drug-loaded, colloidal vectors reverses multidrug resistance in glioma and reduces tumor progression in rats, Mol. Cancer Ther., 5(7):1710-1722 (2006).

Gunniss, I., Microfluidics Webinar Series. Principles of Particle Size Reduction and Characterization, 42 pages (Retrieved by Examiner Mar. 24, 2017). URL: http://www.horiba.com/fileadmin/uploads/Scientific/Documents/PSA/Webinar_Slides/TE007.pdf.

Guo, L. et al., Enhanced transcutaneous immunization via dissolving microneedle array loaded with liposome encapsulated antigen and adjuvant, International Journal of Pharmaceutics, 447: 22-30 (2013).

Hamouda, T. et al., A novel surfactant nanoemulsion with broad-spectrum sporicidal activity against *bacillus* species, The Journal of Infectious Diseases, 180:1939-1949 (1999).

Hancock et al., An Antioxidant Formulation that Induces Differentiation of Neuroblastoma in Culture, Neuroscience Research Communications, 33(1): 73-76 (2003).

Hardas, B. and Brin, M.F., Topical botulinum toxin type A, Procedures in Cosmetic Dermatology, Botulinum Toxin, Fourth Edition, Edited by J. Carruthers et al., Chapt 12: 81-84 (2018).

Helene et al., Control of Gene Expression by Triple Helix-Forming Oligonucleotides, Ann N.Y. Acad Sci 660:27-36 (1992).

Helene, The anti-gene strategy: control of gene expression by triplex-forming-oligonucleotides, Anti-Cancer Drug Des 6:569-584 (1991).

Heurtault et al., A Novel Phase Inversion-Based Process for the Preparation of Lipid Nanocarriers, Pharmaceutical Research 19(6):875-880 (2002).

Heymann, W.R. et al., Hyperhidrosis and botulinum toxin: expanding horizons, J. Am. Acad. Dermotal., 59(2):332-333 (2008).

Hickerson et al., SiRNA-Mediated Selective Inhibition of Mutant Keratin mRNAs Responsible for the Skin Disorder Pachyonychia Congenita, Ann. N.Y. Acad. Sci. 1082:56-61 (2006).

Hiraishi Y, Hirobe S, Iioka H, Quan YS, Kamiyama F, Asada H, et al. Development of a novel therapeutic approach using a retinoic acid loaded microneedle patch for seborrheic keratosis treatment and safety study in humans. J Control Release 2013;171:93-103.

(56) References Cited

OTHER PUBLICATIONS

International Search Report for PCT/US2006/026918, 4 pages (Jun. 19, 2008).

International Search Report for PCT/US2006/035343, 1 page (Aug. 15, 2007).

International Search Report for PCT/US2006/046236, 3 pages (Jun. 17, 2008).

International Search Report for PCT/US2007/010253, 2 pages (Mar. 14, 2008).

International Search Report for PCT/US2007/086018, 5 pages (Sep. 17, 2008).

International Search Report for PCT/US2007/086040, 7 pages (Feb. 9, 2010).

International Search Report for PCT/US2008/065329, 5 pages (Mar. 12, 2009).

International Search Report for PCT/US2009/048972, 5 pages (Dec. 1, 2009).

International Search Report for PCT/US2012/022276, 6 pages (Jul. 19, 2012).

International Search Report for PCT/US2012/022277, 4 pages (Jul. 6, 2012).

International Search Report for PCT/US2012/022278, 4 pages (Mar. 23, 2012).

International Search Report for PCT/US2012/022279, 7 pages (Nov. 29, 2012).

International Search Report for PCT/US2012/022280, 4 pages (Apr. 27, 2012).

International Search Report for PCT/US2012/022281, 4 pages (Apr. 24, 2012).

International Search Report for PCT/US2015/028806, 2 pages (Jun. 17, 2015).

International Search Report for PCT/US2017/053333, 5 pages (mailed Jan. 25, 2018).

International Search Report for PCT/US2019/050849, 4 pages (mailed Dec. 10, 2019).

International Search Report for PCT/US2019/050890, 5 pages (mailed Dec. 13, 2019).

International Search Report for PCT/US2019/063351, 5 pages (mailed Mar. 5, 2020).

International Search Report for PCT/US2020/032458, 5 pages (mailed Aug. 17, 2020).

Izquierdo et al., The influence of surfactant mixing ration on nano-emulsion formation by the pit method, J Colloid and Interface Sci. 285:388-394 (2004).

Jiten, I., Pharmaceutical Excipient Encyclopedia, Edited by Japan Pharmaceutical Excipients Council, Yakuji Nippo (Ed.): 123 (1994). English Translation.

Johnson et al., Clostridium botulinum neurotoxins—Applications in Medicine and Potential Agents of Bioterrorism, Clinical Microbiology Newsletter, 27(19):147-151 (2005).

Kakumanu et al., A Nanoemulsion Formulation of Dacarbazine Reduces Tumor Size in a Xenograft Mouse Epidermoid Carcinoma Model Compared to Dacarbazine Suspension, Nanomedicine: NBM 7(3):277-283 (2011).

Kalb et al., Different Substrate Recognition Requirements for cleavage of Synaptobrevin-2 by Clostridium baratii and Clostridium botulinum, Applied and Environmental Microbiology p. 1301-1308, 2011.

Katayama et al., A Pentapeptide from Type I Procollagen Promotes Extracellular Matrix Production, J Biol Chem 268(14):9941-9944 (1993).

Keen et al., Botulinum Toxin A for Hyperkinetic Facial Lines: Results of a Double-Blind, Placebo-Controlled Study, Plastic and Reconstructive Surgery, 94(1):94-9 (1994).

Khare et al., In: Microencapsulation in the Food Industry, editors Gaonkar et al, 151-155 (2014).

Kim YC, Song JM, Lipatov AS, Choi SO, Lee JW, Donis RO, et al. Increased immunogenicity of avian influenza DNA vaccine delivered to the skin using a microneedle patch. Eur J Pharm Biopharm 2012;81:239-47.

Kitson, Drugs Used for Skin Diseases, Published in Dermatologic, Cosmeceutic, and Cosmetic Development Therapeutic and Novel Approaches, Ed Walters and Roberts 11-20 (2008).

Kotyla et al., Increased bioavailability of a transdermal application of a nano-sized emulsion preparation, International Journal of Pharmaceutics 347:144-148 (2008).

Kronberg et al., Preparation and Evaluation of Sterically Stabilized Liposomes: Colloidal Stability, Serum Stability, Macrophage Uptake, and Toxicity, J Pharmaceutical Sciences 79(8):667-671 (1990).

Kuo et al., Nanomulsions of an Anti-Oxidant Synergy Formulation Containing Gamma Tocopherol Have Enhanced Bioavailability and Anti-Inflammatory Properties, Int'l J Pharmaceutics 363:206-213 (2008).

Kwon et al., Enhanced Tumor Accumulation and Prolonged Circulation Time of Micelle forming poly , J. Controlled Release, 29: 17-23, 1994.

Labrafills, Supplementary information on excipients, The Royal Society of Chemistry, 5 pages (2018). URL: <http://www.rsc.org/suppdata/c7/nr/c7nr08488a/c7nr08488a1.pdf> [Retrieved on Jun. 4, 2020].

Langbein, K. et al., Antiwrinkle and antiperspirant effects of botulinum toxin, Biological fear—wars of Century 21, Zhejiang Literary Press, (Jul. 31, 2005). English Translation.

Lee et al., Biomedical Applications of Collagen, Int'l J. of Pharmaceuticals, 221:1-22, 2001.

Lee, S-H. et al., Therapeutic efficacy of autologous platelet-rich plasma and polydeoxyribonucleotide on female pattern hair loss, Wound Repair and Regeneration, 23:30-36 (2015).

Leyden et al., Journal of the American Academy of Dermatology, 49(3): 5200-5210 (2003).

Lin et al., Delivery of plasmid DNA expression vector for keratinocyte growth factor-1 using electroporation to improve cutaneous wound healing in a septic rat model, Wound Repair and Regeneration 14:618-624 (2006).

Ling MH, Chen MC. Dissolving polymer microneedle patches for rapid and efficient transdermal delivery of insulin to diabetic rats. Acta Biomater 2013;9:8952-61.

Liu, W. et al., Preparation of cream and emulsion type cosmetics, Skin Science and Cosmetics Efficacy Evaluation, Chemical Industry Press, p. 46 (Nov. 2004). English Translation, 2 pages.

Ludewig and Hoffmann, Adoptive Immunotherapy Methods and Protocols, Humana Press Inc., NJ 393 (2005).

Lupo, Cosmeceutical Peptides, Dermatologic Surgery 31:832-836 (2005).

Ma et al., Two-Dimensional, Shell-Cross-linked Nanoparticle Arrays, J. Am. Chem. Soc., 123:4627-4628, 2001.

Maher, DNA Triple-Helix Formation: An Approach to Artificial Gene Repressors?, BioEssays 14:807-815 (1992).

Martanto, W. et al., Transdermal Delivery of Insulin Using Microneedles in Vivo, Pharm. Res., 21(6):947-952 (2004).

Mason, T.G. et al., Topical Review; Nanoemulsions: formation, structure, and physical properties, Journal of Physics: Condensed Matter, Institute of Physics Publishing, 18(41):R635-R666 (2006).

McAllister, D. V. et al., Microfabricated needles for transdermal delivery of macromolecules and nanoparticles: Fabrication methods and transport studies, PNAS, 100(24):13755-13760 (2003).

Montecucco et al., Effect of pH on the interaction of botulinum neurotoxins A, B and E with liposomes, Biochem J 259:47-53 (1989).

Morel et al., Incorporation in lipospheres of {D-Trp-6}LHRH, Int'l J Pharmaceutics 105(2):R01-R03 (1994).

Müller, R.H. et al., Solid lipid nanoparticles (SLN) for controlled drug delivery—a review of the state of the art. European Journal of Pharmaceutics and Biopharmaceutics, 50(1):161-77 (2000).

Munster, U. et al., RU 58841-myristate—prodrug development for topical treatment of acne and androgenetic alopecia, Pharmazie, 60:8-12 (2005).

Nakayama, H. et al., Composition and function of base for external agent, Recent Skin External Agent, 1: 149-155, 3: 160-166 (First Edition Publication Jul. 10, 1991). English Translation.

Park, J. et al., Biodegradable polymer microneedles: Fabrication, mechanics and transdermal drug delivery, Journal of Controlled Release, 104(1):51-66 (2005).

(56) References Cited

OTHER PUBLICATIONS

Pearce et al., Pharmacologic Characterization of Botulinum Toxin for Basic Science and Medicine, Toxicon 35(9):1373-1412 (1997).

Pickett, A. and Perrow, K., Formulation composition of botulinum toxins in clinical use, Journal of Drugs in Dermatology, 9(9):1085-1091 (2010).

Pinnamaneni, S. et al., Comparison of oil-in-water emulsions manufactured by microfluidization and homogenization, Pharmazie, 58(8):554-558 (2003).

Poste et al., Lipid Vesicles as Carriers for Introducing Biologically Active Materials into Cells, Methods in cell biology 14:34-35 (1976).

Prausnitz, M. R., Microneedles for transdermal drug delivery, Adv. Drug Deliv. Rev., 56:581-587 (2004).

Preti, et al., Genetic influences on human body odor: from genes to the axillae, J. Invest, Dermatol., 130: 344-345 (2010).

Qin, G. et al., Simultaneous basal-bolus delivery of fast-acting insulin and its significance in diabetes management, Nanomedicine: Nanotechnology, Biology, and Medicine, 8: 221-227 (2012).

Ranieri, G. et al., Defibrotide in the treatment of Rayaud's phenomenon in patients with progressive systemic sclerosis or essential mixed cryoglobulinemia, Current Therapeutic Research, 53(1):48-58 (1993).

Robinson, et al., Topical palmitoyl pentapeptide provides improvement in photoaged human facial skin, Int'l J Cosmetic Science 24:155-160 (2005).

Ruland et al., Influence of Various Penetration Enhancers on the In Vitro Permeation of Amino Acids Across Hairless Mouse Skin, Int'l J of Pharmaceutics, 85:7-17, 1992.

Salopek, B. et al., Measurement and Application of Zeta-Potential, Rudarsko-geolosko-naflni zbomik, 4:147-151 (1992).

Santiago et al., Topical Application of a Peptide Inhibitor of Transforming Growth Factor-B1 Ameliorates Bleomycin-Induced Skin Fibrosis, J Investigative Dermatology 125:450-455 (2005).

Santos-Magalhaes, N.S. et al., Colloidal carriers for benzathine penicillin G: Nanoemulsions and nanocapsules, Intl. Jrnl. Pharm., 208:71-80 (2000).

Sarver et al., Ribozymes as Potential Anti-HIV-1 Therapeutic Agents, Science 247:1222-1225 (1990).

Sato, F. and Yukio, M., Botulinum Toxin and the Management of Spasticity, Jpn J Rehabil Med., 37(7):475-482 (2000).

Saulnier et al., Liquid Crystals and Emulsions in the Formulation of Drug Carriers, Comptes Rendus Chimie, 11(3): 221-228 (2008).

Schantz et al., Properties and use of botulinum toxin and other microbial neurotoxins in medicine, Microbiol. Mol. Biol. Rev., 80-99 (1992).

Schmalfuss, U. et al., Modification of drug penetration into human skin using microemulsions, J Controlled Release 46(3):279-285 (1997).

Schneider, M. et al., Nanoparticles and their interactions with the dermal barrier, Dermatoendocrinol., 4:197-206 (2009).

Shea et al., Efficacy of Vitamin E, Phosphatidyl Choline, and Pyruvate on Buffering Neuronal Degeneration and Oxidative Stress in Cultured Cortical Neurons and in Central Nervous Tissue of Apolipoprotein E-Deficient Mice, Free Radical Biology & Medicine 33:(2):276-282 (2002).

Shirkhanzadeh, M., Microneedles coated with porous calcium phosphate ceramics: Effective vehicles for transdermal delivery of solid trehalose, Jrnl. Mater. Sci. Mater. Med., 16:37-45 (2005).

Shone et al., A 50-kDa fragment from the NH2-terminus of the heavy subunit of *Clostridium botulinum* type A neurotoxin forms channels in lipid vesicles, Eur J Biochem 167:175-180 (1987).

Siwu, F. et al., Effects of Various Agents on the Potency of Botulinum Toxin Type C, Progress in Microbiology and Immunology, 3: Abstract R372, 1 page (1996).

Siwu, F. et al., Stability study of Clostridium botulinum toxin type C, Progress in Microbiology and Immunology, 3(24):6-9 (1996).

Sonoda et al., Effects of Emulsifiers on Crystallization Behavior of Lipid Crystals in Nanometer-Size Oil-in-Water Emulsion Droplets, Crystal Growth & Design, 6(1): 306-312 (2006).

Stolnik et al., Long circulating microparticulate drug carriers, Advanced Drug Delivery Reviews, 16: 195-214, 1995.

Syed, F. et al., Ex vivo evaluation of antifibrotic compounds in skin scarring: EGCG and silencing of PAI-1 independently inhibit growth and induce keloid shrinkage, Laboratory Investigation, 93(8):946-690 (2013).

Tadros et al., Formation and stability of nanoemulsions, Advances in Colloid and Interface Science, 108-109:303-318 (2004).

Tagne et al., Nanoemulsion Preparations of the Anticancer Drug Dacarbazine Significantly Increase its Efficacy in Xenograft Mouse Melanoma Model, Molecular Pharmaceutics 5(6):1055-1063 (2008).

Takano, M., Ointment, Today's Skin External Agent, 6: 163-184 (First Edition Publication May 15, 1981, Second Edition Publication Apr. 20, 1982). English Translation.

Talingting et al., "Onion-Type Micelles from polystyrene-block-poly (2-vinylpyridine) and Poly (2-vinylpyridine)-block-poly(ethylene oxide)", Macromolecules, 32: 1593-1601, 1999.

Tang, H. et al., Theoretical Description of Transdermal Transport of Hydrophilic Permeants: Application to Low-Frequency Sonophoresis, Journal of Pharmaceutical Sciences, 90(5): 545-568 (2001).

The Harley Medical Group, Excessive Sweating—Causes and Treatment, <http://www.harleymedical.co.uk/non-surgical-solutions/causes/excessive-sweating/> 1 page [last accessed Aug. 26, 2013].

Trotta et al., Elastic Liposomes for Skin Delivery of Dipotassium Glycyrrhizinate, Int'l J Pharmaceutics 241:319-327 (2002).

Verbaan FJ, Bal SM, van den Berg DJ, Groenink WH, Verpoorten H, Luttge R, et al. Assembled microneedle arrays enhance the transport of compounds varying over a large range of molecular weight across human dermatomed skin. J Control Release 2007;117:238-45.

Verma et al., Particle size of liposomes influences dermal delivery of substances into skin, Int'l J Pharmaceutics 141-151 (2003).

Wang et al., Enhancing effect of Labrafac Lipophile WL 1349 on oral bioavailability of hydroxysafflor yellow A in rats, International Journal of Pharmaceutics 358:198-204 (2008).

Written Opinion for PCT/20US19/063351, 9 pages (mailed Mar. 5, 2020).

Written Opinion for PCT/US2006/026918, 8 pages (Jun. 19, 2008).

Written Opinion for PCT/US2006/035343, 4 pages (Aug. 15, 2007).

Written Opinion for PCT/US2006/046236, 12 pages (Jun. 17, 2008).

Written Opinion for PCT/US2007/010253, 4 pages (Mar. 14, 2008).

Written Opinion for PCT/US2007/086018, 6 pages (Sep. 17, 2008).

Written Opinion for PCT/US2007/086040, 12 pages (Feb. 9, 2010).

Written Opinion for PCT/US2008/065329, 7 pages (Mar. 12, 2009).

Written Opinion for PCT/US2009/048972, 5 pages (Dec. 1, 2009).

Written Opinion for PCT/US2012/022276, 9 pages (Jul. 19, 2012).

Written Opinion for PCT/US2012/022277, 6 pages (Jul. 6, 2012).

Written Opinion for PCT/US2012/022278, 7 pages (Mar. 23, 2012).

Written Opinion for PCT/US2012/022279, 7 pages (Nov. 29, 2012).

Written Opinion for PCT/US2012/022280, 7 pages (Apr. 27, 2012).

Written Opinion for PCT/US2012/022281, 6 pages (Apr. 24, 2012).

Written Opinion for PCT/US2015/028806, 7 pages (Jun. 17, 2015).

Written Opinion for PCT/US2017/053333, 5 pages (mailed Jan. 25, 2018).

Written Opinion for PCT/US2019/050849, 7 pages (mailed Dec. 10, 2019).

Written Opinion for PCT/US2019/050890, 11 pages (mailed Dec. 13, 2019).

Written Opinion for PCT/US2020/032458, 7 pages (mailed Aug. 17, 2020).

Wu et al., Effects of pretreatment of needle puncture and sandpaper abrasion on the in vitro skin permeation of fluorescein isothiocyanate (FITC)-dextran, Int. J. Pharm., 2006:316:102-8.

Wu et al., Topical Transfection Using Plasmid DNA in a Water-in-Oil Nanoemulsion, Int J Pharmaceutics 221(1/02):23-34 (2001).

Wu et al., Topical Transport of Hydrophilic Compounds Using Water-in-Oil Nanoemulsions, Int. J. Pharmaceutics, 220:63-75 (2001).

Yan, S. et al., Microemulsion cosmetics, Cosmetics Science Book II, Science and Technology Literature Press, p. 321 (Oct. 1998). English Translation, 3 pages.

Yu, S. et al., Biological warfare prevention medicine, p. 339 (Sep. 1986).

(56)            References Cited

OTHER PUBLICATIONS

Zahn, J. D. et al., Continuous On-Chip Micropumping for Microneedle Enhanced Drug Delivery, Biomed. Microdev., 6(3):183-190 (2004).

Zhang and Liu, Study on the Formation and Properties of Liquid Crystal Emulsion in Cosmetic, Journal of Cosmetics, Dermatological Sciences and Applications, 3:139-144 (2013).

Gupta, J. et al., Kinetics of skin resealing after insertion of microneedles in human subjects, Jrnl. Controlled Release, 154:148-155 (2011).

Khan, B. A. et al., Basics of pharmaceutical emulsions: A review, African Jrnl. Pharm. Pharmacol., 5(25):2715-2725 (2011).

Oh, J-H. et al., Influence of the delivery systems using a microneedle array on the permeation of a hydrophilic molecule, calcein, Euro. Jrnl. Pharm. Biopharm., 69:1040-1045 (2008).

Placencio, V. R. et al., Small Molecule Inhibitors of Plasminogen Activator Inhibitor-1 Elicit Anti-Tumorigenic and Anti-Angiogenic Activity, PLoS One, 1-18 (2015).

Sugino, M. et al., Ski Permeation and Transdermal Delivery Systems of Drugs: History to Overcome Barrier Function in the Stratum Corneum, Yakugaku Zasshi, 129(12):1453-1458 (2009).

Yamaoka, N. et al., Identification of novel plasminogen activator inhibitor-1 inhibitors with improved oral bioavailability: Structure optimization of N-acylanthranilic acid derivatives, Bioorg. Med. Chem. Lett., 28:809-813 (2018).

Yan, G. et al., Evaluation needle length and density of microneedle arrays in the pretreatment of skin for transdermal drug delivery, Inter. Jrnl. Pharm., 391:7-12 (2010).

Patzelt, and Lademann, The Increasing Importance of the Hair Follicle Route in Dermal and Transdermal Drug Delivery, Chapter 5 in Percutaenous Penetration Enhances Chemical Methods in Penetration Enhancemen, 43-53 (2015).

Kavanagh, G. M. and Shams, K., Botulinum toxin type A by iontophoresis for primary palmar hyperhidrosis, J. Am. Acad. Dermatol., 55:S115-7 (2006).

Lowe, N. J. et al., Botulinum toxin type A in the treatment of primary axillary hyperhidrosis: A 52-week multicenter double blind, randomized, placebo-controlled study of efficacy and safety, J. Am. Acad. Derma., 56(4):604-11 (2007).

Alster, T. S. and Graham, P. M., Microneedling: A Review and Practical Guide, Derm. Surg., 1-8 (2017).

Liu, S. et al., Peptide delivery with poly(ethylene glycol) diacrylate microneedles through swelling effect, Bioengine. Traslat. Med., 2:258-267 (2017).

Boe, A. E. et al., Plasminogen Activator Inhibitor-1 Antagonist TM5441 Attenuates Nw-Nitro-L-Arginine Methyl Ester-Induced Hypertension and Vascular Senescence, Circulation, 128(21):2318-2324 (2013).

Sashin, D., Premature Graying: Reasons, Options, Online Article, WebMD, 2 Pages (2024). <https://www.webmd.com/beauty/features/abcs-premature-graying>.

Zhang, S. et al., Enhanced delivery of hydrophilic peptides in vitro by transdermal microneedle pretreatment, Acta Pharm. Sinica B, 4(1):100-104 (2014).

Zhu, Y. et al., The Achilles' heel of senescent cells: from transcriptome to senolytic drugs, Aging Cell, 14: 644-658 (2015).

* cited by examiner

USES OF PLASMINOGEN ACTIVATOR INHIBITOR 1 (PAI-1) INHIBITORS

CROSS-REFERENCE TO RELATED APPLICATIONS

This application claims priority to U.S. Provisional Application No. 62/731,076, filed Sep. 13, 2018, the entirety of which is incorporated herein by reference.

BACKGROUND

Hair loss or alopecia often promote significant anxiety; many people go to great lengths to re-grow their hair, particularly if hair loss occurs prematurely. Previously available therapies have largely proven unsatisfactory, hence new treatment options are needed.

SUMMARY

The present disclosures provides, inter alia, new technologies (e.g., methods, kits, compositions, etc) for treatment and/or prevention of certain types of alopecia (hair loss). Among other things, the present disclosure provides an insight that plasminogen activator inhibitor-1 (PAI-1) inhibitors may be useful in the treatment and/or prevention only of certain types of alopecia, but not for other types of hair loss. Specifically, the present disclosure provides new technologies (e.g., methods, kits, compositions, etc.) which in some embodiments, may be particularly useful in the treatment and/or prevention of specific types of hair loss (or alopecia), including androgenetic alopecia (also called androgenic alopecia), alopecia areata, frontal fibrosing alopecia, and senescent alopecia. Furthermore, the present disclosure provides insight that the new technologies that may not be particularly useful in the treatment and/or prevention of other types of alopecia such as radiation-induced alopecia, chemotherapy-induced alopecia, and alopecia due to chronic discoid lupus erythematosus.

Those skilled in the art are aware that over-expression of PAI-1 is associated with the prevention of the conversion of plasminogen to plasmin which is essential to fibrinolysis, which is the physiological breakdown of blood clots. The present disclosure provides a surprising insight that PAI-1 may also be associated only with certain types of hair loss. The present disclosure provides a surprising insight that provided new technologies (e.g., methods, kits, compositions, etc.) are effective for treatment and/or prevention of certain types of hair loss, including androgenetic alopecia, alopecia areata, frontal fibrosing alopecia, and senescent alopecia. Alternatively or additionally, in some embodiments, the present disclosure provides a surprising insight that provided new technologies utilizing a PAI-1 inhibitor may not be effective for treatment and/or prevention of certain other types of alopecia such as radiation-induced alopecia, chemotherapy-induced alopecia, and alopecia due to chronic discoid lupus erythematosus. Furthermore, in some embodiments, the present disclosure provides a surprising insight that provided new technologies utilizing a PAI-1 inhibitor may be effective for hair re-growth in subjects who have androgenetic alopecia, alopecia areata, frontal fibrosing alopecia, and senescent alopecia.

In some embodiments, the present disclosure provides methods of treating a subject comprising providing a composition that comprises or delivers a plasminogen activator inhibitor-1 (PAI-1) inhibitor; administering the composition to a site of the subject, wherein the site contains or did contain a plurality of hair follicles, each hair follicle optionally comprising a hair disposed therein, so that the PAI-1 inhibitor is delivered to the subject, wherein the subject is suffering from one or more treatable conditions, and wherein the one or more treatable conditions is/are selected from the group consisting of androgenetic alopecia, alopecia areata, frontal fibrosing alopecia, and senescent alopecia.

In some embodiments, the present disclosure provides methods of treating a subject comprising providing a composition that comprises or delivers a plasminogen activator inhibitor-1 (PAI-1) inhibitor; administering the composition to a subject, wherein a site of the subject contains or did contain a plurality of hair follicles, each hair follicle optionally comprising a hair disposed therein, so that the PAI-1 inhibitor is delivered to the subject, wherein the subject is suffering from one or more treatable conditions, and wherein the one or more treatable conditions is/are selected from the group consisting of androgenetic alopecia, alopecia areata, frontal fibrosing alopecia, and senescent alopecia.

In some embodiments, the present disclosure provides methods of preventing the occurrence or progression of one or more conditions in a subject comprising (a) providing a composition that comprises or delivers a plasminogen activator inhibitor-1 (PAI-1) inhibitor; (b) administering the composition topically to a site of the subject, wherein the site is a skin surface that contains or contained a plurality of hair follicles, each optionally comprising a hair disposed therein, wherein the one or more conditions is/are selected from the group consisting of androgenetic alopecia, alopecia areata, frontal fibrosing alopecia senescent alopecia, and combinations thereof; and (c) leaving the composition on the site for a period of time, so that the PAI-1 inhibitor is delivered to the subject.

In some embodiments, the present disclosure provides methods of hair re-growth in a subject comprising providing a composition that comprises or delivers a plasminogen activator inhibitor-1 (PAI-1) inhibitor; administering the composition to a site of the subject, wherein the site contains or did contain a plurality of hair follicles, each hair follicle optionally may or may not be active, so that the PAI-1 inhibitor is delivered to the subject, wherein the subject is suffering from one or more treatable conditions, and wherein the one or more treatable conditions is/are selected from the group consisting of androgenetic alopecia, alopecia areata, frontal fibrosing alopecia, and senescent alopecia.

In some embodiments, the present disclosure provides new technologies for treating and/or preventing the occurrence or progression of certain types of alopecia. In some embodiments, alopecia is or comprises androgenetic alopecia. In some embodiments, alopecia is or comprises alopecia areata. In some embodiments, alopecia is or comprises frontal fibrosing alopecia. In some embodiments, alopecia is or comprises senescent alopecia. In some embodiments, alopecia is not radiation-induced alopecia. In some embodiments, alopecia is not chemotherapy-induced alopecia. In some embodiments, alopecia is not alopecia due to chronic discoid lupus erythematosus.

In some embodiments, the present disclosure provides new technologies for hair re-growth in subjects with certain types of alopecia. In some embodiments, alopecia is or comprises androgenetic alopecia. In some embodiments, alopecia is or comprises alopecia areata. In some embodiments, alopecia is or comprises frontal fibrosing alopecia. In some embodiments, alopecia is or comprises senescent alopecia. In some embodiments, alopecia is not radiation-induced alopecia. In some embodiments, alopecia is not chemotherapy-induced alopecia. In some embodiments, alopecia is not alopecia due to chronic discoid lupus erythematosus.

In some embodiments, the present disclosure provides new compositions that comprise and/or deliver a therapeutically effective amount of a PAI-1 inhibitor. In certain embodiments, the present disclosure provides new compositions that comprise and/or deliver a therapeutically effective amount of a PAI-1 inhibitor and a pharmaceutically acceptable carrier. In some embodiments, a therapeutically effective amount in w/w is about 0.1% to about 5%, about 0.1% to about 10%, about 0.1% to about 15%, about 0.1% to about 20%, or about 1% to about 5%. In some embodiments, a therapeutically effective amount is about 10 mg/day to about 100 mg/day, about 10 mg/day to about 200 mg/day, about 10 mg/day to about 300 mg/day, about 10 mg/day to about 400 mg/day, about 10 mg/day to about 500 mg/day, about 10 mg/day to about 600 mg/day, about 10 mg/day to about 700 mg/day, about 10 mg/day to about 800 mg/day, about 10 mg/day to about 900 mg/day, or about 10 mg/day to about 1000 mg/day.

In some embodiments, a provided new composition is characterized in that, when administered to an animal suffering from or susceptible to at least one of the disclosed types of alopecia, it achieves at least one of: (i) treatment of at least one type of alopecia in an animal; (ii) delay, retardation, or prevention of progression of at least one type of alopecia in an animal. In certain particular embodiments, for example when a type of alopecia is or comprises androgenetic alopecia, alopecia areata, frontal fibrosing alopecia, senescent alopecia and any combination thereof, a provided new composition may be characterized in that, when administered to an animal suffering from or susceptible to at least one type of alopecia as described herein, achieves at least one of: (i) an increase in the number of hairs (e.g., present at and/or near a site of administration); (ii) prevention of hair loss (alopecia) (e.g., present at and/or near a site of administration); (iii) a delayed onset of hair loss of one or more hairs (e.g., present at and/or near a site of administration); and (iv) an increase in the number of hair follicles.

In general, administration of a composition in accordance with the present disclosure may be by any of a variety of routes. In some embodiments, administration is topical. In some embodiments, administration is by injection. In some embodiments, administration is oral.

In some embodiments, administration achieves systemic delivery. In some embodiments, administration achieves local delivery.

In some embodiments administration is or comprises maintaining a composition at or on a site for a period of time. In some embodiments administration is or comprises massaging a composition into a site.

In some embodiments, a composition is maintained at or on a site for a period of time that is at least 1 minute. In some embodiments, a period of time is at least 1 hour. In some embodiments, a period of time is within a range of 1 to 10 minutes. In some embodiments, a period of time is within a range of about 1 to about 10 minutes, about 5 to about 60 minutes, about 5 to about 12 minutes, about 5 to about 15 minutes, or about 15 to about 30 minutes, about 1 to about 12 hours, about 8 to about 12 hours or 12 hours to about 24 hours.

In some embodiments, provided methods of treating a certain type of alopecia may include, removing administered composition (e.g., removing composition that may remain after a period of time) from its site of administration. In some embodiments, such removing is or comprises rinsing or wiping (e.g., using a wipe that, in some embodiments may be wet or, in some embodiments, may be dry).

In some embodiments, a site to which a composition is administered in accordance with the present disclosure may be on a skin surface. In some embodiments, a site is or comprises hair follicles. In some embodiments a site comprises hair. In some embodiments a site is or comprises skin overlying a muscle or muscle group. In some embodiments a site is hairless. In some embodiments a site is on the torso. In some embodiment a site is on the back. In some embodiments a site is on the chest. In some embodiments a site is on the buttocks. In some embodiments a site is on the crotch. In some embodiments a site is on the groin. In some embodiments a site is on the head. In some embodiments a site is on the scalp. In some embodiments a site is on the face. In some embodiments the site is on the neck. In some embodiments a site is on the décolleté. In some embodiments a site is in the armpit. In some embodiments a site is on the axillae. In some embodiments a site is on the hands. In some embodiments a site is on the feet. In some embodiments a site is on the arms. In some embodiments a site is on the legs. In some embodiments a site formerly had hair or hair follicles but no longer has hair or hair follicles. In some embodiments, a site has hair follicles. In some embodiments, hair follicles present at a site have normal structure and/or density. In some embodiments, a site has hair; in some embodiments, such hair is gray but in some embodiments such hair is not gray.

In some embodiments, a PAI-1 inhibitor for use in accordance with the present disclosure, is or comprises a polypeptide, a nucleic acid, a lipid, a carbohydrate, a small molecule, a metal, or a combination thereof. In some embodiments, a PAI-1 inhibitor is or comprises a polymer (e.g., a polypeptide or polynucleotide). In some embodiments, a PAI-1 inhibitor is or comprises an antibody (e.g., an anti-PAI-1 antibody). In some embodiments, a PAI-1 inhibitor is or comprises a nucleic acid (e.g., is an oligonucleotide, such as an antisense oligonucleotide, an siRNA, etc). In some embodiments, a PAI-1 inhibitor is or comprises a small molecule. In some embodiments, a PAI-1 inhibitors is or comprises 5-Chloro-2-{[(2-{[3-(furan-3-yl)phenyl]amino}-2-oxoethoxy)acetyl]amino benzoic acid, 5-Chloro-2-{[{[3-(furan-3-yl)phenyl]amino}(oxo)acetyl]amino} benzoic acid, a benzopyran compound, a butadiene, spironolactone, imidapril, an angiotensin converting enzyme inhibitor (ACEI, e.g., captopril, or enalapril), an angiotensin II receptor antagonist (AIIRA), a defibrotide (a polydeoxyribonucleotide) or any combination thereof. In some embodiments, a PAI-1 inhibitor is or comprises 5-Chloro-2-{[(2-{[3-(furan-3-yl)phenyl]amino}-2-oxoethoxy)acetyl]amino benzoic acid.

In some embodiments, the present disclosure provides and/or utilizes a composition that comprises and/or delivers a PAI-1 inhibitor. In some embodiments, such a composition is or comprises a suspension. In some embodiments, such a composition is or comprises a foam. In some embodiments, such a composition is or comprises an emulsion, e.g., a nanoemulsion. In some embodiments, such a composition is formulated as a suspension, a foam, a lotion, a cream, a gel, an oil, a powder, a liniment, or drops.

In some embodiments, provided methods of treating certain types of alopecia comprises a step of administering a penetrating treatment. In some embodiments, a penetrating treatment is or comprises a non-irritating chemical agent. In some embodiments, a penetrating treatment is or comprises administration of an electric or magnetic field. In some embodiments, a penetrating treatment is or comprises microneedling. In some embodiments, a penetrating treatment is or comprises laser treatment.

In some embodiments, provided technologies aide in PAI-1 inhibitor penetration of site of administration. In some embodiments, a provided PAI-1 inhibitor (e.g., in or from a composition as described herein) penetrates its site of administration within about 1, 2, 3, 4, 5, 6, 7, 8, 9, or 10 minutes of administration. In some embodiments, a provided PAI-1 inhibitor penetrates site of administration within about 5 to about 60 minutes, about 5 to about 12 minutes, about 5 to about 15 minutes, or about 15 to about 30 minutes of administration. In some embodiments, a provided PAI-1 inhibitor penetrates site of administration within about 1, 2, 3, 4, 5, 6, 7, 8, 9, 10, 11, 12 or 24 hours of administration. In some embodiments, a provided PAI-1 inhibitor penetrates site of administration within about 1 to about 12 hours, about 8 to about 12 hours or 12 hours to about 24 hours of administration.

In some embodiments, according to the present disclosure, methods of treatment and/or prevention of certain types of alopecia comprises two or more administrations of a PAI-1 inhibitor composition over time. In some embodiments, administration of two or more administrations of a composition is separated by a specified period of time. In some embodiments, according to the present disclosure, a specified period of time for administering a composition may be longer than a specified period of time for administering a reference treatment regimen.

Disclosed herein, in certain embodiments, are kits comprising compositions that comprise or deliver a PAI-1 inhibitor.

In some embodiments, provided kits comprise a patch. In some embodiments, a patch is arrange, constructed, and/or utilized for administration to cover an administered composition. Alternatively or additionally, in some embodiments, a patch may contain or comprise a composition that comprises and/or delivers a PAI-1 inhibitor. In some embodiments, a patch comprises microneedles.

In some embodiments, provided kits comprise a device for facilitating penetration of a composition into a site on a subject. In some such embodiments, a provided device may be or comprises a brush, a comb, patch, a roller, a pen, etc.

In some embodiments, provided kits comprise instructions for administering a composition as described herein. In some embodiments, the present disclosure provides insight into administering combination therapy and/or treatment to treat or prevent the occurrence of a certain type of alopecia (e.g. androgenetic alopecia, alopecia areata, frontal fibrosing alopecia, senescent alopecia, etc.). In some embodiments, the combination therapy or treatment, comprises administering a PAI-1 inhibitor as described herein in combination with one or more other active agents. In some embodiments, for example certain types of alopecia (e.g. androgenetic alopecia, alopecia areata, frontal fibrosing alopecia, senescent alopecia, etc.) one or more other active agents, wherein the one or more other active agents is selected from the group comprising of minoxidil, finasteride, dutasteride, platelet-rich plasma, cinnamidopropyltrimonium chloride, solid lipid nanoparticles, 1-cystine, 1-methionine, melatonin, pressure therapy, silicone gel sheeting, intra-lesional triamcinolone acetonide (TAC), cryosurgery, radiation, laser therapy, IFN, 5-FU, high doses of oxygen using hyperbaric oxygen therapy (HBOT), cryotherapy, surgical excision, topical agents, Angiotensin II Receptor Antagonists, Angiotensin Converting Enzyme (ACE) Inhibitors, NSAIDs, COX-2 Inhibitors, Analgesics, Low-Dose Corticosteroids, Narcotics, Antacids, H2 Blockers, Proton Pump Inhibitors, Prokinetic Agents, Somatostatin Agonist, Antibiotics, Prostaglandin Derivatives, Treprostinil, Iloprost, Endothelin Receptor Antagonists, IP Receptor Agonist, Phosphosdiesterase type 5 (PDES) inhibitors, Anti-Fibrotic Agent, Tyrosine Kinase Inhibitor, Immunosuppressants, Alkylating agents, Pilocarpine, and combinations thereof. In some embodiments, for example for Raynaud's disease or Raynaud's phenomenon, one or more other active agents is selected from the group comprising of calcium channel blockers, alpha blockers, nitroglycerin, angiotensin II receptor antagonists, selective serotonin reuptake inhibitors, glyceryl trinitrate, tadalafil, *Ginkgo biloba* extract, SLx-2101, St. John's Wort, fasudil, cilostazol, iloprost, relaxin, treprostinil diethanolamine, sildenafil, atorvastatin, imatinib mesylate, treprostinil diethanolamine, and combinations thereof.

Definitions

In this application, unless otherwise clear from context, (i) the term "a" may be understood to mean "at least one"; (ii) the term "or" may be understood to mean "and/or"; (iii) the terms "comprising" and "including" may be understood to encompass itemized components or steps whether presented by themselves or together with one or more additional components or steps; and (iv) the terms "about" and "approximately" may be understood to permit standard variation as would be understood by those of ordinary skill in the art; and (v) where ranges are provided, endpoints are included.

About: The term "about", when used herein in reference to a value, refers to a value that is similar, in context to the referenced value. In general, those skilled in the art, familiar with the context, will appreciate the relevant degree of variance encompassed by "about" in that context. For example, in some embodiments, the term "about" may encompass a range of values that within 25%, 20%, 19%, 18%, 17%, 16%, 15%, 14%, 13%, 12%, 11%, 10%, 9%, 8%, 7%, 6%, 5%, 4%, 3%, 2%, 1%, or less of the referred value.

Administration: As used herein, the term "administration" typically refers to the administration of a composition to a subject or system to achieve delivery of an agent that is, or is included in, the composition. Those of ordinary skill in the art will be aware of a variety of routes that may, in appropriate circumstances, be utilized for administration to a subject, for example a human. For example, in some embodiments, administration may be ocular, oral, parenteral, topical, etc. In some particular embodiments, administration may be bronchial (e.g., by bronchial instillation), buccal, dermal (which may be or comprise, for example, one or more of topical to the dermis, intradermal, interdermal, transdermal, etc), enteral, intra-arterial, intradermal, intragastric, intramedullary, intramuscular, intranasal, intraperitoneal, intrathecal, intravenous, intraventricular, within a specific organ (e. g. intrahepatic), mucosal, nasal, oral, rectal, subcutaneous, sublingual, topical, tracheal (e.g., by intratracheal instillation), vaginal, vitreal, etc. In some embodiments, administration may involve only a single dose. In some embodiments, administration may involve application of a fixed number of doses. In some embodiments, administration may involve dosing that is intermittent (e.g., a plurality of doses separated in time) and/or periodic (e.g., individual doses separated by a common period of time) dosing. In some embodiments, administration may involve continuous dosing (e.g., perfusion) for at least a selected period of time.

Agent: In general, the term "agent", as used herein, may be used to refer to a compound or entity of any chemical class including, for example, a polypeptide, nucleic acid, saccharide, lipid, small molecule, metal, or combination or complex thereof. In appropriate circumstances, as will be clear from context to those skilled in the art, the term may be utilized to refer to an entity that is or comprises a cell or organism, or a fraction, extract, or component thereof. Alternatively or additionally, as context will make clear, the term may be used to refer to a natural product in that it is found in and/or is obtained from nature. In some instances, again as will be clear from context, the term may be used to refer to one or more entities that is man-made in that it is designed, engineered, and/or produced through action of the hand of man and/or is not found in nature. In some embodiments, an agent may be utilized in isolated or pure form; in some embodiments, an agent may be utilized in crude form. In some embodiments, potential agents may be provided as collections or libraries, for example that may be screened to identify or characterize active agents within them. In some cases, the term "agent" may refer to a compound or entity that is or comprises a polymer; in some cases, the term may refer to a compound or entity that comprises one or more polymeric moieties. In some embodiments, the term "agent" may refer to a compound or entity that is not a polymer and/or is substantially free of any polymer and/or of one or more particular polymeric moieties. In some embodiments, the term may refer to a compound or entity that lacks or is substantially free of any polymeric moiety.

Agonist: Those skilled in the art will appreciate that the term "agonist" may be used to refer to an agent condition, or event whose presence, level, degree, type, or form correlates with increased level or activity of another agent (i.e., the agonized agent). In general, an agonist may be or include an agent of any chemical class including, for example, small molecules, polypeptides, nucleic acids, carbohydrates, lipids, metals, and/or any other entity that shows the relevant activating activity. In some embodiments, an agonist may be direct (in which case it exerts its influence directly upon its target); in some embodiments, an agonist may be indirect (in which case it exerts its influence by other than binding to its target; e.g., by interacting with a regulator of the target, so that level or activity of the target is altered).

Antagonist: Those skilled in the art will appreciate that the term "antagonist", as used herein, may be used to refer to an agent condition, or event whose presence, level, degree, type, or form correlates with decreased level or activity of another agent (i.e., the inhibited agent, or target). In general, an antagonist may be or include an agent of any chemical class including, for example, small molecules, polypeptides, nucleic acids, carbohydrates, lipids, metals, and/or any other entity that shows the relevant inhibitory activity. In some embodiments, an antagonist may be direct (in which case it exerts its influence directly upon its target); in some embodiments, an antagonist may be indirect (in which case it exerts its influence by other than binding to its target; e.g., by interacting with a regulator of the target, so that level or activity of the target is altered).

Animal: As used herein refers to any member of the animal kingdom. In some embodiments, "animal" refers to humans, of either sex and at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically engineered animal, and/or a clone.

Biologically active agent: As used herein, the phrase "biologically active agent" refers to any substance that has activity in a biological system and/or organism. For instance, a substance that, when administered to an organism, has a biological effect on that organism is considered to be biologically active. In some embodiments, where a substance (e.g., a polypeptide, nucleic acid, antibody, etc.) is biologically active, a portion of that substance that shares at least one biological activity of the whole substance is typically referred to as a "biologically active" portion.

Carrier: as used herein, refers to a diluent, adjuvant, excipient, or vehicle with which a composition is administered. In some exemplary embodiments, carriers can include sterile liquids, such as, for example, water and oils, including oils of petroleum, animal, vegetable or synthetic origin, such as, for example, peanut oil, soybean oil, mineral oil, sesame oil and the like. In some embodiments, carriers are or include one or more solid components.

Cosmetic formulation: The term "cosmetic formulation" is used herein to refer to a topically applied composition that contains one or more agents having cosmetic properties. To give but a few examples, a cosmetic formulation may be a skin softener, nutrition lotion type emulsion, cleansing lotion, cleansing cream, skin milk, emollient lotion, massage cream, emollient cream, make-up base, lipstick, facial pack or facial gel, cleaner formulation such as shampoos, rinses, body cleanser, hair-tonics, or soaps, and/or a dermatological composition such as a lotion, ointment, gel, cream, patch, deodorant, antiperspirant, and/or spray.

Composition: Those skilled in the art will appreciate that the term "composition", as used herein, may be used to refer to a discrete physical entity that comprises one or more specified components. In general, unless otherwise specified, a composition may be of any form—e.g., gas, gel, liquid, solid, etc.

Comprising: A composition or method described herein as "comprising" one or more named elements or steps is open-ended, meaning that the named elements or steps are essential, but other elements or steps may be added within the scope of the composition or method. To avoid prolixity, it is also understood that any composition or method described as "comprising" (or which "comprises") one or more named elements or steps also describes the corresponding, more limited composition or method "consisting essentially of" (or which "consists essentially of") the same named elements or steps, meaning that the composition or method includes the named essential elements or steps and may also include additional elements or steps that do not materially affect the basic and novel characteristic(s) of the composition or method. It is also understood that any composition or method described herein as "comprising" or "consisting essentially of" one or more named elements or steps also describes the corresponding, more limited, and closed-ended composition or method "consisting of" (or "consists of") the named elements or steps to the exclusion of any other unnamed element or step. In any composition or method disclosed herein, known or disclosed equivalents of any named essential element or step may be substituted for that element or step.

Cream: The term "cream" refers to a spreadable composition, typically formulated for application to the skin. Creams typically contain an oil and/or fatty acid based-matrix. Creams formulated according to the present invention may contain nanoparticles and may be capable of substantially complete penetration (e.g., of such nanoparticles) through the skin upon topical administration. Such a cream could also act as a carrier for incorporated materials (e.g., for example, for one or more known therapeutic agents and/or independently active biologically active agents).

Dispersion medium: The term "dispersion medium" as used herein, refers to a liquid medium in which particles (e.g., empty nanoparticles and/or nanoparticles containing one or more known therapeutic agents and/or independently active biologically active agents) are dispersed. In general, a dispersion is formed when at least two immiscible materials are combined. An "oil-in-water" dispersion is one in which oily particles are dispersed within an aqueous dispersion medium. A "water-in-oil" dispersion is one in which aqueous particles are dispersed within an oily dispersion medium. Those of ordinary skill in the art will appreciate that a dispersion can be formed from any two immiscible media and is not limited strictly to combinations of aqueous and oily media. The term "dispersion medium" therefore applies broadly to any dispersion medium notwithstanding that it is common to refer to "aqueous" and "oily" categories.

Dosage form or unit dosage form: Those skilled in the art will appreciate that the term "dosage form" may be used to refer to a physically discrete unit of an active agent (e.g., a therapeutic or diagnostic agent) for administration to a subject. Typically, each such unit contains a predetermined quantity of active agent. In some embodiments, such quantity is a unit dosage amount (or a whole fraction thereof) appropriate for administration in accordance with a dosing regimen that has been determined to correlate with a desired or beneficial outcome when administered to a relevant population (i.e., with a therapeutic dosing regimen). Those of ordinary skill in the art appreciate that the total amount of a therapeutic composition or agent administered to a particular subject is determined by one or more attending physicians and may involve administration of multiple dosage forms.

Dosing regimen: Those skilled in the art will appreciate that the term "dosing regimen" may be used to refer to a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which is separated in time from other doses. In some embodiments, individual doses are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount. In some embodiments, a dosing regimen is correlated with a desired or beneficial outcome when administered across a relevant population (i.e., is a therapeutic dosing regimen).

Excipient: as used herein, refers to a non-therapeutic agent that may be included in a pharmaceutical composition, for example to provide or contribute to a desired consistency or stabilizing effect. In some embodiments, suitable pharmaceutical excipients may include, for example, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

In vitro: The term "in vitro" as used herein refers to events that occur in an artificial environment, e.g., in a test tube or reaction vessel, in cell culture, etc., rather than within a multi-cellular organism.

In vivo: as used herein refers to events that occur within a multi-cellular organism, such as a human and a non-human animal. In the context of cell-based systems, the term may be used to refer to events that occur within a living cell (as opposed to, for example, in vitro systems).

Macroemulsion: The term "macroemulsion," as used herein, refers to an emulsion in which at least some droplets have diameters in the several hundred nanometers to micrometers size range. As will be understood by those of ordinary skill in the art, a macroemulsion is characterized by droplets greater than 300 nm in diameter. In some embodiments, a macroemulsion composition utilized in accordance with the present disclosure includes one or more large agents or one or more biologically active agents. In some embodiments, a large agent included in a macroemulsion composition may be a biologically active agent. It will be appreciated by those of ordinary skill in the art that a macroemulsion composition for use in accordance with the present disclosure may be prepared according to any available means including, for example, chemical or mechanical means. In some embodiments, droplets in a macroemulsion have a size within a range of about 301 nm and about 1000 μm. In some embodiments, a macroemulsion has droplets in a size distribution of between about 301 nm and about 1000 μm. In some embodiments, droplets in a macroemulsion have a size within a range of about 500 nm and about 5000 μm. In some embodiments, a macroemulsion has droplets in a size distribution of between about 500 nm and about 5000 μm.

Nanoemulsion: The term "nanoemulsion," as used herein, refers to an emulsion in which at least some droplets have diameters in the nanometer size range. As will be understood by those of ordinary skill in the art, a nanoemulsion is characterized by droplets 300 nm or smaller in diameter. In some embodiments, a nanoemulsion composition utilized in accordance with the present disclosure includes one or more large agents or one or more biologically active agents. In some embodiments, a large agent included in a nanoemulsion composition may be a biologically active agent. It will be appreciated by those of ordinary skill in the art that a nanoemulsion composition for use in accordance with the present disclosure may be prepared according to any available means including, for example, chemical or mechanical means. In some embodiments, droplets in a nanoemulsion have a size within a range of about 1 nm and about 300 nm. In some embodiments, a nanoemulsion has droplets in a size distribution of between about 1 nm and about 300 nm.

Nanoparticle: As used herein, the term "nanoparticle" refers to a solid particle having a diameter of less than 300 nm, as defined by the National Science Foundation. In some embodiments, a nanoparticle has a diameter of less than 100 nm as defined by the National Institutes of Health.

Nanoparticle composition: As used herein, the term "nanoparticle composition" refers to any substance that contains at least one nanoparticle. In some embodiments, a nanoparticle composition is a uniform collection of nanoparticles. In some embodiments, nanoparticle compositions are dispersions or emulsions. In general, a dispersion or emulsion is formed when at least two immiscible materials are combined. An "oil-in-water" dispersion is one in which oily particles (or hydrophobic or non-polar) are dispersed within an aqueous dispersion medium. A "water-in-oil" dispersion is one in which aqueous (or hydrophilic or polar) particles are dispersed within an oily dispersion medium. Those of ordinary skill in the art will appreciate that a dispersion can be formed from any two immiscible media and is not limited strictly to combinations of aqueous and oily media. The term "dispersion medium" therefore applies broadly to any dispersion medium notwithstanding that it is common to refer to "aqueous" and "oily" categories. In some embodiments, nanoparticle compositions are nanoemulsions. In some embodiments, nanoparticle compositions comprise micelles. In some embodiments, nanoparticle compositions are stable. In some embodiments, nanoparticle compositions include one or more biologically active agents to be delivered in conjunction with the nanoparticles. In some embodiments, nanoparticle compositions are empty nanoparticle compositions (e.g., they do not contain any known therapeutic agents and/or independently active biologically active agents).

Pharmaceutical composition: As used herein, the term "pharmaceutical composition" refers to a composition in which an active agent is formulated together with one or more pharmaceutically acceptable carriers. In some embodiments, the active agent is present in unit dose amount appropriate for administration in a therapeutic regimen that shows a statistically significant probability of achieving a predetermined therapeutic effect when administered to a relevant population. In some embodiments, a pharmaceutical composition may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

Penetration enhancing agent or Penetrating Treatment: As used herein, the term "penetration enhancing agent" or "penetrating treatment" refers to an agent whose presence or level correlates with increased penetration of an agent of interest across skin, as compared with that observed in its absence. In some embodiments, a penetration enhancing agent is characterized in that it degrades and/or disrupts skin structure. In some embodiments, a penetration enhancing agent is or comprises a chemical agent (e.g., a chemical or enzyme, for example) For example, chemical agents that that may damage, disrupt, and/or degrade one or more stratum corneum components) may include, for example, alcohols, such as short chain alcohols, long chain alcohols, or polyalcohols; amines and amides, such as urea, amino acids or their esters, amides, AZONE®, derivatives of AZONE®, pyrrolidones, or derivatives of pyrrolidones; terpenes and derivatives of terpenes; fatty acids and their esters; macrocyclic compounds; tensides; or sulfoxides (e.g., dimethylsulfoxide (DMSO), decylmethylsulfoxide, etc.); surfactants, such as anionic, cationic, and nonionic surfactants; polyols; essential oils; and/or hyaluronidase. In some embodiments, a penetration enhancing agent may be an irritant in that an inflammatory and/or allergic reaction occurs when the agent is applied to skin. In some embodiments, a penetration enhancing agent is not an irritant. In some embodiments, a penetration enhancing agent may be or comprise a chemical agent that does not damage, disrupt, or degrade skin structure but whose presence or level nonetheless correlates with increased penetration of an agent of interest across skin, as compared with that observed in its absence. In some embodiments, co-peptides, carrier molecules, and carrier peptides may be penetration enhancing agents which do not damage, disrupt, and/or degrade skin structure(s). In some embodiments, co-peptides, carrier molecules, and carrier peptides may be penetration enhancing agents which do not irritate the skin. The term "penetration enhancing agent" does not encompass mechanical devices (e.g., needles, scalpels, etc.), or equivalents thereof (e.g., other damaging treatments). Also, those skilled in the art will appreciate that a structure such as a nanoparticle or an emulsion is not a chemical agent and therefore not a chemical penetration enhancing agent even if its presence correlates with enhanced skin penetration of an agent of interest that may be associated with the structure.

Pharmaceutically acceptable carrier: As used herein, the term "pharmaceutically acceptable carrier" means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

Prevent or prevention: As used herein when used in connection with the occurrence of a disease, disorder, and/or condition, refers to reducing the risk of developing the disease, disorder and/or condition and/or to delaying onset of one or more characteristics or symptoms of the disease, disorder or condition. Prevention may be considered complete when onset of a disease, disorder or condition has been delayed for a predefined period of time.

Self-administration: The term "self-administration," as used herein, refers to the situation where a subject has the ability to administer a composition to him or herself without requiring medical supervision. In some embodiments of the invention, self-administration may be performed outside of a clinical setting. To give but one example, in some embodiments of the invention, a facial cosmetic cream may be administered by a subject in one's own home.

Small molecule: As used herein, the term "small molecule" means a low molecular weight organic and/or inorganic compound. In general, a "small molecule" is a molecule that is less than about 5 kilodaltons (kD) in size. In some embodiments, a small molecule is less than about 4 kD, 3 kD, about 2 kD, or about 1 kD. In some embodiments, the small molecule is less than about 800 daltons (D), about 600 D, about 500 D, about 400 D, about 300 D, about 200 D, or about 100 D. In some embodiments, a small molecule is less than about 2000 g/mol, less than about 1500 g/mol, less than about 1000 g/mol, less than about 800 g/mol, or less than about 500 g/mol. In some embodiments, a small molecule is not a polymer. In some embodiments, a small molecule does not include a polymeric moiety. In some embodiments, a small molecule is not and/or does not comprise a protein or polypeptide (e.g., is not an oligopeptide or peptide). In some embodiments, a small molecule is not and/or does not comprise a polynucleotide (e.g., is not an oligonucleotide). In some embodiments, a small molecule is not and/or does not comprise a polysaccharide; for example, in some embodiments, a small molecule is not a glycoprotein, proteoglycan, glycolipid, etc.). In some embodiments, a small molecule is not a lipid. In some embodiments, a small molecule is a modulating agent (e.g., is an inhibiting agent or an activating agent). In some embodiments, a small molecule is biologically active. In some embodiments, a small molecule is detectable (e.g., comprises at least one detectable moiety). In some embodiments, a small molecule is a therapeutic agent. Those of ordinary skill in the art, reading the present disclosure, will appreciate that certain small molecule compounds described herein may be provided and/or utilized in any of a variety of forms such as, for example, crystal forms, salt forms, protected forms, pro-drug forms, ester forms, isomeric forms (e.g., optical and/or structural isomers), isotopic forms, etc. Those of skill in the art will appreciate that certain small molecule compounds have structures that can exist in one or more steroisomeric forms. In some embodiments, such a small molecule may be utilized in accoradance with the present disclosure in the form of an individual enantiomer, diastereomer or geometric isomer, or may be in the form of a mixture of stereoisomers; in some embodiments, such a small molecule may be utilized in accordance with the present disclosure in a racemic mixture form. Those of skill in the art will appreciate that certain small molecule compounds have structures that can exist in one or more tautomeric forms. In some embodiments, such a small molecule may be utilized in accoradance with the present disclosure in the form of an individual tautomer, or in a form that interconverts between tautomeric forms. Those of skill in the art will appreciate that certain small molecule compounds have structures that permit isotopic substitution (e.g., $^2H$ or $^3H$ for H; $^{11}C$, $^{13}C$ or $^{14}C$ for 12C; $^{13}N$ or $^{15}N$ for 14N; $^{17}O$ or $^{18}O$ for 16O; $^{36}Cl$ for XXC; $^{18}F$ for) XXF; 1311 for XXXI; etc). In some embodiments, such a small molecule may be utilized in accordance with the present disclosure in one or more isotopically modified forms, or mixtures thereof. In some embodiments, reference to a particular small molecule compound may relate to a specific form of that compound. In some embodiments, a particular small molecule compound may be provided and/or utilized in a salt form (e.g., in an acid-addition or base-addition salt form, depending on the compound); in some such embodiments, the salt form may be a pharmaceutically acceptable salt form. In some embodiments, where a small molecule compound is one that exists or is found in nature, that compound may be provided and/or utilized in accordance in the present disclosure in a form different from that in which it exists or is found in nature. Those of ordinary skill in the art will appreciate that, in some embodiments, a preparation of a particular small molecule compound that contains an absolute or relative amount of the compound, or of a particular form thereof, that is different from the absolute or relative (with respect to another component of the preparation including, for example, another form of the compound) amount of the compound or form that is present in a reference preparation of interest (e.g., in a primary sample from a source of interest such as a biological or environmental source) is distinct from the compound as it exists in the reference preparation or source. Thus, in some embodiments, for example, a preparation of a single stereoisomer of a small molecule compound may be considered to be a different form of the compound than a racemic mixture of the compound; a particular salt of a small molecule compound may be considered to be a different form from another salt form of the compound; a preparation that contains only a form of the compound that contains one conformational isomer ((Z) or (E)) of a double bond may be considered to be a different form of the compound from one that contains the other conformational isomer ((E) or (Z)) of the double bond; a preparation in which one or more atoms is a different isotope than is present in a reference preparation may be considered to be a different form; etc.

Subject: As used herein, the term "subject" refers an organism, typically a mammal (e.g., a human, in some embodiments including prenatal human forms). In some embodiments, a subject is suffering from a relevant disease, disorder or condition. In some embodiments, a subject is susceptible to a disease, disorder, or condition. In some embodiments, a subject displays one or more symptoms or characteristics of a disease, disorder or condition. In some embodiments, a subject does not display any symptom or characteristic of a disease, disorder, or condition. In some embodiments, a subject is someone with one or more features characteristic of susceptibility to or risk of a disease, disorder, or condition. In some embodiments, a subject is a patient. In some embodiments, a subject is an individual to whom diagnosis and/or therapy is and/or has been administered.

Symptoms are reduced: As used herein, the term "symptoms are reduced" refers to when one or more symptoms of a particular disease, disorder or condition is reduced in magnitude (e.g., intensity, severity, etc.) and/or frequency. For purposes of clarity, a delay in the onset of a particular symptom is considered one form of reducing the frequency of that symptom.

Therapeutic agent: As used herein, the term "therapeutic agent" refers to any agent that has a therapeutic effect and/or elicits a desired biological and/or pharmacological effect, when administered to a subject.

Therapeutically effective amount: As used herein, is meant an amount that produces the desired effect for which it is administered. In some embodiments, the term refers to an amount that is sufficient, when administered to a population suffering from or susceptible to a disease, disorder, and/or condition in accordance with a therapeutic dosing regimen, to treat the disease, disorder, and/or condition. In some embodiments, a therapeutically effective amount is one that reduces the incidence and/or severity of, and/or delays onset of, one or more symptoms of the disease, disorder, and/or condition. Those of ordinary skill in the art will appreciate that the term "therapeutically effective amount" does not in fact require successful treatment be achieved in a particular individual. Rather, a therapeutically effective amount may be that amount that provides a particular desired pharmacological response in a significant number of subjects when administered to patients in need of such treatment. In some embodiments, reference to a therapeutically effective amount may be a reference to an amount as measured in one or more specific tissues (e.g., a tissue affected by the disease, disorder or condition) or fluids (e.g., blood, saliva, serum, sweat, tears, urine, etc.). Those of ordinary skill in the art will appreciate that, in some embodiments, a therapeutically effective amount of a particular agent or therapy may be formulated and/or administered in a single dose. In some embodiments, a therapeutically effective agent may be formulated and/or administered in a plurality of doses, for example, as part of a dosing regimen.

Treatment: As used herein, the term "treatment" (also "treat" or "treating") refers to any administration of a therapy that partially or completely alleviates, ameliorates, relives, inhibits, delays onset of, reduces severity of, and/or reduces incidence of one or more symptoms, features, and/or causes of a particular disease, disorder, and/or condition. In some embodiments, such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

DETAILED DESCRIPTION OF CERTAIN EMBODIMENTS

Plasminogen Activator Inhibitor 1 (PAI-1)

Plasminogen Activator Inhibitor (PAI-1) is a serine protease inhibitor (serpin) protein encoded by the SERPINE 1 gene. PAI-1 is originally known for its involvement in maintaining homeostatic equilibrium in the body, as it is the principal inhibitor of tissue plasminogen activator (tPA) and urokinase (uPA). Elevated PAI-1 has also been reported to be associated with organ fibrosis and disease in multiple organ systems (e.g., heart, lung, liver, kidney, and skin).

The present disclosure, in some embodiments, provides the surprising insight that PAI-1 inhibitors are effective in treating and/or preventing some types of alopecia, but not others. The present disclosure, in some embodiments, encompasses the surprising insight and recognition that PAI-1 inhibitors may be particularly useful in the treatment and/or prevention of specific types of hair loss (or alopecia), including androgenetic alopecia, alopecia areata, frontal fibrosing alopecia, and senescent alopecia. Furthermore, surprisingly, the present disclosure, in some embodiments, provides the insight that the new technologies may not be particularly useful in the treatment and/or prevention of other types of alopecia such as radiation-induced alopecia, chemotherapy-induced alopecia, and alopecia due to chronic discoid lupus erythematosus. While the growth cycle and physiology of the hair is well known and understood, there are currently no highly effective prevention or treatment techniques for hair loss, specifically, for example specific types of hair loss (or alopecia), including androgenetic alopecia, alopecia areata, frontal fibrosing alopecia, and senescent alopecia. In some embodiments, provided methods and/or compositions provide targeted therapy. For example, in some embodiments, provided methods and compositions provide surprisingly effective therapies comprising one or more PAI-1 inhibitors. Without wishing to be bound by any particular theory, it is proposed that, in some embodiments, administration of a PAI-1 inhibitor as described herein may stimulate Hair Follicle Stem Cells (HFSC), and such stimulation may contribute to treatment or prevention of hair loss.

In some embodiments provided methods, kits and compositions may be or comprise emulsions. In some embodiments provided methods, kits and compositions may be or comprise macroemulsions. In some embodiments provided methods, kits and compositions may be or comprise nanoemulsions. In some embodiments provided methods, kits and compositions comprise a combination therapy or treatment, wherein for example, in some embodiments, provided compositions may be administered in combination with one or more additional treatments. In some embodiments the one or more additional treatments is or comprises other active agents and/or therapeutic modalities (e.g. one or more PAI-inhibitors, or other agents), such as known therapeutic agents and/or independently active biologically active agents.

Diseases, Disorders, and Conditions

The present invention provides technologies for treating and/or preventing certain types of alopecia. In some embodiments, the present invention provides technologies for treating and/or preventing diseases, disorders or conditions associated with the epidermal and/or dermal level of the skin. In some embodiments, the present invention provides technologies for treating and/or preventing any one or a combination of androgenetic alopecia, alopecia areata, frontal fibrosing alopecia, and senescent alopecia. In some embodiments, the present disclosure provides new technologies that may not be particularly useful in the treatment and/or prevention of other types of alopecia such as radiation-induced alopecia, chemotherapy-induced alopecia, and alopecia due to chronic discoid lupus erythematosus.

In some embodiments, the present invention provides technologies for treating and/or preventing one or more of specific types of hair loss (or alopecia), including androgenetic alopecia, alopecia areata, frontal fibrosing alopecia, and senescent alopecia, and/or combinations thereof. In some embodiments, the present invention provides technologies for treating and/or preventing specific types of hair loss (or alopecia), including androgenetic alopecia, alopecia areata, frontal fibrosing alopecia, and senescent alopecia, but not treating or preventing other types of alopecia such as radiation-induced alopecia, chemotherapy-induced alopecia, and alopecia due to chronic discoid lupus erythematosus.

Hair Loss

In some embodiments, provided technologies are useful for treating and/or preventing hair loss. Baldness involves the state of lacking hair where it often grows, especially on the head. The most common form of baldness is a progressive hair thinning condition called androgenic alopecia or "male pattern baldness" that occurs in adult male humans and other species. The amount and patterns of baldness can vary greatly; it ranges from male and female "pattern alopecia" (androgenic alopecia, also called androgenetic alopecia or alopecia androgenetica); "alopecia areata," which involves the loss of some of the hair from the head; "alopecia totalis," which involves the loss of all head hair; to the most extreme form, "alopecia universalis," which involves the loss of all hair from the head and the body. Frontal fibrosing alopecia (FFA) is characterized primarily by slowly progressive hair loss and scarring on the scalp near the forehead. In some cases, the hair loss in this type of alopecia may involve the eyebrows, eye lashes, and/or other body parts. Senescent alopecia, also known as involutional alopecia, is hair loss caused by old age. Other types of alopecia include, but are not limited to, radiation-induced alopecia, chemotherapy-induced alopecia, alopecia due to chronic discoid lupus erythematosus, postpartum alopecia, and telogen effluvium.

Current therapies used in the treatment of hair loss include, but are not limited to, botulinum toxin, aza-steroids, such as finasteride (PROPECIA®; PROSCAR®; etc.) or dutasteride (AVODART®); topically administered minoxidil, a vasodilator (ROGAINE®); antiandrogens (e.g., ketoconazole, fluconazole, spironolactone, etc.); platelet-rich plasma, saw palmetto; caffeine; copper peptides; nitroxide spin labels TEMPO and TEMPOL; unsaturated fatty acids (e.g., gamma linolenic acid); hedgehog agonists; azelaic acid and zinc in combination; Chinese knotweed; pumpkin seed; spironolactone; tretinoin; zinc; stinging nettle; and/or combinations thereof. Pharmaceutical compositions in accordance with the present invention may be administered alone and/or in combination with these therapies that are used to treat the symptoms and/or causes of hair loss, for the treatment of hair loss.

In some embodiments, provided compositions for treatment and/or prevention of hair loss are formulated into a suspension.

In some embodiments, provided compositions for treatment and/or prevention of hair loss are formulated into a suspension, a foam, a cream, a liniment, a lotion, a gel, a shampoo, a conditioner, etc.

In some embodiments, provided compositions for treatment and/or prevention of hair loss are administered locally to an affected site (e.g., scalp, hair follicle, face, neck, back, arms, chest, etc.).

Administration of the disclosed compositions and/or formulations may be through any one of many routes. In some embodiments, provided compositions for treatment and/or prevention of hair loss are administered systemically (e.g., oral administration). In some embodiments, the administration is topical. In some embodiments, the administration is oral. In some embodiments, the administration is via an injection.

In some embodiments, the present invention involves administration of at least one therapeutic agent (e.g., PAI-1 inhibitor) in a suspension, in an amount sufficient to achieve a reduction in the degree and/or prevalence of one or more symptoms of hair loss of at least about 25%; in some embodiments in an amount sufficient to achieve a reduction in the degree and/or prevalence of one or more symptoms of hair loss of at least about 30%; in some embodiments in an amount sufficient to achieve a reduction in the degree and/or prevalence of one or more symptoms of hair loss of at least about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90% or more.

In some embodiments, the present invention involves administration of at least one therapeutic agent (e.g., PAI-1 inhibitor) in a nanoparticle composition or a nanoemulsion composition or an emulsion composition or a foam formulation or a cream formulation or an oil or a lotion formulation or a gel or a shampoo or a conditioner, in an amount sufficient to achieve a reduction in the degree and/or prevalence of one or more symptoms of hair loss of at least about 25%; in some embodiments in an amount sufficient to achieve a reduction in the degree and/or prevalence of one or more symptoms of hair loss of at least about 30%; in some embodiments in an amount sufficient to achieve a reduction in the degree and/or prevalence of one or more symptoms of hair loss of at least about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90% or more.

PAI-1 Inhibitors

PAI-1 inhibitors can be used to treat or prevent medical conditions or diseases associated with over-expression of PAI-1. PAI-1 inhibitors can be antibodies, peptides, polypeptides, proteins, nucleic acids, lipids, carbohydrates, small molecules, metals, polymers, therapeutic antibodies, or any combinations thereof. In some embodiments, the PAI-1 inhibitor is an siRNA. In some embodiments, the PAI-1 inhibitor is a benzopyran compound, a butadiene, spironolactone, imidapril, an angiotensin converting enzyme inhibitor (ACEI, captopril, or enalapril), an angiotensin II receptor antagonist (AIIRA), a defibrotide (a polydeoxyribonucleotide) and any combination thereof. In some embodiments, the PAI-1 inhibitor is a benzopyran compound.

In some embodiments, the PAI-1 inhibitor may be a small molecule. For example, the PAI-1 inhibitor is 5-Chloro-2-1 [(2-{[3-(furan-3-yl)phenyl]amino}-2-oxoethoxy)acetyl] amino benzoic acid. In another example, the PAI-1 inhibitor is 5-Chloro-2-{[{[3-(furan-3-yl)phenyl]amino}(oxo)acetyl] amino}benzoic acid. Table 1 below lists the exemplary PAI-1 inhibitors.

TABLE

| Exemplary PAI-1 inhibitors | | |
| --- | --- | --- |
| Chemical Name | Molecular Formula | Molecular Weight |
| 5-Chloro-2-{[(2-{[3-(furan-3-yl)phenyl]amino}-2-oxoethoxy) acetyl]amino benzoic acid | $C_{21}H_{17}ClN_2O_6$ | 428.82 |
| 5-Chloro-2-{[{[3-(furan-3-yl)phenyl]amino}(oxo) acetyl]amino} benzoic acid | $C_{19}H_{13}ClN_2O_5$ | 384.77 |

Compositions and Formulations

As noted herein, the present invention provides and/or utilizes compositions comprising one or more PAI-1 inhibitors for administration. In some embodiments the administration is in combination with microneedle skin conditioning (MSC). In some embodiments, provided compositions may be formulated for topical and/or transdermal delivery (e.g., as lotions, creams, liniments, ointments, powders, gels, drops, etc.). In some embodiments, provided compositions may be or include a nanoemulsion. In some embodiments, provided compositions may be or include a macroemulsion.

Nanoparticle compositions are useful in a variety of contexts, and have proven to be particularly useful and/or effective in the context of medical applications, including administering therapeutic agents (e.g., PAI-1 inhibitors) to patients in need thereof. Nanoparticle compositions have proven to be particularly useful and/or effective in the context of topical administration of therapeutic agents (see, e.g., PCT patent application number PCT US06/46236, filed Dec. 1, 2006, published as WO 08/045107 on Apr. 17, 2008, and entitled "BOTULINUM NANOEMULSIONS; in PCT patent application number PCT US07/86018, filed Nov. 30, 2007, published as WO 08/070538 on Jun. 12, 2008, and entitled "AMPHIPHILIC ENTITY NANOPARTICLES"; and/or in PCT patent application number PCT US09/48972, filed Jun. 26, 2009, published as WO 09/158687 on Dec. 30, 2009, and entitled "DERMAL DELIVERY"; the contents of all of which are incorporated herein by reference).

In some embodiments, provided nanoparticle compositions have particular components, and/or relative amounts of components, as described herein. In some embodiments, provided nanoparticle compositions have particular structural and/or functional attributes that distinguish and/or define them. In some embodiments, exemplary attributes (e.g., physical, structural, and/or functional attributes) that have been associated with nanoparticle compositions in general are described in the following paragraphs. In some embodiments, provided nanoparticle compositions have one or more of these attributes. In some embodiments, provided nanoparticle compositions do not have any of these attributes.

In general, a nanoparticle composition is any composition that includes at least one nanoparticle. In some embodiments, nanoparticle compositions comprise at least one known therapeutic agent and/or an independently active biologically active agent (e.g., PAI-1 inhibitor). A known therapeutic agent and/or an independently active biologically active agent may be encapsulated or completely surrounded by one or more nanoparticles; associated with the nanoparticle interface; and/or adsorbed to the outer surface of one or more nanoparticles. A known therapeutic agent and/or an independently active biologically active agent may or may not be covalently linked to the nanoparticles and/or nanoparticle compositions; a known therapeutic agent and/or an independently active biologically active agent may or may not be attached to nanoparticles and/or nanoparticle compositions by adsorption forces. In some embodiments, nanoparticle compositions comprise empty nanoparticles (e.g., nanoparticles not containing any known therapeutic agents and/or independently active biologically active agents).

In some embodiments, nanoparticle compositions are stable. In some embodiments, nanoparticle compositions are uniform. For example, in some embodiments, the difference between the minimum diameter and maximum diameter of the nanoparticles in a nanoparticle composition does not exceed approximately 600 nm, approximately 550 nm, approximately 500 nm, approximately 450 nm, approximately 400 nm, approximately 350 nm, approximately 300 nm, approximately 250 nm, approximately 200 nm, approximately 150 nm, or approximately 100 nm, approximately 90 nm, approximately 80 nm, approximately 70 nm, approximately 60 nm, approximately 50 nm, or fewer nm.

In some embodiments, particles within nanoparticle compositions have diameters (e.g., average and/or median diameters) that are smaller than about 1000 nm, about 600 nm, about 550 nm, about 500 nm, about 450 nm, about 400 nm, about 350 nm, about 300 nm, about 250 nm, about 200 nm, about 150 nm, about 130 nm, about 120 nm, about 115 nm, about 110 nm, about 100 nm, about 90 nm, about 80 nm, about 50 nm, or less.

In some embodiments, particles within nanoparticle compositions have diameters (e.g., average and/or median diameters) within the range of about 10 nm and about 600 nm. In some embodiments, particles within nanoparticle compositions have diameters (e.g., average and/or median diameters) within the range of about 10 nm to about 300 nm, about 10 nm to about 200 nm, about 10 nm to about 150 nm, about 10 nm to about 130 nm, about 10 nm to about 120 nm, about 10 nm to about 115 nm, about 10 nm to about 110 nm, about 10 nm to about 100 nm, or about 10 nm to about 90 nm. In some embodiments, particles within nanoparticle compositions have diameters (e.g., average and/or median diameters) within the range of 1 nm to 1000 nm, 1 nm to 600 nm, 1 nm to 500 nm, 1 nm to 400 nm, 1 nm to 300 nm, 1 nm to 200 nm, 1 nm to 150 nm, 1 nm to 120 nm, 1 nm to 100 nm, 1 nm to 75 nm, 1 nm to 50 nm, or 1 nm to 25 nm. In some embodiments, particles within nanoparticle compositions have diameters (e.g., average and/or median diameters) of 1 nm to 15 nm, 15 nm to 200 nm, 25 nm to 200 nm, 50 nm to 200 nm, or 75 nm to 200 nm.

In some embodiments, the total particle distribution is encompassed within the specified range of particle diameter size. In some embodiments, less than 50%, 25%, 10%, 5%, or 1% of the total particle distribution is outside of the specified range of particle diameter sizes. In some embodiments, less than 1% of the total particle distribution is outside of the specified range of particle diameter sizes. In certain embodiments, the nanoparticle composition is substantially free of particles having a diameter larger than 300 nm, 250 nm, 200 nm, 150 nm, 120 nm, 100 nm, 75 nm, 50 nm, or 25 nm. In some embodiments, less than 50%, 25%, 10%, 5%, or 1% of the total particle distribution have diameters larger than 300 nm, 250 nm, 200 nm, 150 nm, 120 nm, 100 nm, 75 nm, 50 nm, or 25 nm.

In some embodiments, particles within nanoparticle compositions have an average particle size that is under about 600 nm, about 550 nm, about 500 nm, about 450 nm, about 400 nm, about 350 nm, about 300 nm, about 250 nm, about 200 nm, about 150 nm, about 130 nm, about 120 nm, about 115 nm, about 110 nm, about 100 nm, about 90 nm, or about 50 nm. In some embodiments, the average particle size is within the range of about 10 nm and about 300 nm, about 50 nm and about 250, about 60 nm and about 200 nm, about 65 nm and about 150 nm, or about 70 nm and about 130 nm. In some embodiments, the average particle size is about 80 nm and about 110 nm. In some embodiments, the average particle size is about 90 nm and about 100 nm.

In some embodiments, a majority of the particles within nanoparticle compositions have diameters below a specified size or within a specified range. In some embodiments, the majority is more than 50%, 60%, 70%, 75%, 80%, 85%, 90%, 95%, 96%, 97%, 98%, 99%, 99.5%, 99.6%, 99.7%, 99.8%, 99.9% or more of the particles in the composition.

In some embodiments, nanoparticle compositions are substantially free of particles having a diameter in excess of 600 nm. Specifically, in some embodiments, fewer than 50% of the nanoparticles in nanoparticle compositions have a diameter in excess of 600 nm. In some embodiments, fewer than 25% of the particles have a diameter in excess of 600 nm. In some embodiments, fewer than 20%, 19%, 18%, 17%, 16%, 15%, 14%, 13%, 12%, 10%, 9%, 8%, 7%, 6%, 5%, 4%, 3%, 2%, 1%, 0.5% or less of the particles have a diameter in excess of 600 nm. Furthermore, in some embodiments, the nanoparticles in nanoparticle compositions have diameters within the range of 10 nm and 600 nm.

In some embodiments, nanoparticle compositions are substantially free of particles having a diameter in excess of 500 nm. Specifically, in some embodiments, fewer than 50% of the nanoparticles in nanoparticle compositions have a diameter in excess of 500 nm. In some embodiments, fewer than 25% of the particles have a diameter in excess of 500 nm. In some embodiments, fewer than 20%, 19%, 18%, 17%, 16%, 15%, 14%, 13%, 12%, 10%, 9%, 8%, 7%, 6%, 5%, 4%, 3%, 2%, 1%, 0.5% or less of the particles have a diameter in excess of 500 nm. Furthermore, in some embodiments, the nanoparticles in nanoparticle compositions have diameters within the range of 10 nm and 500 nm.

In some embodiments, nanoparticle compositions are substantially free of particles having a diameter in excess of 400 nm. Specifically, in some embodiments, fewer than 50% of the nanoparticles in nanoparticle compositions have a diameter in excess of 400 nm. In some embodiments, fewer than 25% of the particles have a diameter in excess of 400 nm. In some embodiments, fewer than 20%, 19%, 18%, 17%, 16%, 15%, 14%, 13%, 12%, 10%, 9%, 8%, 7%, 6%, 5%, 4%, 3%, 2%, 1%, 0.5% or less of the particles have a diameter in excess of 400 nm. Furthermore, in some embodiments, the nanoparticles in nanoparticle compositions have diameters within the range of 10 nm and 400 nm.

In some embodiments, nanoparticle compositions are substantially free of particles having a diameter in excess of 300 nm. Specifically, in some embodiments, fewer than 50%, of the nanoparticles in nanoparticle compositions have a diameter in excess of 300 nm. In some embodiments, fewer than 25% of the particles have a diameter in excess of 300 nm. In some embodiments, fewer than 20%, 19%, 18%, 17%, 16%, 15%, 14%, 13%, 12%, 10%, 9%, 8%, 7%, 6%, 5%, 4%, 3%, 2%, 1%, 0.5% or less of the particles have a diameter in excess of 300 nm. Furthermore, in some embodiments, the nanoparticles in nanoparticle compositions have diameters within the range of 10 nm and 300 nm.

In some embodiments, nanoparticle compositions are substantially free of particles having a diameter in excess of 200 nm. Specifically, in some embodiments, fewer than 50%, of the nanoparticles in nanoparticle compositions have a diameter in excess of 200 nm. In some embodiments, fewer than 25% of the particles have a diameter in excess of 200 nm. In some embodiments, fewer than 20%, 19%, 18%, 17%, 16%, 15%, 14%, 13%, 12%, 10%, 9%, 8%, 7%, 6%, 5%, 4%, 3%, 2%, 1%, 0.5% or less of the particles have a diameter in excess of 200 nm. Furthermore, in some embodiments, the nanoparticles in nanoparticle compositions have diameters within the range of 10 nm and 200 nm.

In some embodiments, provided compositions are substantially free of particles having a diameter in excess of 150 nm. Specifically, in some embodiments, fewer than 50% of the nanoparticles in provided compositions have a diameter in excess of 150 nm. In some embodiments, fewer than 25% of the particles have a diameter in excess of 150 nm. In some embodiments, fewer than 20%, 19%, 18%, 17%, 16%, 15%, 14%, 13%, 12%, 10%, 9%, 8%, 7%, 6%, 5%, 4%, 3%, 2%, 1%, 0.5% or less of the particles have a diameter in excess of 150 nm. Furthermore, in some embodiments, the nanoparticles in provided compositions have diameters within the range of 10 nm and 150 nm.

In some embodiments, nanoparticle compositions are substantially free of particles having a diameter in excess of 120 nm. Specifically, in some embodiments, fewer than 50%, of the nanoparticles in nanoparticle compositions have a diameter in excess of 120 nm. In some embodiments, fewer than 25% of the particles have a diameter in excess of 120 nm. In some embodiments, fewer than 20%, 19%, 18%, 17%, 16%, 15%, 14%, 13%, 12%, 10%, 9%, 8%, 7%, 6%, 5%, 4%, 3%, 2%, 1%, 0.5% or less of the particles have a diameter in excess of 120 nm. Furthermore, in some embodiments, the nanoparticles in nanoparticle compositions have diameters within the range of 10 nm and 120 nm.

In some embodiments, a majority of particles in a provided composition have diameters (e.g., average and/or median diameters) between 10 nm and 150 nm. In some embodiments, a majority of particles in a provided composition have diameters (e.g., average and/or median diameters) between 10 nm and 120 nm. In some embodiments, a majority of particles in a provided composition have diameters (e.g., average and/or median diameters) between 20 nm and 120 nm. In some embodiments, a majority of particles in a provided composition have diameters (e.g., average and/or median diameters) between 20 nm and 110 nm. In some embodiments, a majority of particles in a provided composition have diameters (e.g., average and/or median diameters) between 20 nm and 100 nm. In some embodiments, a majority of particles in a provided composition have diameters (e.g., average and/or median diameters) between 20 nm and 90 nm. In some embodiments, a majority of particles in a provided composition have diameters (e.g., average and/or median diameters) between 20 nm and 80 nm. In some embodiments, a majority of particles in a provided composition have diameters (e.g., average and/or median diameters) between 20 nm and 70 nm. In some embodiments, a majority of particles in a provided composition have diameters (e.g., average and/or median diameters) between 20 nm and 60 nm. In some embodiments, a majority of particles in a provided composition have diameters (e.g., average and/or median diameters) between 20 nm and 50 nm. In some embodiments, a majority of particles in a provided composition have diameters (e.g., average and/or median diameters) between 20 nm and 40 nm. In some embodiments, a majority of particles in a provided composition have diameters (e.g., average and/or median diameters) between 20 nm and 30 nm.

In some embodiments, a majority of nanoparticles in a nanoparticle composition have diameters (e.g., average and/or median diameters) between 10 nm and 120 nm. In some embodiments, a majority of nanoparticles in a nanoparticle composition have diameters (e.g., average and/or median diameters) between 20 nm and 120 nm. In some embodiments, a majority of nanoparticles in a nanoparticle composition have diameters (e.g., average and/or median diameters) between 20 nm and 110 nm. In some embodiments, a majority of nanoparticles in a nanoparticle composition have diameters (e.g., average and/or median diameters) between 20 nm and 100 nm. In some embodiments, a majority of nanoparticles in a nanoparticle composition have diameters between 20 nm and 90 nm. In some embodiments, a majority of nanoparticles in a nanoparticle composition have diameters (e.g., average and/or median diameters) between 20 nm and 80 nm. In some embodiments, a majority of nanoparticles in a nanoparticle composition have diameters (e.g., average and/or median diameters) between 20 nm and 70 nm. In some embodiments, a majority of nanoparticles in a nanoparticle composition have diameters (e.g., average and/or median diameters) between 20 nm and 60 nm. In some embodiments, a majority of nanoparticles in a nanoparticle composition have diameters (e.g., average and/or median diameters) between 20 nm and 50 nm. In some embodiments, a majority of nanoparticles in a nanoparticle composition have diameters (e.g., average and/or median diameters) between 20 nm and 40 nm. In some embodiments, a majority of nanoparticles in a nanoparticle composition have diameters (e.g., average and/or median diameters) between 20 nm and 30 nm.

In some embodiments, about 50% of nanoparticles in a nanoparticle composition have diameters (e.g., average and/or median diameters) between 10 nm and 40 nm. In some embodiments, about 90% of nanoparticles in a nanoparticle composition have diameters (e.g., average and/or median diameters) between 10 nm and 80 nm. In some embodiments, about 90% of nanoparticles in a nanoparticle composition have diameters (e.g., average and/or median diameters) between 10 nm and 90 nm. In some embodiments, about 95% of nanoparticles in a nanoparticle composition have diameters (e.g., average and/or median diameters) between 10 nm and 110 nm. In some embodiments, about 95% of nanoparticles in a nanoparticle composition have diameters (e.g., average and/or median diameters) between 10 nm and 120 nm. In some embodiments, about 95% of particles in a provided composition have diameters (e.g., average and/or median diameters) between 10 nm and 150 nm.

In some embodiments, about 50% of the aggregate volume of all nanoparticles in a nanoparticle composition comprises or consists of nanoparticles having diameters between 10 nm and 40 nm. In some embodiments, about 90% of the aggregate volume of all nanoparticles in a nanoparticle composition comprises or consists of nanoparticles having diameters between 10 nm and 80 nm. In some embodiments, about 95% of the aggregate volume of all nanoparticles in a nanoparticle composition comprises or consists of nanoparticles having diameters between 10 nm and 110 nm. In some embodiments, about 95% of the aggregate volume of all nanoparticles in a nanoparticle composition comprises or consists of nanoparticles having diameters between 10 nm and 120 nm. In some embodiments, about 95% of the aggregate volume of all particles in a provided composition comprises or consists of nanoparticles having diameters between 10 nm and 150 nm.

In some embodiments, nanoparticle compositions are or comprise emulsions or dispersions. In some embodiments, nanoparticle compositions are "oil-in-water" dispersions (i.e., dispersions in which oily particles are dispersed within an aqueous dispersion medium); in some embodiments, nanoparticle compositions are "water-in-oil" dispersions (i.e., dispersions in which aqueous particles are dispersed within an oily dispersion medium).

In some embodiments, provided compositions do not require toxic solvents. By contrast, many conventional strategies for inducing formation of nanoparticles in a composition utilize toxic (typically organic) solvents. In some embodiments, provided compositions do not require polymers. By contrast, many conventional strategies for preparing compositions that contain nanoparticle structures require polymers.

In some embodiments, provided compositions have better tissue absorption and/or better biocompatibility than other nanoparticle compositions. For example, in some embodiments, provided compositions have better tissue absorption and/or better biocompatibility than nanoparticle compositions that are not uniform, that utilize one or more toxic (e.g., organic) solvents, and/or that utilize one or more polymers.

In some embodiments, nanoparticle compositions are stable. In some embodiments, a stable nanoparticle composition is one for which the average particle size, the maximum particle size, the range of particle sizes, and/or the distribution of particle sizes (i.e., the percentage of particles above a designated size and/or outside a designated range of sizes) is maintained for a period of time. In some embodiments, the period of time is at least about one hour; in some embodiments the period of time is about 5 hours, about 10 hours, about one (1) day, about one (1) week, about two (2) weeks, about one (1) month, about two (2) months, about three (3) months, about four (4) months, about five (5) months, about six (6) months, about eight (8) months, about ten (10) months, about twelve (12) months, about twenty-four (24) months, or longer. In some embodiments, the period of time is within the range of about one (1) day to about twenty-four (24) months, about two (2) weeks to about twelve (12) months, about two (2) months to about five (5) months, etc. For example, if a population of nanoemulsion particles is subjected to prolonged storage, temperature changes, and/or pH changes and a majority of the nanoparticles in the population maintain a diameter within a stated range (i.e., for example, between approximately 10 nm and about 120 nm), the nanoparticle composition is stable. For some such populations, a majority is more than about 50%, about 60%, about 70%, about 80%, about 90%, about 95%, about 96%, about 97%, about 98%, about 99%, about 99.5%, about 99.6%, about 99.7%, about 99.8%, about 99.9%, or more than about 99.9% pure. In some embodiments, where a nanoparticle composition comprises at least one known therapeutic agent and/or an independently active biologically active agent, the nanoparticle composition is considered stable if the concentration of the known therapeutic agent and/or an independently active biologically active agent (e.g., PAI-1 inhibitors) is maintained in the composition over the designated period of time under a designated set of conditions.

As described herein, provided compositions are useful in various cosmetic and/or medical applications. Such compositions may be administered to a subject by any appropriate route, as may be readily determined by those skilled in the art for the disease, disorder, or condition of interest. In some embodiments, routes that may be employed may include one or more of oral (PO), intravenous (IV), intramuscular (IM), intra-arterial, intramedullary, intrathecal, subcutaneous (SQ), intraventricular, transdermal, interdermal, intradermal, rectal (PR), vaginal, intraperitoneal (IP), intragastric (IG), topical and/or transdermal (e.g., by lotions, creams, powders, ointments, liniments, gels, drops, etc.), mucosal, intranasal, buccal, enteral, vitreal, and/or sublingual administration; by intratracheal instillation, bronchial instillation, and/or inhalation; as an oral spray, nasal spray, and/or aerosol, and/or through a portal vein catheter; and/or combinations of any of the foregoing. In most embodiments, as described herein, administration will be topical, parenteral, or oral.

Formulations of provided compositions may be prepared by any appropriate method, as will be understood in the art. In general, such preparatory methods include a step of bringing an provided composition into association with one or more excipients, and then, if necessary and/or desirable, shaping and/or packaging into an appropriate form for administration, for example as or in a single or multi-dose unit.

In some embodiments, compositions may be prepared, packaged, and/or sold in bulk, as a single unit dose, and/or as a plurality of single unit doses. As used herein, a "unit dose" is a discrete amount of a pharmaceutical composition comprising a predetermined amount of the provided composition. The amount of a provided composition is generally equal to the dosage of the provided composition which would be administered to a subject and/or a convenient fraction of such a dosage such as, for example, one-half or one-third of such a dosage.

In some embodiments, appropriate excipients for use in compositions (e.g., pharmaceutically and/or cosmetically acceptable compositions) may, for example, include one or more excipients such as solvents, dispersion media, granulating media, diluents, or other liquid vehicles, dispersion or suspension aids, surface active agents and/or emulsifiers, isotonic agents, thickening or emulsifying agents, preservatives, solid binders, lubricants, disintegrating agents, binding agents, preservatives, buffering agents and the like, as suited to the particular dosage form desired. In some embodiments, excipients such as cocoa butter and/or suppository waxes, coloring agents, coating agents, sweetening, flavoring, and/or perfuming agents can be utilized. Remington's The Science and Practice of Pharmacy, 21$^{st}$ Edition, A. R. Gennaro (Lippincott, Williams & Wilkins, Baltimore, MD, 2005; incorporated herein by reference) discloses various excipients used in formulating pharmaceutical compositions and known techniques for the preparation thereof.

In some embodiments, an appropriate excipient (e.g., a pharmaceutically and/or cosmetically acceptable excipient) is at least 95%, at least 96%, at least 97%, at least 98%, at least 99%, or 100% pure. In some embodiments, an excipient is approved by United States Food and Drug Administration. In some embodiments, an excipient is pharmaceutical grade. In some embodiments, an excipient meets the standards of the United States Pharmacopoeia (USP), the European Pharmacopoeia (EP), the British Pharmacopoeia, and/or other International Pharmacopoeia.

In some embodiments, provided compositions are formulated as a cream, liniment, ointment, oil, foam, spray, lotion, liquid, powder, thickening lotion, or gel (e.g., formulated for transdermal delivery as described herein). Particular exemplary such formulations may be prepared, for example, as cosmetic formulation products such as skin softeners, nutritional lotion type emulsions, cleansing lotions, cleansing creams, skin milks, emollient lotions, massage creams, emollient creams, make-up bases, facial packs or facial gels, cleaner formulations such as shampoos, rinses, body cleansers, hair-tonics, or soaps, or dermatological compositions such as lotions, ointments, gels, creams, liniments, patches, deodorants, or sprays.

The present disclosure encompasses the recognition that emulsion technologies can provide stabilization benefits to agents of interest, including to PAI-1 inhibitors as described herein. Furthermore, emulsions, both macro and nano, may be used to prepare formulations for administration of PAI-1 inhibitors as treatment for for treating and/or preventing any one or a combination of androgenetic alopecia, alopecia areata, frontal fibrosing alopecia, and senescent alopecia. In some embodiments, the present disclosure provides new technologies that may not be particularly useful in the treatment and/or prevention of other types of alopecia such as radiation-induced alopecia, chemotherapy-induced alopecia, and alopecia due to chronic discoid lupus erythematosus. In some particular embodiments, formulations may be topical formulations. In some particular embodiments, formulations may be injectable formulations. In some particular embodiments, formulations may be oral formulations.

In some embodiments, provided compositions comprise provided nanoemulsion compositions. In some embodiments, provided compositions are cream and/or lotion formulations. In some embodiments, provided cream and/or lotion formulations comprise nanoemulsion compositions. In some embodiments, compositions comprise provided nanoemulsion compositions but are not cream and/or lotion formulations. In some embodiments, suitable compositions are formulated into creams and/or lotions but do not comprise a nanoemulsion composition.

In some embodiments, provided compositions comprise a mixture of a provided nanoemulsion composition and one or more pharmaceutically acceptable excipients, e.g., for topical and/or transdermal (e.g., by lotions, creams, powders, ointments, liniments, gels, drops, etc.) administration.

Emulsions

In some embodiments, provided herein are surprisingly effective technologies for administration and delivery of PAI-1 inhibitors. In some embodiments, the present disclosure teaches topical, oral, and/or injectable formulations and compositions of such PAI-1 inhibitors for hair growth and/or hair re-growth, for subjects suffering from, or pre-disposed to, or have an early onset of androgenetic alopecia, alopecia areata, frontal fibrosing alopecia, and senescent alopecia. In some embodiments, the present disclosure teaches methods of treating and/or preventing one or more conditions of androgenetic alopecia, alopecia areata, frontal fibrosing alopecia, and senescent alopecia, through the administration of PAI-1 inhibitor formulations and/or compositions to a subject in need thereof. In some embodiments, the formulations and/or compositions comprise emulsions.

Moreover, the present disclosure appreciates that certain liquid nanoemulsion technologies have been demonstrated to provide remarkable transdermal delivery attributes, even for very large molecules, such as botulinum and/or antibody agents. See, e.g., U.S. Patent Publication No. 2012/0328701, U.S. Patent Publication No. 2012/0328702, 8,318,181, and U.S. Pat. No. 8,658,391, the disclosures of which are herein incorporated by reference in their entireties. These liquid nanoemulsions are far superior to solid nanoparticle drug delivery, particularly transdermal drug delivery wherein, as noted by Gomaa, the solid nanoparticles cannot penetrate the skin but merely accumulate in the hair follicles. These liquid nanoemulsions are also stable for at least 34 months, making them a commercially viable from this perspective as well.

Macroemulsions

In some embodiments, the present invention utilizes macroemulsion compositions comprising PAI-1 inhibitors that are particularly effective and/or useful in for therapeutic purposes of specific types of hair loss, including androgenetic alopecia, alopecia areata, frontal fibrosing alopecia, and senescent alopecia. In some embodiments, particular macroemulsion compositions are particularly effective and/or useful for topical, oral, and/or injectable administration of PAI-1 inhibitors to a subject in need thereof. In some embodiments macroemulsion compositions may comprise of one or more PAI-1 inhibitors.

In some embodiments, a macroemulsion may be formulated into a composition suitable for topical administration on the skin. In some embodiments, a composition suitable for topical administration may be a lotion, cream, powder, ointment, liniment, gel, or drops.

In some embodiments, macroemulsion formulations comprise water, medium chain triglyceride, span 65, polysorbate 80, methylparaben, and propylparaben. In some embodiments, macroemulsion formulations comprise water, medium chain triglyceride, span 65, and polysorbate 80.

In some embodiments, provided compositions comprise a mixture of a provided macroemulsion composition and one or more pharmaceutically acceptable excipients. In some embodiments, cream and/or lotion formulations comprise a mixture of a provided macroemulsion composition and/or a saline solution.

In some embodiments, provided compositions comprise macroemulsion compositions comprising one or more PAI-1 inhibitors. In some embodiments, provided compositions are cream and/or lotion formulations. In some embodiments, provided cream and/or lotion formulations comprise macroemulsion compositions. In some embodiments, compositions comprise provided macroemulsion compositions but are not cream and/or lotion formulations. In some embodiments, suitable compositions are formulated into creams and/or lotions but do not comprise a macroemulsion composition.

In some embodiments, provided compositions comprise a mixture of a provided macroemulsion composition and one or more pharmaceutically acceptable excipients, e.g., for topical and/or transdermal (e.g., by lotions, creams, powders, ointments, liniments, gels, drops, etc.) administration.

In some embodiments, a macroemulsion may be formulated into a composition suitable for topical administration. In some embodiments, a composition suitable for topical administration may be a lotion, cream, powder, ointment, liniment, gel, or drops. In some embodiments, a macroemulsion may be formulated into an injectable composition. In some embodiments, the injectable composition may be sterile.

Macroemulsion formulations may act to stabilize the active agent and/or therapeutic agent such as PAI-1 inhibitors. Macroemulsion formulations would not necessarily be expected in and of themselves to achieve transdermal delivery of the active agents, nonetheless, the present disclosure encompasses that stabilization improvement that may be provided by incorporation into a macroemulsion composition might, when combined with microneedling technologies as described herein, achieve synergistic enhancement of transdermal delivery.

Nanoemulsions

In some embodiments, the present invention utilizes nanoemulsion compositions comprising PAI-1 inhibitors that are particularly effective and/or useful in for therapeutic purposes of specific types of hair loss, including androgenetic alopecia, alopecia areata, frontal fibrosing alopecia, and senescent alopecia. In some embodiments, particular nanoemulsion compositions are particularly effective and/or useful for topical, oral, and/or injectable administration of PAI-1 inhibitors to a subject in need thereof. In some embodiments nanoemulsion compositions may comprise of one or more PAI-1 inhibitors.

In some embodiments, provided nanoemulsion compositions comprise oil and surfactant at a ratio ranging between about 0.1:1 to about 2:1. In some embodiments, provided nanoemulsion compositions comprise oil and surfactant at a ratio of about 0.1:1 to about 1:1. In some embodiments, provided nanoemulsion compositions comprise oil and surfactant at a ratio of about 0.5:1 to about 1:1. In some embodiments, provided nanoemulsion compositions comprise oil and surfactant at a ratio of about 0.5:1 to about 1:1.5. In some embodiments, provided nanoemulsion compositions comprise oil and surfactant at a ratio of about 0.1:1, about 0.15:1, about 0.2:1, about 0.25:1, about 0.3:1, about 0.35:1, about 0.4:1, about 0.45:1, about 0.5:1, about 0.5:1, about 0.55:1, about 0.6:1, about 0.65:1, about 0.7:1, about 0.75:1, about 0.8:1, about 0.85:1, about 0.9:1, about 0.95:1, or about 1:1 In some embodiments, provided nanoemulsion compositions comprise oil and surfactant at a ratio of about 0.67:1.

In some embodiments, the aqueous dispersion medium (e.g., water, buffer, salt solution, etc.) and surfactant are utilized at a ratio ranging between 0.01 and 20. In some embodiments, the aqueous dispersion medium (e.g., water, buffer, salt solution, etc.) and surfactant are utilized at a ratio ranging between 0.1 and 20. In some embodiments, the aqueous dispersion medium (e.g., water, buffer, salt solution, etc.) and surfactant are utilized at a ratio ranging between 0.5 and 10. In some embodiments, the aqueous dispersion medium (e.g., water, buffer, salt solution, etc.) and surfactant are utilized at a ratio ranging between 0.5 and 1. In some embodiments, the ratio of aqueous dispersion medium (e.g., water, buffer, salt solution, etc.) to surfactant is approximately 0.01:1, approximately 0.02:1, approximately 0.03:1, approximately 0.04:1, approximately 0.05:1, approximately 0.06:1, approximately 0.07:1, approximately 0.08:1, approximately 0.0:1, approximately 0.1:1, approximately 0.2:1, approximately 0.3:1, approximately 0.4:1, approximately 0.5:1, approximately 1:1, approximately 2:1, approximately 3:1, approximately 4:1, approximately 5:1, approximately 6:1, approximately 7:1, approximately 8:1, approximately 9:1 or approximately 10:1. In some embodiments, the ratio of surfactant to water is approximately 0.5:1, approximately 1:1, approximately 2:1, approximately 3:1, approximately 4:1, approximately 5:1, approximately 6:1, approximately 7:1, approximately 8:1, approximately 9:1, approximately 10:1, approximately 11:1, approximately 12:1, approximately 13:1, approximately 14:1, approximately 15:1, approximately 16:1, approximately 17:1, approximately 18:1, approximately 19:1, or approximately 20:1. In some embodiments, aqueous dispersion medium (e.g., water, buffer, salt solution, etc.) and surfactant are utilized at a ratio ranging between 0.5 and 2. In some embodiments, the ratio of aqueous dispersion medium (e.g., water, buffer, salt solution, etc.) to surfactant is approximately 0.5:1, approximately 1:1, or approximately 2:1. In some embodiments, the ratio of surfactant to aqueous dispersion medium (e.g., water, buffer, salt solution, etc.) is approximately 0.5:1, approximately 1:1, or approximately 2:1. In some embodiments, the ratio of aqueous dispersion medium (e.g., water, buffer, salt solution, etc.) to surfactant is approximately 1:1. In some embodiments, compositions utilizing such ratios of aqueous dispersion medium (e.g., water, buffer, salt solution, etc.) to surfactant comprise water-in-oil emulsions.

In some embodiments, droplets within nanoemulsion compositions have diameters (e.g., average and/or median diameters) within a range of about 10 nm to about 300 nm, about 10 nm to about 200 nm, about 10 nm to about 150 nm, about 10 nm to about 130 nm, about 10 nm to about 120 nm, about 10 nm to about 115 nm, about 10 nm to about 110 nm, about 10 nm to about 100 nm, or about 10 nm to about 90 nm. In some embodiments, droplets within nanoemulsion compositions have diameters (e.g., average and/or median diameters) within a range of 1 nm to 300 nm, 1 nm to 200 nm, 1 nm to 150 nm, 1 nm to 120 nm, 1 nm to 100 nm, 1 nm to 75 nm, 1 nm to 50 nm, or 1 nm to 25 nm. In some embodiments, droplets within nanoemulsion compositions have diameters (e.g., average and/or median diameters) of 1 nm to 15 nm, 15 nm to 200 nm, 25 nm to 200 nm, 50 nm to 200 nm, or 75 nm to 200 nm.

In some embodiments, a total droplet distribution is encompassed within a specified range of droplet diameter size. In some embodiments, less than 50%, 25%, 10%, 5%, or 1% of a total droplet distribution is outside of a specified range of droplet diameter sizes. In some embodiments, less than 1% of a total droplet distribution is outside of a specified range of droplet diameter sizes. In some embodiments, a nanoemulsion composition is substantially free of droplets having a diameter larger than 300 nm, 250 nm, 200 nm, 150 nm, 120 nm, 100 nm, 75 nm, 50 nm, or 25 nm. In some embodiments, less than 50%, 25%, 10%, 5%, or 1% of a total droplet distribution have diameters larger than 300 nm, 250 nm, 200 nm, 150 nm, 120 nm, 100 nm, 75 nm, 50 nm, or 25 nm.

In some embodiments, droplets within nanoemulsion compositions have an average droplet size that is under about 300 nm, about 250 nm, about 200 nm, about 150 nm, about 130 nm, about 120 nm, about 115 nm, about 110 nm, about 100 nm, about 90 nm, or about 50 nm. In some embodiments, average droplet size is within a range of about 10 nm and about 300 nm, about 50 nm and about 250, about 60 nm and about 200 nm, about 65 nm and about 150 nm, or about 70 nm and about 130 nm. In some embodiments, average droplet size is about 80 nm and about 110 nm. In some embodiments, average droplet size is about 90 nm and about 100 nm.

In some embodiments, nanoemulsion droplets have a zeta potential ranging between −80 mV and +80 mV. In some embodiments, nanoemulsion droplets have a zeta potential ranging between −50 mV and +50 mV. In some embodiments, nanoemulsion droplets have a zeta potential ranging between −25 mV and +25 mV. In some embodiments, nanoemulsion droplets have a zeta potential ranging between n−10 mV and +10 mV. In some embodiments, nanoemulsion droplets have a zeta potential of about −80 mV, about −70 mV, about −60 mV, about 50 mV, about −40 mV, about −30 mV, about −25 mV, about −20 mV, about −15 mV, about −10 mV, or about −5 mV. In some embodiments, nanoemulsion droplets have a zeta potential of about +50 mV, about +40 mV, about +30 mV, about +25 mV, about +20 mV, about +15 mV, about +10 mV, or about +5 mV. In some embodiments, nanoemulsion droplets have a zeta potential that is about 0 mV In some embodiments, aqueous dispersion media and surfactant are utilized at a ratio ranging between about 8:1 and about 9:1. In some embodiments, aqueous dispersion media and surfactant are utilized at a ratio of about 8:1, about 8.1:1, about 8.2:1, about 8.3:1, about 8.4:1, about 8.5:1, about 8.6:1, about 8.7:1, about 8.8:1, about 8.9:1, about 9:1, etc. In some embodiments, aqueous dispersion media and surfactant are utilized at a ratio of about 8.7:1. In some embodiments, aqueous dispersion media and surfactant are utilized at a ratio of about 8.8:1.

In some embodiments, aqueous dispersion media and oil are utilized at a ratio ranging between about 12:1 and about 14:1. In some embodiments, aqueous dispersion media and surfactant are utilized at a ratio of about 12:1, about 12.1:1, about 12.2:1, about 12.3:1, about 12.4:1, about 12.5:1, about 12.6:1, about 12.7:1, about 12.8:1, about 12.9:1, about 13:1, about 13.1:1, about 13.2:1, about 13.3:1, about 13.4:1, about 13.5:1, about 13.6:1, about 13.7:1, about 13.8:1, about 13.9:1, about 14:1, etc. In some embodiments, aqueous dispersion media and surfactant are utilized at a ratio of about 13.1:1.

In some embodiments, the percent of oil in the nanoemulsion ranges between 0% and 50%. In some embodiments, the percent of oil in the nanoemulsion ranges between 0% and 40%. In some embodiments, the percent of oil in the nanoemulsion ranges between 0% and 30%. In some embodiments, the percent of oil in the nanoemulsion ranges between 0% and 20%. In some embodiments, the percent of oil in the nanoemulsion ranges between 0% and 10%. In some embodiments, the percent of oil in the nanoemulsion ranges between 0% and 5%. In some embodiments, the percent of oil in the nanoemulsion ranges between 5% and 10%, between 10% and 15%, between 15% and 20%, between 20% and 25%, between 25% and 30%, between 35% and 40%, or between 45% and 50%. In some embodiments, the percent of oil in the nanoemulsion ranges between 10% and 20%, between 10% and 30%, between 10% and 40%, or between 10% and 50%. In some embodiments, the percent of oil in the nanoemulsion ranges between 20% and 30%, between 20% and 40%, between 20% and 50%. In some embodiments, the percent of oil in the nanoemulsion ranges between 30% and 40% or between 30% and 50%. In some embodiments, the percent of oil in the nanoemulsion ranges between 40% and 50%.

In some embodiments the percent of oil is approximately 1%, approximately 2%, approximately 3%, approximately 4%, approximately 5%, approximately 6%, approximately 7%, approximately 9%, approximately 10%, approximately 11%, approximately 12%, approximately 13%, approximately 14%, approximately 15%, approximately 16%, approximately 17%, approximately 18%, approximately 19%, approximately 20%, approximately 21%, approximately 22%, approximately 23%, approximately 24%, approximately 25%, approximately 26%, approximately 27%, approximately 28%, approximately 29%, approximately 30%, approximately 31%, approximately 32%, approximately 33%, approximately 34%, approximately 35%, approximately 36%, approximately 37%, approximately 38%, approximately 39%, approximately 40%, approximately 41%, approximately 42%, approximately 43%, approximately 44%, approximately 45%, approximately 46%, approximately 47%, approximately 48%, approximately 49%, or approximately 50%. In some embodiments the percent of oil is approximately 10%. In some embodiments the percent of oil is approximately 9%. In some embodiments the percent of oil is approximately 8%. In some embodiments the percent of oil is approximately 7%. In some embodiments the percent of oil is approximately 6%. In some embodiments the percent of oil is approximately 5%. In some embodiments the percent of oil is approximately 4%. In some embodiments the percent of oil is approximately 3%. In some embodiments the percent of oil is approximately 2%. In some embodiments the percent of oil is approximately 1%.

In some embodiments, nanoemulsion formulations comprise water, medium chain triglyceride, polysorbate 80, methylparaben, and propylparaben. In some embodiments, nanoemulsion formulations comprise water, medium chain triglyceride, and polysorbate 80.

In some embodiments, a nanoemulsion may be formulated into a composition suitable for topical administration. In some embodiments, a composition suitable for topical administration may be a lotion, cream, powder, ointment, liniment, gel, or drops. In some embodiments, a nanoemulsion may be formulated into an injectable composition. In some embodiments, the injectable composition may be sterile.

These compositions are particularly useful in that they can be used for delivery of agents to a subject in need thereof via topical and/or transdermal (e.g., by lotions, creams, powders, ointments, liniments, gels, drops, etc.) administration. In some embodiments, provided cream and/or lotion formulations may be administered to a subject in need thereof via topical and/or transdermal (e.g., by lotions, creams, powders, ointments, liniments, gels, drops, etc.) administration. In some embodiments, provided nanoemulsion compositions may be formulated into cream and/or lotion formulations. In some embodiments, provided cream and/or lotion formulations comprising nanoemulsion compositions may be useful and/or effective for topical administration to a subject. In some embodiments, provided nanoemulsion compositions may be admixed with one or more cream components in a cream formulation (e.g., a provided cream formulation) and/or a saline solution for preparation of a pharmaceutical composition.

The present invention encompasses the recognition that emulsion compositions (e.g., macroemulsion compositions and nanoemulsion compositions) may be formulated into cream and/or lotion formulations for administration to a subject. The present invention encompasses the recognition that provided cream and/or lotion formulations can be particularly useful for formulating emulsions, such as those described herein, for administration to a subject.

Topical Formulations

Compositions as described herein are particularly useful in that they can be used for delivery of PAI-1 inhibitors to a subject in need thereof via topical and/or transdermal (e.g., by lotions, creams, powders, ointments, liniments, gels, drops, etc.) administration. In some embodiments, provided cream and/or lotion formulations comprising PAI-1 inhibitors are administered to a subject in need thereof via topical (e.g., by lotions, creams, powders, ointments, liniments, gels, drops, etc.) administration. In some embodiments, the topical formulations comprise macroemulsions, as described herein. In some embodiments the topical formulations comprise nanoemulsions, as described herein.

In some embodiments, cream and/or lotion formulations comprise purified water, methylparaben, mineral oil, isopropyl myristate, white petrolatum, emulsifying wax, and propylparaben. In some embodiments, cream and/or lotion formulations comprise purified water, mineral oil, isopropyl myristate, white petrolatum, and emulsifying wax.

In some embodiments, the present invention provides particular cream and/or lotion formulations as described herein. In some embodiments, provided cream and/or lotion formulations comprise water. In some embodiments, provided cream and/or lotion formulations comprise methylparaben. In some embodiments, provided cream and/or lotion formulations comprise mineral oil. In some embodiments, provided cream and/or lotion formulations comprise isopropyl myristate. In some embodiments, provided cream and/or lotion formulations comprise white petrolatum. In some embodiments, provided cream and/or lotion formulations comprise emulsifying wax. In some embodiments, provided cream and/or lotion formulations comprise propylparaben. In some embodiments, provided cream and/or lotion formulations do not comprise any parabens. In some embodiments, provided cream and/or lotion formulations do not comprise methylparaben. In some embodiments, provided cream and/or lotion formulations do not comprise propylparaben.

In some embodiments, cream and/or lotion formulations may be useful for topical and/or transdermal administration. The present invention encompasses the recognition that, in some embodiments, provided cream and/or lotion formulations can be particularly useful for delivery of PAI-1 inhibitors, for example, to the hair follicle located in the site of administration. In some embodiments, sites treated include those which used to have hair or hair follicles but no longer have hair or hair follicles. In some embodiments, provided cream and/or lotion formulations are formulated for topical delivery to a subject in need thereof. In some embodiments, provided cream and/or lotion formulations are administered to a subject in need thereof via topical delivery.

In some embodiments, provided compositions are formulated with cosmetically acceptable components. For example, in some embodiments, provided compositions are formulated with water and also any cosmetically acceptable solvent, in particular, monoalcohols, such as alkanols having 1 to 8 carbon atoms (like ethanol, isopropanol, benzyl alcohol and phenylethyl alcohol), polyalcohols, such as alkylene glycols (like glycerine, ethylene glycol and propylene glycol), and glycol ethers, such as mono-, di-, and tri-ethylene glycol monoalkyl ethers, for example, ethylene glycol monomethyl ether and diethylene glycol monomethyl ether, used singly or in a mixture. Such components can be present, for example, in proportions of up to as much as 60%, 70%, 80%, or 90% by weight, relative to the weight of the total composition.

In some embodiments, provided compositions for topical administration include one or more cosmetically acceptable components that impart appearance attributes desirable or appropriate for a subject to which the composition is to be administered (e.g., a matte appearance, which may be particularly desirable or appropriate for administration to subjects having greasy skin).

In some embodiments, provided compositions are formulated with at least one cosmetically acceptable filler material, for example, in order to obtain a matte product, which may be especially desired for individuals with greasy skin.

In some embodiments, one or more PAI-1 inhibitors are formulated into compositions suitable for topical administration. Exemplary PAI-1 inhibitors include those described herein. In some embodiments, provided compositions may be formulated and delivered in combination with microneedle skin conditioning (MSC) so that systemic delivery is achieved; in some embodiments, provided compositions may be formulated and/or delivered so that local, but not systemic, delivery is achieved.

In some embodiments, compositions suitable for topical formulation comprise a penetration enhancing agent. In some embodiments, a penetration enhancing agent degrades, disrupts and/or damages skin structure(s) and/or skin. In some embodiments, a penetration enhancing agent does not degrade, disrupt and/or damage skin structure(s) and/or skin. In some embodiments, a penetration enhancing agent is an irritant. In some embodiments, a penetration enhancing agent is not an irritant.

In some embodiments, the provided compositions may be incorporated into a device such as, for example, a patch. A variety of transdermal patch structures are known in the art; those of ordinary skill will appreciate that provided compositions may readily be incorporated into any of a variety of such structures. In some embodiments, a transdermal patch may comprise a plurality of needles extending from one side of the patch that is administered to the skin.

Those of ordinary skill in the art will appreciate that provided compositions may be incorporated into a device such as, for example, a patch. A variety of transdermal patch structures are known in the art; those of ordinary skill will appreciate that provided compositions may readily be incorporated into any of a variety of such structures. In some embodiments, a transdermal patch may comprise a plurality of needles extending from one side of the patch that is administered to the skin, wherein needles extend from the patch to project through the stratum corneum of the skin. In some embodiments, needles do not rupture a blood vessel. In some embodiments, needles do not penetrate deeply enough to reach nerves in the dermis of the skin.

In some embodiments, a transdermal patch includes an adhesive. Some examples of adhesive patches are well known (for example, see U.S. Design Pat. No. 296,006; and U.S. Pat. Nos. 6,010,715; 5,591,767; 5,008,110; 5,683,712; 5,948,433; and 5,965,154; all of which are incorporated herein by reference). Adhesive patches are generally characterized as having an adhesive layer, which will be administered to a patient's skin, a depot or reservoir for holding a provided composition, and an exterior surface that prevents leakage of the provided composition from the depot. The exterior surface of a patch may be non-adhesive.

In accordance with the present invention, a provided composition is incorporated into a patch so that it remains stable for extended periods of time. For example, in some embodiments, a provided composition may be incorporated into a polymeric matrix that stabilizes an active agent, and permits the agent to diffuse from the matrix and the patch. A provided composition may also be incorporated into an adhesive layer of a patch so that once the patch is administered to the skin, the provided composition may diffuse through the skin. In some embodiments, an adhesive layer may be heat-activated where temperatures of about 37° C. cause the adhesive to slowly liquefy so that the agent diffuses through the skin. The adhesive may remain tacky when stored at less than 37° C., and once administered to the skin, the adhesive loses its tackiness as it liquefies.

In some embodiments, a provided composition can be provided in a depot in a patch so that pressure applied to the patch causes the provided composition to be directed out of the patch through microneedles and through the stratum corneum. Exemplary embodiments of microneedles are described above. Suitable devices for use in administering provided compositions intradermally include devices such as those described in U.S. Pat. Nos. 4,886,499; 5,190,521; 5,328,483; 5,527,288; 4,270,537; 5,015,235; 5,141,496; and 5,417,662. Intradermal compositions may be administered by devices which limit the effective penetration length of a needle into the skin, such as those described in PCT publication WO 99/34850 and functional equivalents thereof.

In some embodiments, for example in order to prolong the effect of a provided composition, it may be desirable to slow absorption of a provided composition into the skin. In some embodiments, this may be accomplished by use of a liquid suspension of crystalline or amorphous material with poor water solubility. The rate of absorption of a provided composition then depends upon its rate of dissolution which, in turn, may depend upon crystal size and crystalline form. In some embodiments, depending upon the ratio of provided composition to polymer and the nature of the particular polymer employed, the rate of provided composition release can be controlled. Examples of other biodegradable polymers include poly(orthoesters) and poly(anhydrides).

Injectable Formulations

Injectable preparations, for example, sterile injectable aqueous or oleaginous suspensions may be formulated according to the known art using suitable dispersing agents, wetting agents, and/or suspending agents. Sterile injectable preparations may be sterile injectable solutions, suspensions, and/or emulsions in nontoxic parenterally acceptable diluents and/or solvents, for example, as a solution in 1,3-butanediol. Among the acceptable vehicles and solvents that may be employed are water, Ringer's solution, U.S.P., and isotonic sodium chloride solution. Sterile, fixed oils are conventionally employed as a solvent or suspending medium. For this purpose any bland fixed oil can be employed including synthetic mono- or diglycerides. Fatty acids such as oleic acid can be used in the preparation of injectables.

Injectable formulations can be sterilized, for example, by filtration through a bacterial-retaining filter, and/or by incorporating sterilizing agents in the form of sterile solid compositions which can be dissolved or dispersed in sterile water or other sterile injectable medium prior to use.

In order to prolong the effect of a provided composition, it may be desirable to slow the absorption of the provided composition from subcutaneous or intramuscular injection. This may be accomplished by the use of a liquid suspension of crystalline or amorphous material with poor water solubility. The rate of absorption of the provided composition then depends upon its rate of dissolution which, in turn, may depend upon crystal size and crystalline form. Alternatively, delayed absorption of a parenterally administered provided composition form is accomplished by dissolving or suspending the provided composition in an oil vehicle. Injectable depot forms are made by forming microencapsule matrices of the provided composition in biodegradable polymers such as polylactide-polyglycolide. Depending upon the ratio of provided composition to polymer and the nature of the particular polymer employed, the rate of provided composition release can be controlled. Examples of other biodegradable polymers include poly(orthoesters) and poly(anhydrides). Depot injectable formulations are prepared by entrapping the provided composition in liposomes or microemulsions which are compatible with body tissues.

Oral Formulations

Solid dosage forms for oral administration include capsules, tablets, pills, powders, and granules. In such solid dosage forms, the provided composition is mixed with at least one inert, pharmaceutically acceptable excipient such as sodium citrate or dicalcium phosphate and/or fillers or extenders (e.g., starches, lactose, sucrose, glucose, mannitol, and silicic acid), binders (e.g., carboxymethylcellulose, alginates, gelatin, polyvinylpyrrolidinone, sucrose, and acacia), humectants (e.g., glycerol), disintegrating agents (e.g., agar, calcium carbonate, potato starch, tapioca starch, alginic acid, certain silicates, and sodium carbonate), solution retarding agents (e.g., paraffin), absorption accelerators (e.g., quaternary ammonium compounds), wetting agents (e.g., cetyl alcohol and glycerol monostearate), absorbents (e.g., kaolin and bentonite clay), and lubricants (e.g., talc, calcium stearate, magnesium stearate, solid polyethylene glycols, sodium lauryl sulfate), and mixtures thereof. In the case of capsules, tablets and pills, the dosage form may comprise buffering agents.

Solid compositions of a similar type may be employed as fillers in soft and/or hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the provided composition(s) only, or preferentially, in a certain part of the intestinal tract, optionally, in a delayed manner. Examples of embedding compositions which can be used include polymeric substances and waxes. Solid compositions of a similar type may be employed as fillers in soft and hard-filled gelatin capsules using such excipients as lactose or milk sugar as well as high molecular weight polyethylene glycols and the like.

35

Administration

The present invention provides technologies for treating specific types of hair loss, including androgenetic alopecia, alopecia areata, frontal fibrosing alopecia, and senescent alopecia, using any of the provided compositions (e.g., provided emulsion compositions; cream and/or lotion formulations; combination of provided emulsion compositions and cream and/or lotion formulation; etc.) as described herein. In some embodiments, the provided compositions are administered in combination with MSC.

As described herein, the present invention provides methods of administering provided compositions to a subject for various applications including, for example, cosmetic and/or medical applications. In some embodiments, the present invention provides methods of treating and/or preventing diseases, disorders, and/or conditions associated with activity of epidermal and/or dermal structures (e.g., sweat glands, sebaceous glands, hair follicles, etc.) by administering provided compositions to a subject in need thereof Site According to the present disclosure, a PAI-1 inhibitor can be administered to a site of interest for treatment and/or prevention of any one or a combination of androgenetic alopecia, alopecia areata, frontal fibrosing alopecia, and senescent alopecia. In some embodiments, a PAI-1 inhibitor may not be particularly useful in the treatment and/or prevention of other types of alopecia such as radiation-induced alopecia, chemotherapy-induced alopecia, and alopecia due to chronic discoid lupus erythematosus.

Technologies of the invention are suitable for both human and veterinary use. In some embodiments, subjects suffering from any one or a combination of androgenetic alopecia, alopecia areata, frontal fibrosing alopecia, and senescent alopecia, which would benefit from topical, oral, and/or injectable administration of a PAI-1 inhibitor may be treated with the disclosed technologies. In some embodiments, subjects suffering from any one or a combination of other types of alopecia such as radiation-induced alopecia, chemotherapy-induced alopecia, and alopecia due to chronic discoid lupus erythematosus, which would not benefit from topical, oral, and/or injectable administration of a PAI-1 inhibitor may not be treated with the disclosed technologies.

Any site suitable site for MSC is a suitable administration site. In some embodiments, an administration site is the skin overlying a muscle or muscle group of a subject. In some embodiments, the site is hairless. In some embodiments, the site is on the torso. In some embodiment the site is on the back. In some embodiments the site is on the chest. In some embodiments, the site is on the buttocks. In some embodiments, the site is on the crotch. In some embodiments, the site is on the groin. In some embodiments, the site is on the head. In some embodiments the site is on the scalp. In some embodiments, the site is on the face. In some embodiments the site is on the neck. In some embodiments the site is on the décolleté. In some embodiments, the site is in the armpit. In some embodiments, the site is on the axillae. In some embodiments the site is on the hands. In some embodiments the site is on the feet. In some embodiments the site is on the arms. In some embodiments the site is on the legs. In some embodiments, the site used to have hair or hair follicles but no longer have hair or hair follicles.

In some embodiments, the site of interest has hair follicles. In some embodiments, the hair follicles have normal structure and/or density. In some embodiments, the hair follicles do not comprise hairs. In some embodiments, the hair follicles comprise hairs. In some embodiments, percentage of hair follicles with hair is about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, or more.

In some embodiments, the hairs in the hair follicles are not gray in color. In some embodiments, the hairs in the hair follicles are gray in color. In some embodiments, percentage gray is about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, or more.

In some embodiments the site is affected by a dermatologic condition.

In some embodiments, the length of the microneedles used in MSC is adjusted based on skin thickness of the treatment site.

In some embodiments, MSC comprises one impression of microneedle (MN) or MN array. In some embodiments, MSC comprises two impressions of MN or MN array. In some embodiments, MSC comprises three impressions of MN or MN array. In some embodiments, MSC comprises four impressions of MN or MN array. In some embodiments, MSC comprises five impressions of MN or MN array. In some embodiments, MSC comprises six impressions of MN or MN array. In some embodiments, MSC comprises seven impressions of MN or MN array. In some embodiments, MSC comprises eight impressions of MN or MN array. In some embodiments, MSC comprises nine impressions of MN or MN array. In some embodiments, MSC comprises ten impressions of MN or MN array. In some embodiments, MSC comprises eleven impressions of MN or MN array. In some embodiments, MSC comprises twelve impressions of MN or MN array. In some embodiments, MSC comprises thirteen impressions of MN or MN array. In some embodiments, MSC comprises fourteen impressions of MN or MN array. In some embodiments, MSC comprises fifteen impressions of MN or MN array. In some embodiments, MSC comprises sixteen impressions of MN or MN array. In some embodiments, MSC comprises seventeen impressions of MN or MN array. In some embodiments, MSC comprises eighteen impressions of MN or MN array. In some embodiments, MSC comprises nineteen impressions of MN or MN array. In some embodiments, MSC comprises twenty impressions of MN or MN array. In some embodiments, the MSC comprises rolling the MN or MN array over the skin one or more times. In some embodiments, an MN array is rotated between impressions. In some embodiments an MN array is not rotated between impressions. In some embodiments impressions are made on the same site. In some embodiments impressions are made on overlapping sites. In some embodiments, impressions are made on different sites. In some embodiments, impressions are made by stamping of a MN array. In some embodiments, impressions are made by rolling a microneedle roller over a site one or more times. In accordance with established MN practices, in some embodiments, the MN array skin impressions last under one second or, alternatively, in some embodiments, they last over one second and may, for example, last for 30 seconds or more, 60 seconds or more, two minutes or more, five minutes or more, ten minutes or more, thirty minutes or more, etc.

Subject

In general the subject is an organism, typically a mammal (e.g., a human, in some embodiments including prenatal human forms). In some embodiments, the subject is male. In some embodiments, subject is female. In some embodiments, the subject is human. In a particular embodiment the human subject is at least 10 years old. In some embodiments, the subject has no hair. In some embodiments, the subject has hair. In some embodiments the subject has low follicle density. In some embodiments, the subject has a high follicle density. In some embodiments, the subject has colored hair. In some embodiments, a subject is suffering from a relevant disease, disorder or condition (e.g. specific types of alopecia disclosed herein). In some embodiments, a subject is susceptible to a disease, disorder, or condition (e.g. specific types of alopecia disclosed herein). In some embodiments, a subject displays one or more symptoms or characteristics of a disease, disorder or condition (e.g. specific types of alopecia disclosed herein). In some embodiments, a subject does not display any symptom or characteristic of a disease, disorder, or condition (e.g. specific types of alopecia disclosed herein). In some embodiments, a subject is someone with one or more features characteristic of susceptibility to or risk of a disease, disorder, or condition (e.g. specific types of alopecia disclosed herein). In some embodiments, a subject is a patient. In some embodiments, a subject is an individual to whom diagnosis and/or therapy is and/or has been administered.

The technologies of the invention are suitable for both human and veterinary use. In some embodiments, subjects suffering from any one or a combination of androgenetic alopecia, alopecia areata, frontal fibrosing alopecia, and senescent alopecia, which would benefit from topical, oral, and/or injectable administration of a PAI-1 inhibitor may be treated with the disclosed technologies. In some embodiments, subjects suffering from any one or a combination of other types of alopecia such as radiation-induced alopecia, chemotherapy-induced alopecia, and alopecia due to chronic discoid lupus erythematosus, which would not benefit from topical, oral, and/or injectable administration of a PAI-1 inhibitor may not be treated with the disclosed technologies.

Route

In general, route is selected to achieve delivery of a therapeutically effective amount to a relevant site of action. Without wishing to be bound by any particular theory, in some embodiments, a site of action may be or comprise a site comprising a hair follicle. In some embodiments, an administration site is the skin overlying a muscle or muscle group of a subject. In some embodiments, the site is hairless. In some embodiments, the site is on the torso. In some embodiment the site is on the back. In some embodiments the site is on the chest. In some embodiments, the site is on the buttocks. In some embodiments, the site is on the crotch. In some embodiments, the site is on the groin. In some embodiments, the site is on the head. In some embodiments the site is on the scalp. In some embodiments, the site is on the face. In some embodiments the site is on the neck. In some embodiments the site is on the décolleté. In some embodiments, the site is in the armpit. In some embodiments, the site is on the axillae. In some embodiments the site is on the hands. In some embodiments the site is on the feet. In some embodiments the site is on the arms. In some embodiments the site is on the legs.

In some embodiments, the present invention provides methods of administration of provided compositions via any route of delivery, including, but not limited to, oral (PO), intravenous (IV), intramuscular (IM), intra-arterial, intramedullary, intrathecal, subcutaneous (SQ), intraventricular, transdermal, interdermal, intradermal, rectal (PR), vaginal, intraperitoneal (IP), intragastric (IG), topical and/or transdermal (e.g., by lotions, creams, liniments, ointments, powders, gels, drops, etc.), mucosal, intranasal, buccal, enteral, vitreal, and/or sublingual administration; by intra-tracheal instillation, bronchial instillation, and/or inhalation; as an oral spray, nasal spray, and/or aerosol, and/or through a portal vein catheter; and/or combinations thereof.

In some embodiments, provided methods involve topical, transdermal, or intradermal administration of provided compositions to the skin of a subject. In some embodiments, such routes achieve local delivery.

In some particular embodiments, provided method involves topical administration of an emulsion composition comprising PAI-1 inhibitors. In some particular embodiments, the emulsion composition is a macroemulsion. In some particular embodiments, the emulsion composition is a nanoemulsion. In some particular embodiments, topical via or in conjunction with MSC.

In some embodiments, an active agent or biologically active agent (e.g. PAI-1 inhibitor) penetrates the skin within about 1, 2, 3, 4, 5, 6, 7, 8, 9, or 10 minutes of administration. In some embodiments, a biologically active agent penetrates the skin within about 5 to about 60 minutes of administration. In some embodiments, a biologically active agent penetrates the skin within about 5 to about 12 minutes of administration. In some embodiments, a biologically active agent penetrates the skin within about 5 to about 15 minutes of administration. In some embodiments, a biologically active agent penetrates the skin within about 15 to about 30 minutes of administration. In some embodiments, a biologically active agent penetrates the skin within about 1 hour of administration. In some embodiments, a biologically active agent penetrates the skin within about 2 hours of administration. In some embodiments, a biologically active agent penetrates the skin within about 3 hours of administration. In some embodiments, a biologically active agent penetrates the skin within about 4 hours of administration. In some embodiments, a biologically active agent penetrates the skin within about 5 hours of administration. In some embodiments, a biologically active agent penetrates the skin within about 6 hours of administration. In some embodiments, a biologically active agent penetrates the skin within about 7 hours of administration. In some embodiments, a biologically active agent penetrates the skin within about 8 hours of administration. In some embodiments, a biologically active agent penetrates the skin within about 12 hours of administration. In some embodiments, a biologically active agent penetrates the skin within about 24 hours of administration.

In some embodiments, a biologically active agent (e.g., PAI-1 inhibitor) penetrates a layer of the skin within about 1, 2, 3, 4, 5, 6, 7, 8, 9, or 10 minutes of administration. In some embodiments, a biologically active agent penetrates a layer of the skin within about 5 to about 60 minutes of administration. In some embodiments, a biologically active agent penetrates a layer of the skin within about 5 to about 12 minutes of administration. In some embodiments, a biologically active agent penetrates a layer of the skin within about 5 to about 15 minutes of administration. In some embodiments, a biologically active agent penetrates a layer of the skin within about 15 to about 30 minutes of administration. In some embodiments, a biologically active agent penetrates a layer of the skin within about 1 hour of administration. In some embodiments, a biologically active agent penetrates a layer of the skin within about 2 hours of administration. In some embodiments, a biologically active agent penetrates a layer of the skin within about 3 hours of administration. In some embodiments, a biologically active agent penetrates a layer of the skin within about 4 hours of administration. In some embodiments, a biologically active agent penetrates a layer of the skin within about 5 hours of administration. In some embodiments, a biologically active agent penetrates a layer of the skin within about 6 hours of administration. In some embodiments, a biologically active agent penetrates a layer of the skin within about 7 hours of administration. In some embodiments, a biologically active agent penetrates a layer of the skin within about 8 hours of administration. In some embodiments, a biologically active agent penetrates a layer of the skin within about 12 hours of administration. In some embodiments, a biologically active agent penetrates a layer of the skin within about 24 hours of administration.

In some embodiments, a biologically active agent penetrates the top layer of the skin within about 1, 2, 3, 4, 5, 6, 7, 8, 9, or 10 minutes of administration. In some embodiments, a biologically active agent penetrates the top layer of the skin within about 5 to about 60 minutes of administration. In some embodiments, a biologically active agent penetrates the top layer of the skin within about 5 to about 12 minutes of administration. In some embodiments, a biologically active agent penetrates the top layer of the skin within about 5 to about 15 minutes of administration. In some embodiments, a biologically active agent penetrates the top layer of the skin within about 15 to about 30 minutes of administration. In some embodiments, a biologically active agent penetrates the top layer of the skin within about 1 hour of administration. In some embodiments, a biologically active agent penetrates the top layer of the skin within about 2 hours of administration. In some embodiments, a biologically active agent penetrates the top layer of the skin within about 3 hours of administration. In some embodiments, a biologically active agent penetrates the top layer of the skin within about 4 hours of administration. In some embodiments, a biologically active agent penetrates the top layer of the skin within about 5 hours of administration. In some embodiments, a biologically active agent penetrates the top layer of the skin within about 6 hours of administration. In some embodiments, a biologically active agent penetrates the top layer of the skin within about 7 hours of administration. In some embodiments, a biologically active agent penetrates the top layer of the skin within about 8 hours of administration. In some embodiments, a biologically active agent penetrates the top layer of the skin within about 12 hours of administration. In some embodiments, a biologically active agent penetrates the top layer of the skin within about 24 hours of administration.

In some embodiments, a biologically active agent penetrates the top layer of the skin, including the stratum corneum, dermal pores, hair follicles, and/or dermal glands within about 1, 2, 3, 4, 5, 6, 7, 8, 9, or 10 minutes of administration. In some embodiments, a biologically active agent penetrates the top layer of the skin, including the stratum corneum, dermal pores, hair follicles, and/or dermal glands within about 5 to about 60 minutes of administration. In some embodiments, a biologically active agent penetrates the top layer of the skin, including the stratum corneum, dermal pores, hair follicles, and/or dermal glands within about 5 to about 12 minutes of administration. In some embodiments, a biologically active agent penetrates the top layer of the skin, including the stratum corneum, dermal pores, hair follicles, and/or dermal glands within about 5 to about 15 minutes of administration. In some embodiments, a biologically active agent penetrates the top layer of the skin, including the stratum corneum, dermal pores, hair follicles, and/or dermal glands within about 15 to about 30 minutes of administration. In some embodiments, a biologically active agent penetrates the top layer of the skin, including the stratum corneum, dermal pores, hair follicles, and/or dermal glands within about 1 hour of administration. In some embodiments, a biologically active agent penetrates the top layer of the skin, including the stratum corneum, dermal pores, hair follicles, and/or dermal glands within about 2 hours of administration. In some embodiments, a biologically active agent penetrates the top layer of the skin, including the stratum corneum, dermal pores, hair follicles, and/or dermal glands within about 3 hours of administration. In some embodiments, a biologically active agent penetrates the top layer of the skin, including the stratum corneum, dermal pores, hair follicles, and/or dermal glands within about 4 hours of administration. In some embodiments, a biologically active agent penetrates the top layer of the skin, including the stratum corneum, dermal pores, hair follicles, and/or dermal glands within about 5 hours of administration. In some embodiments, a biologically active agent penetrates the top layer of the skin, including the stratum corneum, dermal pores, hair follicles, and/or dermal glands within about 6 hours of administration. In some embodiments, a biologically active agent penetrates the top layer of the skin, including the stratum corneum, dermal pores, hair follicles, and/or dermal glands within about 7 hours of administration. In some embodiments, a biologically active agent penetrates the top layer of the skin, including the stratum corneum, dermal pores, hair follicles, and/or dermal glands within about 8 hours of administration. In some embodiments, a biologically active agent penetrates the top layer of the skin, including the stratum corneum, dermal pores, hair follicles, and/or dermal glands within about 12 hours of administration. In some embodiments, a biologically active agent penetrates the top layer of the skin, including the stratum corneum, dermal pores, hair follicles, and/or dermal glands within about 24 hours of administration.

Regimen

In general, regimen is selected to achieve delivery of a therapeutically effective amount to a relevant site of action. In some embodiments the compositions and formulations described herein may be administered to a subject in need thereof at a relevant site of action in a single dose. In some embodiments the compositions and formulations described herein may be administered to a subject in need thereof a relevant site of action in multiple doses. For example, the compositions and formulations described herein, can be administered through any one of the multiple routes of administration described herein (e.g. topical, oral, via injection) sufficient to achieve delivery of effective amount of the biologically active agent (e.g., PAI-1 inhibitor).

In some embodiments, a dosing regimen for a particular active agent (e.g., one or more PAI-1 inhibitors) may involve intermittent or continuous (e.g., by perfusion or other slow release system) administration, for example to achieve a particular desired pharmacokinetic profile or other pattern of exposure in one or more tissues or fluids of interest in the subject receiving therapy.

In some embodiments, different agents administered in combination may be administered via different routes of delivery and/or according to different schedules. Alternatively or additionally, in some embodiments, one or more doses of a first active agent is administered substantially simultaneously with, and in some embodiments via a common route and/or as part of a single composition with, one or more other active agents.

Factors to be considered when optimizing routes and/or dosing schedule for a given therapeutic regimen may include, for example, the particular indication being treated, the clinical condition of a subject (e.g., age, overall health, prior therapy received and/or response thereto) the site of delivery of the agent, the nature of the agent (e.g. an antibody or other polypeptide-based compound), the mode and/or route of administration of the agent, the presence or absence of combination therapy, and other factors known to medical practitioners. For example, in the treatment of cancer, relevant features of the indication being treated may include, for example, one or more of cancer type, stage, location.

In some embodiments, one or more features of a particular pharmaceutical composition and/or of a utilized dosing regimen may be modified over time (e.g., increasing or decreasing the amount of active agent in any individual dose, increasing or decreasing time intervals between doses), for example in order to optimize a desired therapeutic effect or response (e.g., inhibition of the PAI-1 gene or gene product).

In general, type, amount, and frequency of dosing of active agents in accordance with the present invention are governed by safety and efficacy requirements that apply when one or more relevant agent(s) is/are administered to a mammal, preferably a human. In general, such features of dosing are selected to provide a particular, and typically detectable, therapeutic response as compared to what is observed absent therapy.

In the context of the present invention, an exemplary desirable therapeutic response may involve, but is not limited to, inhibition of PAI-1 gene and/or gene product, inhibition and/or a reduction in the degree and/or prevalence of a relevant alopecia, including androgenetic alopecia, alopecia areata, frontal fibrosing alopecia, and senescent alopecia. Such criteria can be readily assessed by any of a variety of immunological, cytological, and other methods that are disclosed in the literature.

In some embodiments, an effective dose (and/or a unit dose) of an active agent, may be at least about 0.01 ng/kg body weight, at least about 0.01 µg/kg body weight, at least about 0.05 µg/kg body weight; at least about 0.1 µg/kg body weight, at least about 1 µg/kg body weight, at least about 2.5 µg/kg body weight, at least about 5 µg/kg body weight, at least about 10 µg/kg body weight, at least about 100 µg/kg body weight, at least about 1 mg/kg body weight, at least about 10 mg/kg body weight, at least about 100 mg/kg body weight, at least about 200 mg/kg body weight, at least about 300 mg/kg body weight, at least about 400 mg/kg body weight, and not more than about 500 mg/kg body weight. It will be understood by one of skill in the art that in some embodiments such guidelines may be adjusted for the molecular weight of the active agent. The dosage may also be varied for route of administration, the cycle of treatment, or consequently to dose escalation protocol that can be used to determine the maximum tolerated dose and dose limiting toxicity (if any) in connection to the administration of the PAI-1 antagonist and/or an additional therapeutic agent at increasing doses. Consequently, the relative amounts of the each agent within a pharmaceutical composition may also vary, for example, each composition may comprise between 0.001% and 100% (w/w) of the corresponding agent.

In some embodiments, a "therapeutically effective amount" or "therapeutically effective dose" is an amount of a PAI-1 antagonist, or a combination of two or more PAI-1 antagonists, or a combination of a PAI-1 antagonist with one or more additional therapeutic agent(s), which inhibits, totally or partially, the progression of the condition or alleviates, at least partially, one or more symptoms of the condition. In some embodiments, a therapeutically effective amount can be an amount which is prophylactically effective. In some embodiments, an amount which is therapeutically effective may depend upon a patient's size and/or gender, the condition to be treated, severity of the condition and/or the result sought. In some embodiments, a therapeutically effective amount refers to that amount of a PAI-1 antagonist that results in amelioration of at least one symptom in a patient. In some embodiments, for a given patient, a therapeutically effective amount may be determined by methods known to those of skill in the art.

In some embodiments, toxicity and/or therapeutic efficacy of PAI-1 antagonists can be determined by standard pharmaceutical procedures in cell cultures or experimental animals, e.g., for determining the maximum tolerated dose (MTD) and the $ED_{50}$ (effective dose for 50% maximal response). Typically, the dose ratio between toxic and therapeutic effects is the therapeutic index; in some embodiments, this ratio can be expressed as the ratio between MTD and $ED_{50}$. Data obtained from such cell culture assays and animal studies can be used in formulating a range of dosage for use in humans.

In some embodiments, dosage may be guided by monitoring a PAI-1 antagonist's effect on one or more pharmacodynamic markers of inhibition in diseased or surrogate tissue. For example, cell culture or animal experiments can be used to determine the relationship between doses required for changes in pharmacodynamic markers and doses required for therapeutic efficacy can be determined in cell culture or animal experiments or early stage clinical trials. In some embodiments, dosage of a PAI-1 antagonist lies preferably within a range of circulating concentrations that include the $ED_{50}$ with little or no toxicity. In some embodiments, dosage may vary within such a range, for example depending upon the dosage form employed and/or the route of administration utilized. The exact formulation, route of administration and dosage can be chosen by the individual physician in view of the patient's condition. In the treatment of crises or severe conditions, administration of a dosage approaching the MTD may be required to obtain a rapid response.

In some embodiments, dosage amount and/or interval may be adjusted individually, for example to provide plasma levels of an active moiety which are sufficient to maintain, for example a desired effect, or a minimal effective concentration (MEC) for a period of time required to achieve therapeutic efficacy. In some embodiments, MEC for a particular PAI-1 antagonist can be estimated, for example, from in vitro data and/or animal experiments. Dosages necessary to achieve the MEC will depend on individual characteristics and route of administration. In some embodiments, high pressure liquid chromatography (HPLC) assays or bioassays can be used to determine plasma concentrations.

In some embodiments, dosage intervals can be determined using the MEC value. In certain embodiments, PAI-1 antagonists should be administered using a regimen which maintains plasma levels above the MEC for 10-90% of the time, preferably between 30-90% and most preferably between 50-90% until the desired amelioration of a symptom is achieved. In other embodiments, different MEC plasma levels will be maintained for differing amounts of time. In cases of local administration or selective uptake, the effective local concentration of the drug may not be related to plasma concentration.

One of skill in the art can select from a variety of administration regimens and will understand that an effective amount of a particular PAI-1 antagonist may be dependent on the subject being treated, on the subject's weight, the severity of the affliction, the manner of administration and/or the judgment of the prescribing physician.

In some embodiments, the present invention involves administration of at least one provided composition, administered according to a dosing regimen sufficient to achieve a reduction in the degree and/or prevalence of a relevant specific type of hair loss (e.g. androgenetic alopecia, alopecia areata, frontal fibrosing alopecia, and senescent alopecia) of at least about 20%; in some embodiments according to a dosing regimen sufficient to achieve a reduction of at least about 25%; in some embodiments according to a dosing regimen sufficient to achieve a reduction of at least about 30%; in some embodiments according to a dosing regimen sufficient to achieve a reduction of at least about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, or more.

In some embodiments, the present invention involves administration of at least one provided composition, administered in combination with MSC, according to a dosing regimen sufficient to achieve a reduction in the degree and/or prevalence of a relevant specific type of hair loss (e.g. androgenetic alopecia, alopecia areata, frontal fibrosing alopecia, and senescent alopecia) of at least about 20%; in some embodiments according to a dosing regimen sufficient to achieve a reduction of at least about 25%; in some embodiments according to a dosing regimen sufficient to achieve a reduction of at least about 30%; in some embodiments according to a dosing regimen sufficient to achieve a reduction of at least about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, or more.

In some embodiments, the present invention involves administration of at least one provided composition, administered optionally in combination with MSC, according to a dosing regimen sufficient to achieve a reduction in the degree and/or prevalence of a relevant specific type of hair loss (e.g. androgenetic alopecia, alopecia areata, frontal fibrosing alopecia, and senescent alopecia) of at least about 20% in a specified percentage of a population of patients to which the composition was administered; in some embodiments according to a dosing regimen sufficient to achieve a reduction of at least about 25% in a specified percentage of a population of patients to which the composition was administered; in some embodiments according to a dosing regimen sufficient to achieve a reduction of at least about 30% in a specified percentage of a population of patients to which the composition was administered; in some embodiments according to a dosing regimen sufficient to achieve a reduction of at least about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90% or more in a specified percentage of a population of patients to which the composition was administered. In some embodiments, the specified percentage of population of patients to which the composition was administered is at least about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%. To give but a few illustrative examples, in some embodiments, the present invention involves administration of at least one provided composition according to a dosing regimen sufficient to achieve a reduction in the degree and/or prevalence of a relevant specific type of hair loss (e.g. androgenetic alopecia, alopecia areata, frontal fibrosing alopecia, and senescent alopecia) of at least about 20% in at least about 50% of the population of patients to which the composition was administered. In some embodiments, the present invention involves administration of at least one provided composition according to a dosing regimen sufficient to achieve a reduction in the degree and/or prevalence of a relevant specific type of hair loss (e.g. androgenetic alopecia, alopecia areata, frontal fibrosing alopecia, and senescent alopecia) of at least about 30% in at least about 50% of the population of patients to which the composition was administered.

The present invention provides technologies for treating conditions or disorders by administering to a patient a provided composition as described herein (e.g., a provided emulsion composition; cream and/or lotion formulation; combination of provided emulsion composition and cream and/or lotion formulation; etc.), optionally in combination with MSC. In some embodiments, the present invention provides technologies for treating conditions or disorders by topically administering to a patient a composition containing a provided emulsion composition, optionally in combination with MSC as described herein.

In some embodiments, an active agent or biologically active agent (e.g. PAI-1 inhibitor) penetrates the skin within about 1, 2, 3, 4, 5, 6, 7, 8, 9, or 10 minutes of administration. In some embodiments, a biologically active agent penetrates the skin within about 5 to about 60 minutes of administration. In some embodiments, a biologically active agent penetrates the skin within about 5 to about 12 minutes of administration. In some embodiments, a biologically active agent penetrates the skin within about 5 to about 15 minutes of administration. In some embodiments, a biologically active agent penetrates the skin within about 15 to about 30 minutes of administration. In some embodiments, a biologically active agent penetrates the skin within about 1 hour of administration. In some embodiments, a biologically active agent penetrates the skin within about 2 hours of administration. In some embodiments, a biologically active agent penetrates the skin within about 3 hours of administration. In some embodiments, a biologically active agent penetrates the skin within about 4 hours of administration. In some embodiments, a biologically active agent penetrates the skin within about 5 hours of administration. In some embodiments, a biologically active agent penetrates the skin within about 6 hours of administration. In some embodiments, a biologically active agent penetrates the skin within about 7 hours of administration. In some embodiments, a biologically active agent penetrates the skin within about 8 hours of administration. In some embodiments, a biologically active agent penetrates the skin within about 12 hours of administration. In some embodiments, a biologically active agent penetrates the skin within about 24 hours of administration.

In some embodiments, a biologically active agent (e.g., PAI-1 inhibitor) penetrates a layer of the skin within about 1, 2, 3, 4, 5, 6, 7, 8, 9, or 10 minutes of administration. In some embodiments, a biologically active agent penetrates a layer of the skin within about 5 to about 60 minutes of administration. In some embodiments, a biologically active agent penetrates a layer of the skin within about 5 to about 12 minutes of administration. In some embodiments, a biologically active agent penetrates a layer of the skin within about 5 to about 15 minutes of administration. In some embodiments, a biologically active agent penetrates a layer of the skin within about 15 to about 30 minutes of administration. In some embodiments, a biologically active agent penetrates a layer of the skin within about 1 hour of administration. In some embodiments, a biologically active agent penetrates a layer of the skin within about 2 hours of administration. In some embodiments, a biologically active agent penetrates a layer of the skin within about 3 hours of administration. In some embodiments, a biologically active agent penetrates a layer of the skin within about 4 hours of administration. In some embodiments, a biologically active agent penetrates a layer of the skin within about 5 hours of administration. In some embodiments, a biologically active agent penetrates a layer of the skin within about 6 hours of administration. In some embodiments, a biologically active agent penetrates a layer of the skin within about 7 hours of administration. In some embodiments, a biologically active agent penetrates a layer of the skin within about 8 hours of administration. In some embodiments, a biologically active agent penetrates a layer of the skin within about 12 hours of administration. In some embodiments, a biologically active agent penetrates a layer of the skin within about 24 hours of administration.

In some embodiments, a biologically active agent penetrates the top layer of the skin within about 1, 2, 3, 4, 5, 6, 7, 8, 9, or 10 minutes of administration. In some embodiments, a biologically active agent penetrates the top layer of the skin within about 5 to about 60 minutes of administration. In some embodiments, a biologically active agent penetrates the top layer of the skin within about 5 to about 12 minutes of administration. In some embodiments, a biologically active agent penetrates the top layer of the skin within about 5 to about 15 minutes of administration. In some embodiments, a biologically active agent penetrates the top layer of the skin within about 15 to about 30 minutes of administration. In some embodiments, a biologically active agent penetrates the top layer of the skin within about 1 hour of administration. In some embodiments, a biologically active agent penetrates the top layer of the skin within about 2 hours of administration. In some embodiments, a biologically active agent penetrates the top layer of the skin within about 3 hours of administration. In some embodiments, a biologically active agent penetrates the top layer of the skin within about 4 hours of administration. In some embodiments, a biologically active agent penetrates the top layer of the skin within about 5 hours of administration. In some embodiments, a biologically active agent penetrates the top layer of the skin within about 6 hours of administration. In some embodiments, a biologically active agent penetrates the top layer of the skin within about 7 hours of administration. In some embodiments, a biologically active agent penetrates the top layer of the skin within about 8 hours of administration. In some embodiments, a biologically active agent penetrates the top layer of the skin within about 12 hours of administration. In some embodiments, a biologically active agent penetrates the top layer of the skin within about 24 hours of administration.

In some embodiments, a biologically active agent penetrates the top layer of the skin, including the stratum corneum, dermal pores, hair follicles, and/or dermal glands within about 1, 2, 3, 4, 5, 6, 7, 8, 9, or 10 minutes of administration. In some embodiments, a biologically active agent penetrates the top layer of the skin, including the stratum corneum, dermal pores, hair follicles, and/or dermal glands within about 5 to about 60 minutes of administration. In some embodiments, a biologically active agent penetrates the top layer of the skin, including the stratum corneum, dermal pores, hair follicles, and/or dermal glands within about 5 to about 12 minutes of administration. In some embodiments, a biologically active agent penetrates the top layer of the skin, including the stratum corneum, dermal pores, hair follicles, and/or dermal glands within about 5 to about 15 minutes of administration. In some embodiments, a biologically active agent penetrates the top layer of the skin, including the stratum corneum, dermal pores, hair follicles, and/or dermal glands within about 15 to about 30 minutes of administration. In some embodiments, a biologically active agent penetrates the top layer of the skin, including the stratum corneum, dermal pores, hair follicles, and/or dermal glands within about 1 hour of administration. In some embodiments, a biologically active agent penetrates the top layer of the skin, including the stratum corneum, dermal pores, hair follicles, and/or dermal glands within about 2 hours of administration. In some embodiments, a biologically active agent penetrates the top layer of the skin, including the stratum corneum, dermal pores, hair follicles, and/or dermal glands within about 3 hours of administration. In some embodiments, a biologically active agent penetrates the top layer of the skin, including the stratum corneum, dermal pores, hair follicles, and/or dermal glands within about 4 hours of administration. In some embodiments, a biologically active agent penetrates the top layer of the skin, including the stratum corneum, dermal pores, hair follicles, and/or dermal glands within about 5 hours of administration. In some embodiments, a biologically active agent penetrates the top layer of the skin, including the stratum corneum, dermal pores, hair follicles, and/or dermal glands within about 6 hours of administration. In some embodiments, a biologically active agent penetrates the top layer of the skin, including the stratum corneum, dermal pores, hair follicles, and/or dermal glands within about 7 hours of administration. In some embodiments, a biologically active agent penetrates the top layer of the skin, including the stratum corneum, dermal pores, hair follicles, and/or dermal glands within about 8 hours of administration. In some embodiments, a biologically active agent penetrates the top layer of the skin, including the stratum corneum, dermal pores, hair follicles, and/or dermal glands within about 12 hours of administration. In some embodiments, a biologically active agent penetrates the top layer of the skin, including the stratum corneum, dermal pores, hair follicles, and/or dermal glands within about 24 hours of administration.

Penetration Enhancing Treatment

According to the present invention, in some embodiments, provided compositions may be administered in combination with one or more penetrating enhancing treatments (e.g. chemical agents, laser treatment, microneedling, physical massage etc.), such as known penetration enhancing agents and/or penetration enhancing treatment modalities, to for example, facilitating penetration of PAI-1 inhibitors across biological barrier (e.g., skin). In some embodiments, provided compositions include one or more such other penetration enhancing agents; in some embodiments, such other penetration enhancing agents are provided as part of distinct compositions. In some embodiments, penetration enhancing treatment involves simultaneous administration of two or more different penetration enhancing agents and/or penetration enhancing treatment modalities; in some embodiments, penetration enhancing treatment involves simultaneous exposure to two or more different penetration enhancing treatment agents and/or penetration enhancing treatment modalities, for example through simultaneous laser treatment and composition administration.

In some embodiments, penetration enhancing agents is or comprises chemical agents. For example, chemical agents that that may damage, disrupt, and/or degrade one or more stratum corneum components) may include, for example, alcohols, such as short chain alcohols, long chain alcohols, or polyalcohols; amines and amides, such as urea, amino acids or their esters, amides, AZONE®, derivatives of AZONE®, pyrrolidones, or derivatives of pyrrolidones; terpenes and derivatives of terpenes; fatty acids and their esters; macrocyclic compounds; tensides; or sulfoxides (e.g., dimethylsulfoxide (DMSO), decylmethylsulfoxide, etc.); surfactants, such as anionic, cationic, and nonionic surfactants; polyols; essential oils; and/or hyaluronidase. In some embodiments, a penetration enhancing agent may be an irritant in that an inflammatory and/or allergic reaction occurs when the agent is administered to skin. In some embodiments, a penetration enhancing agent is not an irritant. In some embodiments, a penetration enhancing agent may be or comprise a chemical agent that does not damage, disrupt, or degrade skin structure but whose presence or level nonetheless correlates with increased penetration of an agent of interest across skin, as compared with that observed in its absence. In some embodiments, co-peptides, carrier molecules, and carrier peptides may be penetration enhancing agents which do not damage, disrupt, and/or degrade skin structure(s). In some embodiments, co-peptides, carrier molecules, and carrier peptides may be penetration enhancing agents which do not irritate the skin. The term "penetration enhancing agent" does not encompass mechanical devices (e.g., needles, scalpels, etc.), or equivalents thereof (e.g., other damaging treatments). Also, those skilled in the art will appreciate that a structure such as a nanoparticle or an emulsion is not a chemical agent and therefore not a chemical penetration enhancing agent even if its presence correlates with enhanced skin penetration of an agent of interest that may be associated with the structure. In some embodiments, penetration enhancing agents is or comprises alcohol.

In some embodiments, penetration enhancing treatment modalities is or comprises microneedling. In some embodiments, penetration enhancing treatment modalities is or comprises laser treatment. In some embodiments, penetration enhancing treatment modalities is or comprises physical massage. For example, in some embodiments, the composition may be administered before or after a performing laser treatment of the site. In some embodiments, penetration enhancing treatment modalities is or comprises administration of an electric or magnetic field.

Microneedling:

In some particular embodiments, microneedle (MN) arrays for use in accordance with the present disclosure are or share features with minimally invasive systems, developed to overcome some of the disadvantages commonly associated with the use of hypodermic and subcutaneous needles, as well as improve patient comfort and compliance. Such disadvantages include, for example, potential for needle tip misplacement with a hypodermic needle because a health professional cannot visualize where exactly the needle is going; such needle misplacement can result in adverse reactions when injected incorrectly. MN would be less prone to such a problem. Other advantages of MN are that they may not cause bleeding, minimize introduction of pathogens through MN produced holes, and eliminate transdermal dosing variability. Other advantages are the possibility of self-administration, reduce risk of accidental needle stick injuries, reduce risk of transmitting infection, and ease of disposal. In some embodiments, MN are multiple microscopic projections assembled on one side of a support, such as a patch or a device (e.g., stamp, roller, array, applicator, pen).

In some embodiments, MN for use in accordance with the present disclosure may be designed and/or constructed in arrays in order to improve skin contact and facilitate penetration into the skin. In some embodiments, utilized MN are of suitable length, width, and shape to minimize contact with nerves when inserted into the skin, while still creating efficient pathways for drug delivery. Alkilani, A. Z., et al., "Transdermal drug delivery: Innovative pharmaceutical developments based on disruption of the barrier properties of the stratum corneum." Pharmaceutics. 7:438-470 (2015).

In some embodiments, a suitable MN may be solid, coated, porous, dissolvable, hollow, or hydrogel MN. Solid MN create microholes in the skin, thereby increasing transport of a drug formulation (e.g., "poke and patch" methods). Coated MN allow for rapid dissolution of a coated drug into the skin (e.g., "coat and poke" methods). Dissolvable MN allow for rapid and/or controlled release of a drug incorporated within the microneedles. Hollow MN may be used to puncture the skin and enable release of a composition following active infusion or diffusion of a formulation through a microneedle's bores (e.g., "poke and flow" methods"). In the case of dissolvable MN, MN can act as a drug depot, holding a drug composition until released by dissolution in the case of dissolvable MN or swelling in the case of hydrogel MN (e.g., "poke and release" methods). However, as already described herein, in many embodiments, the active agent is not delivered by injection via one or more microneedles. That is, in many embodiments, any microneedle utilized in accordance with such embodiments is not coated, loaded, or fabricated with the biologically active agent in any way that would achieve delivery of the biologically active agent. Alternatively, in some embodiments, as described herein, a MN, utilized in accordance with the present disclosure (whether in MSC or otherwise), may comprise and/or deliver a biologically active agent, if the biologically active agent is formulated in a macro- or nano-emulsion composition as described herein. Thus, as will be appreciated by those skilled in the art reading the specification described herein, treatment of skin with microneedle(s) that deliver the biologically active agent (e.g., by injection through a microneedle, by the release of a microneedle coating or by the release from a dissolving microneedle) is not microneedle skin conditioning.

In some embodiments, a microneedle has a diameter which is consistent throughout the microneedle's length. In some embodiments, the diameter of a microneedle is greatest at the microneedle's base end. In some embodiments, a microneedle tapers to a point at the end distal to the microneedle's base. In some embodiments, a microneedle may be solid. In some embodiments, a microneedle may be hollow. In some embodiments a microneedle may be tubular. In some embodiments, a microneedle may be sealed on one end. In some embodiments, a microneedle is part of an array of microneedles. In some embodiments, a microneedle may have a length of between about 1 μm to about 4,000 μm. In some embodiments, a microneedle may have a length of between about 1 μm to about 2,000 μm. In some embodiments, a microneedle may have a length of between about 50 μm to about 400 μm. In some embodiments, a microneedle may have a length of between about 800 μm to about 1500 μm.

In some embodiments, MN for use in accordance with the present disclosure may be fabricated from different materials, using technologies including, but not limited to micromolding processes or lasers. In some embodiments, MN may be manufactured using various types of biocompatible materials including polymers, metal, ceramics, semiconductors, organics, composites, or silicon. Unless they are designed to break off into the skin and dissolve, in some embodiments, microneedles have the mechanical strength to remain intact and to deliver drugs, or collect biological fluid, while being inserted into the skin and/or removed from the skin after insertion. In some embodiments MN are capable of remaining in place for up to a number of days before intact removal. In some embodiments, microneedles may be sterilizable using standard technologies. In some embodiments, MN are biodegradable. In some embodiments, MN comprise a polymeric material. In some embodiments the polymeric material comprises poly-L-lactic acid, poly-glycolic acid, poly-carbonate, poly-lactic-co-glycolic acid (PLGA), polydimethylsiloxane, polyvinylpyrrolidone (PVP), a copolymer of methyl vinyl ether and maleic anhydride, sodium hyaluronate, carboxymethyl cellulose, maltose, dextrin, galactose, starch, gelatin, or a combination thereof.

Suitable MN arrays and MSC devices for use in combination with compositions comprising biologically active agents for transdermal delivery of biologically active agents include devices such as those described in e.g., U.S. Pat. Nos. 6,334,856; 6,503,231; 6,908,453; 8,257,324; and 9,144,671.

Combination Therapy or Treatment

According to the present invention, provided compositions may be administered in combination with one or more additional treatments. In some embodiments the one or more additional treatments is or comprises other active agents and/or therapeutic modalities (e.g. one or more PAI-inhibitors, or other agents), such as known therapeutic agents and/or independently active biologically active agents. In some embodiments, for example, provided compositions include one or more such other active agents; in some embodiments, such other active agents are provided as part of distinct compositions. In some embodiments, combination therapy involves simultaneous administration of one or more doses or units of two or more other active agents and/or therapeutic modalities; in some embodiments, combination therapy involves simultaneous exposure to two or more other active agents and/or therapeutic modalities, for example through overlapping dosing regimens.

In some embodiments, provided compositions include or are administered in combination with one or more other active agents useful for the treatment of the relevant specific type of hair loss (e.g. androgenetic alopecia, alopecia areata, frontal fibrosing alopecia, and senescent alopecia), for example as discussed herein in the context of the relevant disease, disorder, and/or condition.

Kits

In some embodiments, the present invention provides pharmaceutical packs or kits including one or more emulsion compositions comprising one or more PAI-1 inhibitors and/or one or more microneedle devices according to the present invention. In some embodiments, pharmaceutical packs or kits include preparations or pharmaceutical compositions containing provided compositions in one or more containers filled with optionally one or more additional ingredients of pharmaceutical compositions. In some embodiments, a pharmaceutical pack or kit includes an additional approved therapeutic agent for use in combination therapies. In some embodiments, optionally associated with such container(s) can be a notice in the form prescribed by a governmental agency regulating the manufacture, use or sale of pharmaceutical products, which notice reflects approval by the agency of manufacture, use, or sale for human administration.

Kits are provided that include therapeutic reagents and/or active agents, such as PAI-1 inhibitors. As but one non-limiting example, provided compositions can be provided as topical formulations and administered as therapy. Pharmaceutical doses or instructions therefor may be provided in a kit for administration to an individual suffering from or at risk for conditions or disorders, e.g., those associated with the dermal level of the skin.

In some embodiments, a kit may comprise (i) a provided composition; and (ii) at least one pharmaceutically acceptable excipient; and optionally (iii) at least one syringe, spatula, swab for administration to skin; and (iv) instructions for use.

In some embodiments, a kit may comprise (i) a provided composition; and (ii) at least one pharmaceutically acceptable excipient; and optionally (iii) a device for injection (e.g., syringe and needle, microneedle array, hair brush, etc.); and (iv) instructions for use.

It will be appreciated by those of ordinary skill in the art that inventive compositions for topical administration may have a cosmetic formulation such as skin softener, nutrition lotion type emulsion, cleansing lotion, cleansing cream, skin milk, emollient lotion, massage cream, emollient cream, make-up base, facial pack or facial gel, cleaner formulation such as shampoos, rinses, body cleanser, hair-tonics, or soaps, or dermatological composition such as lotions, ointments, gels, creams, patches or sprays. In some embodiments, compositions for topical administration are not formulated for administration to mucous membranes (e.g., are inappropriate for administration to mucous membranes and/or are not formulated to deliver an appropriate amount of large agent to or across mucous membranes).

EXEMPLIFICATION

Example 1: Effects of Topical PAI-1 Inhibitor Formulation on Specific Types of Hair Loss (Alopecia)

A topical study of topical PAI-1 inhibitor formulation after topical administration of a topical formulation of PAI-1 inhibitor (e.g., see Table 1) in man is performed. The study is designed to test whether the topical formulation of PAI-1 inhibitor significantly reduces hair loss in man with specific types of alopecia, namely androgenetic alopecia, alopecia areata, frontal fibrosing alopecia, and senescent alopecia, by measuring hair follicle density following topical treatment with a PAI-1 inhibitor.

The study includes four groups of human subjects. All four groups comprise of sub-groups of 25 human subjects each (see Table 2). All groups have subjects with varying levels of hair follicle density and varying numbers and/or density of hairs. The scalp of each subject in groups I and II are treated twice a day for 6 months topically with a fixed volume of a PAI-1 inhibitor formulation that is at a fixed concentration of the PAI-1 inhibitor. The concentration of the PAI-1 inhibitor in the formulation is 5% w/w. The administration of the topical formulation to the scalp takes about 5 minutes, after which the suspension is left on the site for about 8 to 12 hours. The scalps of the subjects in groups III and IV are treated twice a day for 6 months topically with an empty formulation and is the control.

TABLE

| Group | Sub-Group | Type of Alopecia | Treatments Administered |
|---|---|---|---|
| | Groups and sub-groups of humans for study to test effects of PAI-1 inhibitor formulation on Hair Loss (Alopecia) and treatments administered |
| Group I | A | androgenetic alopecia | PAI-1 inhibitor composition |
| | B | alopecia areata | |
| | C | frontal fibrosing alopecia | |
| | D | senescent alopecia | |
| Group II | E | radiation-induced alopecia | |
| | F | chemotherapy-induced alopecia | |
| | G | alopecia due to chronic discoid lupus erythematosus | |
| Group III | H | androgenetic alopecia | Empty composition |
| | I | alopecia areata | |
| | J | frontal fibrosing alopecia | |
| | K | senescent alopecia | |
| Group IV | L | radiation-induced alopecia | |
| | M | chemotherapy-induced alopecia | |
| | N | alopecia due to chronic discoid lupus erythematosus | |

The expected effect of such a treatment is an increase in the density of hairs and/or increase in hair follicle density at the site of the PAI-1 inhibitor formulation treatment. The number and/or density of hairs and the hair follicle density at the treatment sites is measured by two methods: 1) A photograph of the treated area is taken to observe a change in the hair density; or 2) A hair follicle density test, wherein the hair count in a small site on each subject's scalp is measured. The small site on the scalp is selected prior to the commencement of the study.

A photograph and the hair follicle density test method are employed at baseline prior to a PAI-1 inhibitor treatment. Following this, photographs of the scalp of each subject is obtained every four weeks after start of treatment and at the end of the 6-month study; the hair follicle density test is also performed every four weeks after start of treatment and at the end of the 6-month study. The study finds that at Baseline (i.e. at time 0 days prior to start of the study), the average amount of hairs counted by either the hair follicle density tests or as observed from the photographs is approximately equal across all the control and treatment groups. Photographs of the scalps of the subjects of Group I of the treatment group on average show a visual increase in the total number of hairs with every four weeks. The hair follicle density test also on average shows an increase in the number of hair follicles in the site selected on the scalp of each subject belonging to Group I of the treatment group with every four weeks. In contrast, subjects in Group II of the treatment group and in both the control groups showed no visual increase in hairs in the treatment site, or increase in the density of hair follicles in the selected site on the scalp.

This study establishes that topical administration of the topical formulation of PAI-1 inhibitor increases hair count and initiates hair re-growth in humans with specific types of alopecia, namely androgenetic alopecia, alopecia areata, frontal fibrosing alopecia, and senescent alopecia, but not with other types of alopecia such as radiation-induced alopecia, chemotherapy-induced alopecia, and alopecia due to chronic discoid lupus erythematosus.

Example 2: Effects of Oral PAI-1 Inhibitor Formulation on Specific Types of Hair Loss (Alopecia)

A study of oral administration of an oral formulation of PAI-1 inhibitor in man is performed. The study is designed to test whether the oral formulation of PAI-1 inhibitor significantly reduces hair loss in man with specific types of alopecia, namely androgenetic alopecia, alopecia areata, frontal fibrosing alopecia, and senescent alopecia, by measuring hair follicle density following topical treatment with a PAI-1 inhibitor.

The study includes four groups of human subjects. All four groups comprise of sub-groups of 25 human subjects each (see Table 2). All groups have subjects with varying levels of hair follicle density and varying numbers and/or density of hairs. Each subject in groups I and II is administered an oral formulation of PAI-1 inhibitor formulated as a 75 mg capsule thrice a day for 6 months. Each subject in groups III and IV are administered an oral empty formulation formulated as a 75 mg capsule thrice a day for 6 months and serve as the control.

The expected effect of such a treatment is an increase in the density of hairs and/or increase in hair follicle density due to PAI-1 inhibitor formulation treatment. The number and/or density of hairs and the hair follicle density at the treatment sites is measured by two methods: 1) A photograph of the treated area is taken to observe a change in the hair density; or 2) A hair follicle density test, wherein the hair count in a small site on each subject's scalp is measured. The small site on the scalp is selected prior to the commencement of the study.

A photograph and the hair follicle density test method are employed at baseline prior to a PAI-1 inhibitor treatment. Following this, photographs of the scalp of each subject is obtained every four weeks after start of treatment and at the end of the 6-month study; the hair follicle density test is also performed every four weeks after start of treatment and at the end of the 6-month study. The study finds that at Baseline (i.e. at time 0 days prior to start of the study), the average amount of hairs counted by either the hair follicle density tests or as observed from the photographs is approximately equal across all the control and treatment groups. Photographs of the scalps of the subjects of Group I of the treatment group on average show a visual increase in the total number of hairs with every four weeks. The hair follicle density test also on average shows an increase in the number of hair follicles in the site selected on the scalp of each subject belonging to Group I of the treatment group with every four weeks. In contrast, subjects in Group II of the treatment group and in both the control groups showed no visual increase in hairs in the treatment site, or increase in the density of hair follicles in the selected site on the scalp.

This study establishes that oral administration of the PAI-1 inhibitor increases hair count and initiates hair regrowth in humans with specific types of alopecia, namely androgenetic alopecia, alopecia areata, frontal fibrosing alopecia, and senescent alopecia, but not with other types of alopecia such as radiation-induced alopecia, chemotherapy-induced alopecia, and alopecia due to chronic discoid lupus erythematosus.

Example 3: A Controlled Study Treating Human Scalp Grafts Afflicted with Androgenetic Alopecia with Topical and Oral PAI-1 Inhibitor Formulation Ninety 3 mm full thickness punch scalp biopsies were obtained from male subjects with Androgenetic Alopecia that was assessed to be of intermediate severity according to the Hamilton-Norwood alopecia scale Type IV-V (see Classifications of Patterned Hair Loss: A Review, *J Cutan Aesthet Surg.*, 2016, 9(1): 3-12). These scalp biopsies were taken from the vertex or frontal region of the scalp that formerly had normal hair growth but at the time of biopsy had "intermediate vellus baldness", i.e., the hair demonstrated characteristics of vellus and terminal hairs.

The biopsies were implanted into the dorsal skin of 7-week old SCID Beige male mice, with three grafts implanted into each of a total of 30 mice. Implanted grafts were allowed to engraft for ten days prior to treatment.

10 mice were assigned to Group 1 ("Topical Vehicle"), which received twice daily treatment of the vehicle. 10 mice were assigned to Group 2 ("Topical Active"), which received twice daily treatment of a topical formulation described herein (e.g., see Table 1), containing a Plasminogen-Activator Inhibitor-1 ("PAI-1") inhibitor formulation in the same vehicle used with Group 1. 10 mice were assigned to Group 3 ("Oral Active"), which received chow that the mice were able to eat ad libitum and was enriched with the same PAI-1 inhibitor formulation used with Group 2.

Photographs were taken of every graft immediately prior to the initiation of treatment ("Baseline") and every four weeks thereafter until 16 weeks of observations had been completed. The number of human hairs observed in each graft was counted at the same time intervals, and the mean number of hairs per graft in each treatment group was calculated as was the percentage change in the mean number of hairs observed per graft for each treatment group. The percentage change in the mean number of hairs observed per graft from Baseline to week 16 for the Vehicle Group was 80%; for the Topical Active group, 259%; and for the Oral Active Group, 395%.

In summary, both of the topical and oral formulations of PAI-1 inhibitor were associated with materially greater (e.g., about 3 to about 4.5 times more) hair growth than was the control vehicle.

The PAI-1 inhibitor was concluded to be an effective treatment for androgenetic alopecia.

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

I claim:

1. A method of treating, or preventing the occurrence or progression of one or more conditions, the method comprising:

administering a composition that comprises a PAI-1 inhibitor selected from the group consisting of: 5-Chloro-2-{[(2-{[3-(furan-3-yl)phenyl]amino}-2-oxoethoxy)acetyl]amino}benzoic acid and 5-Chloro-2-{[{[3-(furan-3-yl)phenyl]amino}(oxo)acetyl]amino} benzoic acid to a subject, wherein the subject possesses a site that contains or did contain a plurality of hair follicles, each hair follicle optionally comprising a hair therein, wherein the subject is suffering from one or more conditions, and wherein the one or more conditions are selected from the group consisting of androgenetic alopecia, frontal fibrosing alopecia, and senescent alopecia.

2. The method of claim 1, wherein the administering is by topically applying a composition comprising the PAI-1 inhibitor to a site on a skin surface.

3. The method of claim 2, wherein the administering comprises maintaining the composition on the skin surface for a period of time that is at least one minute or at least one hour.

4. The method of claim 1, wherein the administering is by injection.

5. The method of claim 1, wherein the administering is by oral administration.

6. The method of claim 3 further comprising, after the period of time, removing remaining composition from the site.

7. The method of claim 3, wherein the step of administering the composition comprises massaging the composition into the site.

8. The method of claim 1, further comprising administering one or more other active agents, wherein the one or more other active agents is selected from the group comprising of minoxidil, finasteride, dutasteride, platelet-rich plasma, and combinations thereof.

9. The method of claim 1, further comprising a step of administering a penetrating treatment.

10. The method of claim 9, wherein the penetrating treatment is or comprises a non-irritating chemical agent.

11. The method of claim 9, wherein the penetrating treatment is or comprises microneedling.

12. The method of claim 1, wherein the PAI-1 inhibitor penetrates the site within about 1 minute, 2 minutes, 3 minutes, 4 minutes, 5 minutes, 6 minutes, 7 minutes, 8 minutes, 9 minutes, 10 minutes, 1 hour, 2 hours, 3 hours, 4 hours, 5 hours, 6 hours, 7 hours, 8 hours, 9 hours, 10 hours, 11 hours, 12 hours, or 24 hours of administration.

13. The method of claim 1, wherein the PAI-1 inhibitor penetrates the site within a period of time that is about 5 to about 60 minutes of administration.

14. The method of claim 1, comprising at least first and second administrations of the composition wherein each administration is separated in time from its immediate prior administration.

15. The method of claim 1, wherein the hair is not gray.

16. The method of claim 1, wherein the hair is gray.

17. The method of claim 1, wherein the composition is formulated as a suspension, a foam, a lotion, a cream, a gel, an oil, a powder, a liniment, or drops.

18. The method of claim 2, wherein the administering comprises maintaining the composition on the skin surface for a period of time in the range of 1 to 10 minutes.

19. The method of claim 1, wherein the PAI-1 inhibitor penetrates the site within a period of time that is about 5 to about 12 minutes of administration.

20. The method of claim 1, wherein the PAI-1 inhibitor penetrates the site within a period of time that is about 5 to about 15 minutes of administration.

21. The method of claim 1, wherein the PAI-1 inhibitor penetrates the site within a period of time that is about 15 to about 30 minutes of administration.

22. The method of claim 1, wherein the PAI-1 inhibitor penetrates the site within a period of time that is about 1 to about 12 hours of administration.

23. The method of claim 1, wherein the PAI-1 inhibitor penetrates the site within a period of time that is about 8 to about 12 hours of administration.

24. The method of claim 1, wherein the PAI-1 inhibitor penetrates the site within a period of time that is 12 hours to about 24 hours of administration.

* * * * *